US008980276B2

(12) United States Patent
Brown et al.

(10) Patent No.: US 8,980,276 B2
(45) Date of Patent: Mar. 17, 2015

(54) CONJUGATES FOR THE PREVENTION OR TREATMENT OF NICOTINE ADDICTION

(75) Inventors: Alan Daniel Brown, Deal (GB); Heather Lynn Davis, Dunrobin (CA); David P. Gervais, Gomeldon (GB); Lyn Howard Jones, Canterbury (GB); James R. Merson, Rancho Santa Fe, CA (US); David Cameron Pryde, Walmer (GB); David R. Stead, San Diego, CA (US); Michael J. McCluskie, Ottawa (CA); Jennifer Marie Thorn, Chesterfield, MO (US); Paul Robert Mehelic, St. Charles, MO (US); Parag Ashok Kolhe, Wildwood, MO (US); Keshab Bhattacharya, Brentwood, MO (US); Jari Ilmari Finneman, Glencoe, MO (US); Erin Kristen Parsons, University City, MO (US); Nickolas Anastasiou, Chesterfield, MO (US)

(73) Assignee: Pfizer Inc, New York, NY (US)

( * ) Notice: Subject to any disclaimer, the term of this patent is extended or adjusted under 35 U.S.C. 154(b) by 373 days.

(21) Appl. No.: 13/151,590

(22) Filed: Jun. 2, 2011

(65) Prior Publication Data

US 2011/0300174 A1 Dec. 8, 2011

Related U.S. Application Data

(60) Provisional application No. 61/351,342, filed on Jun. 4, 2010.

(51) Int. Cl.
| | |
|---|---|
| *A61K 39/00* | (2006.01) |
| *A61K 47/48* | (2006.01) |
| *A61K 31/465* | (2006.01) |
| *C07D 401/04* | (2006.01) |

(52) U.S. Cl.
CPC ........... *A61K 47/4833* (2013.01); *A61K 31/465* (2013.01); *A61K 47/48261* (2013.01); *C07D 401/04* (2013.01)
USPC .... 424/195.11; 530/350; 530/402; 546/279.1

(58) Field of Classification Search
None
See application file for complete search history.

(56) References Cited

U.S. PATENT DOCUMENTS

| 4,469,863 | A | 9/1984 | Ts'o et al. | |
|---|---|---|---|---|
| 5,023,243 | A | 6/1991 | Tullils | |
| 6,406,705 | B1 * | 6/2002 | Davis et al. | 424/278.1 |
| 6,945,942 | B2 | 9/2005 | Van Bladel et al. | |
| 7,611,481 | B2 | 11/2009 | Cleary et al. | |
| 7,776,620 | B2 | 8/2010 | Ennifar et al. | |
| 2002/0082543 | A1 | 6/2002 | Park et al. | |
| 2005/0197308 | A1 | 9/2005 | Dalton et al. | |
| 2006/0111271 | A1 | 5/2006 | Cerny et al. | |
| 2008/0269685 | A1 | 10/2008 | Singh et al. | |

FOREIGN PATENT DOCUMENTS

| WO | WO9961054 | 12/1999 |
|---|---|---|
| WO | WO0170730 | 9/2001 |
| WO | WO0249667 | 6/2002 |
| WO | WO03082329 | 10/2003 |
| WO | WO2006138719 | 12/2006 |
| WO | WO2011031327 | 3/2011 |

OTHER PUBLICATIONS

Benowitz, N Engl J Med 362(24):2295-2303, 2010.*
Maurer et al., Expert Opin Investig Drugs 16(11):1775-1783, 2007.*
Pearse et al (Advanced DRug Delivery Reviews 57:465-474, 2005).*
Pavliakova et al (Infect Immun, 68(4):2161-66, 2000).*
Goodchild, J., "Conjugates of Oligonucleotides and Modified Oligonucleotides: A Review of Their Synthesis and Properties," Bioconjugate Chemistry, 1990, 165-187, vol. 1, No. 3.
Martanto, W., et al., "Transdermal Delivery of Insulin Using Microneedles in Vivo," Pharmaceutical Research, 2004, 947-952, vol. 21, No. 6.
McAllister, D., et al., "Microfabricated needles for transdermal delivery of macromolecules and nanoparticles: Fabrication methods and transport studies," PNAS, 2003, 13755-13760, vol. 100, No. 24.
Prausnitz, M., "Microneedles for transdermal drug delivery," Advanced Drug Delivery Reviews, 2004, 581-587, vol. 56.
Uhlmann, E., et al., "Antisense Oligonucleotides: A New Therapeutic Principle," Chemical Reviews, 1990, 543-584, vol. 90, No. 4.
Zahn, J., et al., "Continuous On-Chip Micropumping for Microneedle Enhanced Drug Delivery," Biomedical Microdevices, 2004, 183-190, vol. 6, No. 3.
International Search Report.
Bremer, P., "Investigating the Effects of a Hydrotytically Stable Hapten and a Th1 Adjuvant on Heroin Vaccine Performance", J. Med. Chem., 2012, 55, 10776-10780.

(Continued)

*Primary Examiner* — Patricia A Duffy
(74) *Attorney, Agent, or Firm* — Keith D. Hutchinson; Matthew J. Pugmire

(57) ABSTRACT

The present invention relates in part to nicotine-derived hapten-carrier conjugates of the formula (III):

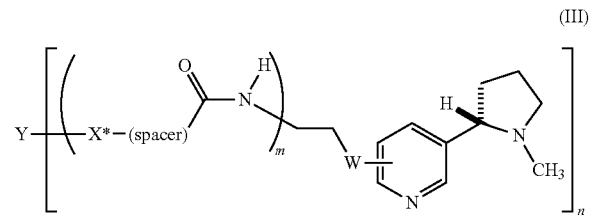

(III)

wherein m, n, W, -(spacer)-, X* and Y are as defined in the description. In certain embodiments, said nicotine-derived hapten-carrier conjugates can be used to prepare vaccines for the treatment and/or prevention of nicotine addiction.

8 Claims, 22 Drawing Sheets

(56) References Cited

OTHER PUBLICATIONS de Villiers, S., "Nicotine hapten structure, antibody selectivity and effect relationships: Results from a nicotine vaccine screening procedure", Vaccine, 28 (2010) 2161-2168.

Escobar-Chavez, J., "Targeting nicotine addiction: the possibility of a therapeutic vaccine", Drug Design, Development and Therapy, 2011:5, 211-224.

Keyler, D., "Enhanced innumogenicity of a bivalent nicotine vaccine", International Immunopharmacology (2008), 8, 1589-1594.

McCluskie, M., "A Novel Anti-Nicotine Vaccine: Antigen Design Affects Antibody Function in Mice", XIV Annual Meeting of the SRNT Europe, University of Helsinki, Finland, Sep. 2, 2012.

Tonstad, S., "Niccine, a Nicotine Vaccine, for Relapse Prevention: A Phase II, Randomized, Placebo-Controlled, Multicenter Clinical Trial", Nicotine and Tobacco Research Advance Access published Mar. 7, 2013.

\* cited by examiner

| Preparation | Conc (µM) 50% inhibition. |
|---|---|
| 7 | 16.6 |
| 8 | 22.6 |
| 4 | 19.3 |
| 12 | 17.7 |

FIG. 16
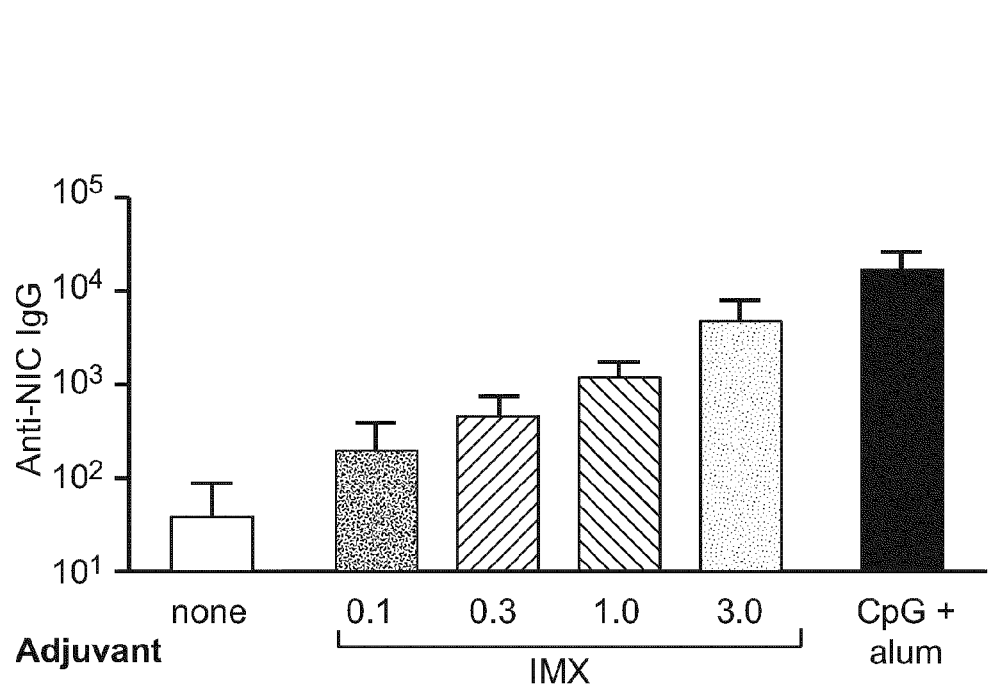
[i]
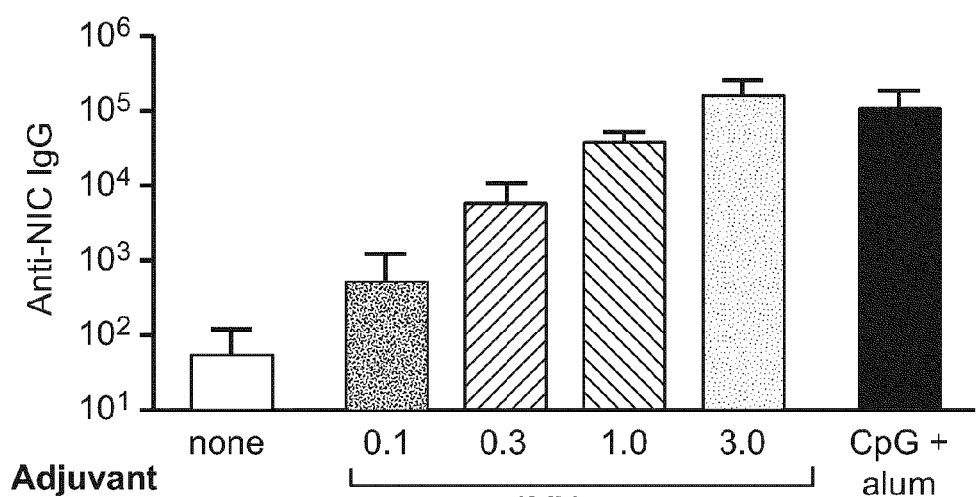
[ii]

CONJUGATES FOR THE PREVENTION OR TREATMENT OF NICOTINE ADDICTION

TECHNICAL FIELD

The present invention relates to nicotine-derived haptens, hapten-spacer conjugates and hapten-carrier conjugates that serve as the antigenic component in anti-nicotine vaccines. The invention also relates to vaccine compositions containing such nicotine-derived hapten-carrier conjugate antigens formulated with adjuvants. Such compositions are used to enhance quit rates or reduce relapse rates in smoking cessation and tobacco/nicotine dependence treatment efforts.

BACKGROUND

Smoking has many serious adverse effects on health and with many government initiatives to reduce or prevent smoking, it has become less socially acceptable. Consequently, many smokers wish to quit the habit, and while many make attempts each year, only a small minority of those who manage to quit do not relapse. The very high failure rate is the result of the addictive nature of nicotine plus the easy availability of cigarettes.

With smoking, or use of nicotine in other forms (e.g., sinus, patches, gum), nicotine enters the bloodstream and rapidly thereafter enters the brain, where it stimulates nicotinic acetylcholine receptors, causing release of dopamine, which in turn activates reward centres. With a smoking quit attempt, there is a loss of the reward response, as well as withdrawal symptoms including a decline in cognitive function. The main reason for relapse is that the loss of reward and the unpleasant withdrawal symptoms can immediately be relieved by smoking.

There are various non-vaccine therapies for smoking cessation. Nicotine replacement therapy, such as nicotine containing chewing gum or skin patches, may help wean smokers off cigarettes but they do not break the addiction cycle that nicotine causes. Another approach is the use of drugs that target nicotinic acetylcholine receptors, such as varenicline. Such drugs, which reduce the rewards normally encountered by smoking, have been relatively successful in aiding smoking cessation, however relapse rates are high after drug treatment ends since a lapse (e.g., smoking a single cigarette) can easily turn into a full relapse with reactivation of reward centres.

More recent nicotine cessation strategies have focused on vaccines that stimulate the immune system to produce anti-nicotine antibodies that bind to nicotine in the bloodstream, thus reducing the amount and rate that nicotine can enter the brain. This in turns prevents reward centres from being activated and helps break the addiction cycle. Since antibodies induced by vaccines can be long-living, anti-nicotine vaccines are useful both to assist in smoking cessation as well as prevention of relapse. Additionally, since the antibodies act in the periphery, there is no risk of central nervous system (CNS) adverse effects. Examples of such vaccines are described in WO 00/32239, WO 02/49667, WO 03/82329 and US 2006/111271. Nicotine derivatives are described in EP-A-421762, WO 01/70730, WO 01/80844 and US 2005/119480. Further nicotine derivatives have been identified under registry numbers 136400-02-7, 250683-10-4, 861023-80-5 and 861025-04-9. Nicotine haptens are described in WO 99/61054, WO 02/58635, WO 03/82329, WO 2005/40338 and EP-A-1849780.

SUMMARY

The present invention relates to nicotine-derived haptens, hapten-spacer conjugates, and conjugation methods which can be used to prepare immunogenic hapten-carrier conjugates for use in vaccines designed to enhance quit rates or reduce relapse rates in smoking cessation treatment efforts. The invention also relates to vaccine formulations containing the above-mentioned conjugates together with adjuvants or excipients, which are used for immunization of smokers in order to elicit antibodies against the haptens, which in turn will also recognize and specifically bind to nicotine. The invention further relates to a method to enhance quit rates or reduce relapse rates in smoking cessation treatment efforts which comprises administering the hapten-carrier conjugate to smokers wishing to quit. In other embodiments the vaccine could be used in non-smokers to prevent them from becoming addicted to nicotine if they were subsequently exposed to it by smoking or other means.

The nicotine-derived hapten-carrier conjugates of the invention may have the advantage that they are more immunogenic, are more specific, are more stable, or have other more useful properties than the nicotine-derived hapten-carrier conjugates known in the art.

The nicotine-derived hapten-carrier conjugates of the invention may be more immunogenic antigens than other known nicotine-derived hapten-carrier conjugates for use in anti-nicotine vaccines. As well, the vaccine formulations containing the nicotine-derived hapten-carrier conjugates of the invention as antigen together with adjuvants may be more immunogenic than other anti-nicotine vaccine formulations, which are typically adjuvanted with aluminium hydroxide, and result in higher quit rates and lower relapse rates amongst patients who are dependent on nicotine/tobacco and wish to quit smoking. Due to better immunogenicity inherent within the antigen, as well as enhanced by the adjuvants, the vaccine formulations of the invention may also achieve higher anti-nicotine antibody titres more quickly and with fewer doses, resulting in improved compliance compared to the vaccine formulations known in the art.

The synthetic routes to the nicotine-derived hapten compounds of the invention may have the advantage that they provide an increased overall synthetic yield (preferably up to a 20 fold increase in overall synthetic yield), involve a reduced number of synthetic steps, result in increased purity of the resulting nicotine-derived haptens (e.g. >99% purity) or have other more useful properties than the synthetic routes to the nicotine-derived hapten compounds known in the art.

μg) with conjugates being using different linkers (Preparations 24-34) by intra-muscular vaccination (on days 0, 28, 42) in the presence of aluminium hydroxide (alum; Alhydrogel-85: 40 μg $Al^{3+}$) and CpG 24555 (50 μg). Anti-nicotine antibody levels (total IgG) in plasma were measured by ELISA.

Figure 13:
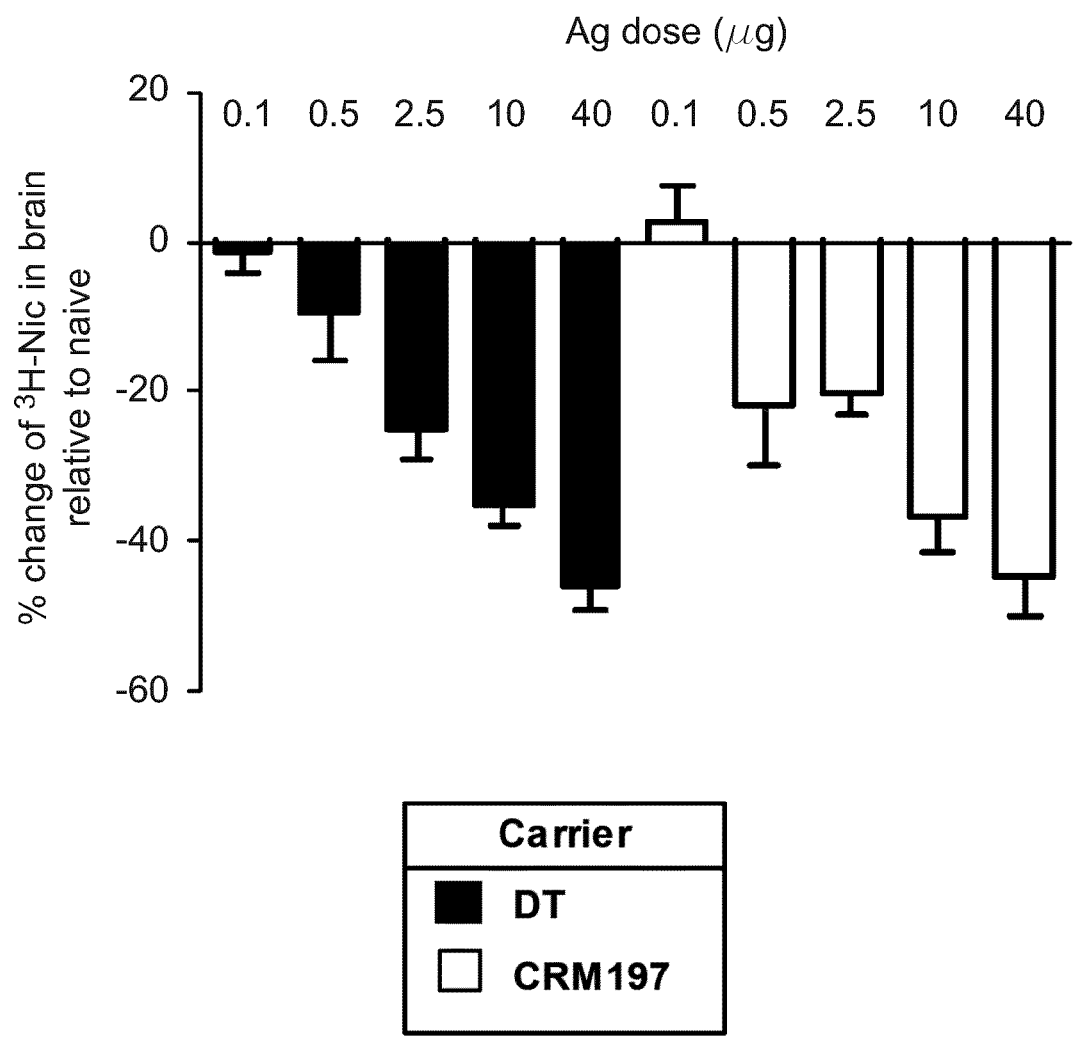

FIG. 13 shows the effect of immunization of mice with anti-nicotine vaccines on the $^3$H-nicotine distribution in mice BALB/c mice (n=12 per group) were immunized with nicotine-derived hapten (Preparation 12; 5'aminoethoxy nicotine) conjugated to diphtheria toxoid (DT; 10 μg) or $CRM_{197}$ (10 μg) by intra-muscular vaccination (on days 0, 28, 42) in the presence of aluminium hydroxide (alum; Alhydrogel-85: 40 μg $Al^{3+}$) and CpG 24555 (50 μg). At two weeks post the third immunization, $^3$H-nicotine (0.05 mg/kg nicotine containing 3 μCi $^3$H-nic) was administered by IV injection, blood collected, animals perfused, brains removed, levels of $^3$H quantified and % change in $^3$H-nicotine in brains relative to control animals was determined.

Figure 14:
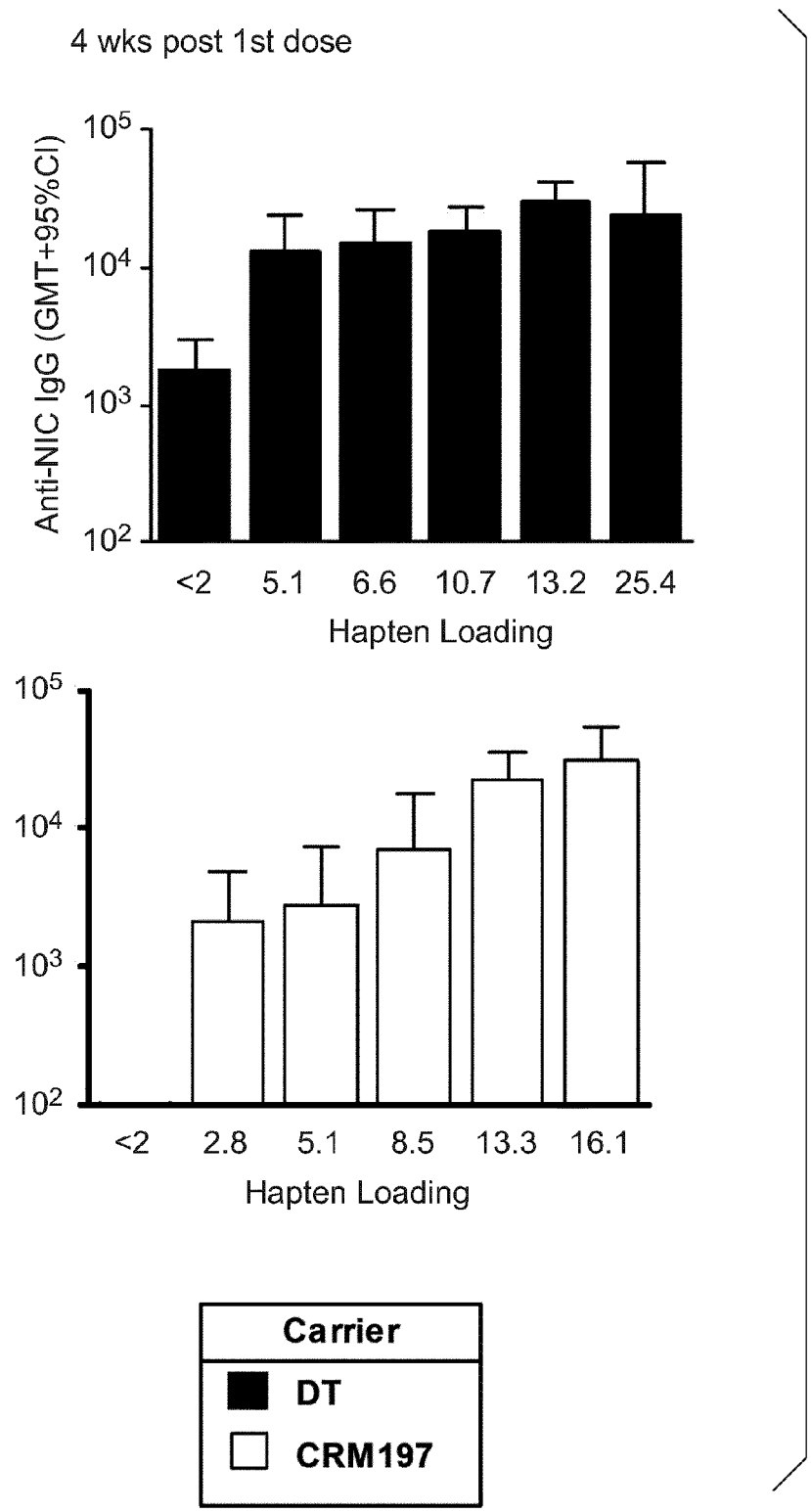

FIG. 14 shows the effect of immunization of mice with anti-nicotine vaccines on the anti-nicotine antibody levels in plasma at various time points. BALB/c mice (n=12 per group) were immunized with nicotine-derived hapten (Preparation 12; 5'aminoethoxy nicotine) conjugated to diphtheria toxoid (DT; 10 μg) or $CRM_{197}$ (10 μg) by intra-muscular vaccination (on days 0, 28, 42) in the presence of aluminium hydroxide (alum; Alhydrogel-85: 40 μg $Al^{3+}$) and CpG 24555 (50 μg). A range of different hapten loadings were evaluated. Anti-nicotine antibody levels (total IgG) in plasma were measured by ELISA.

Figure 15:
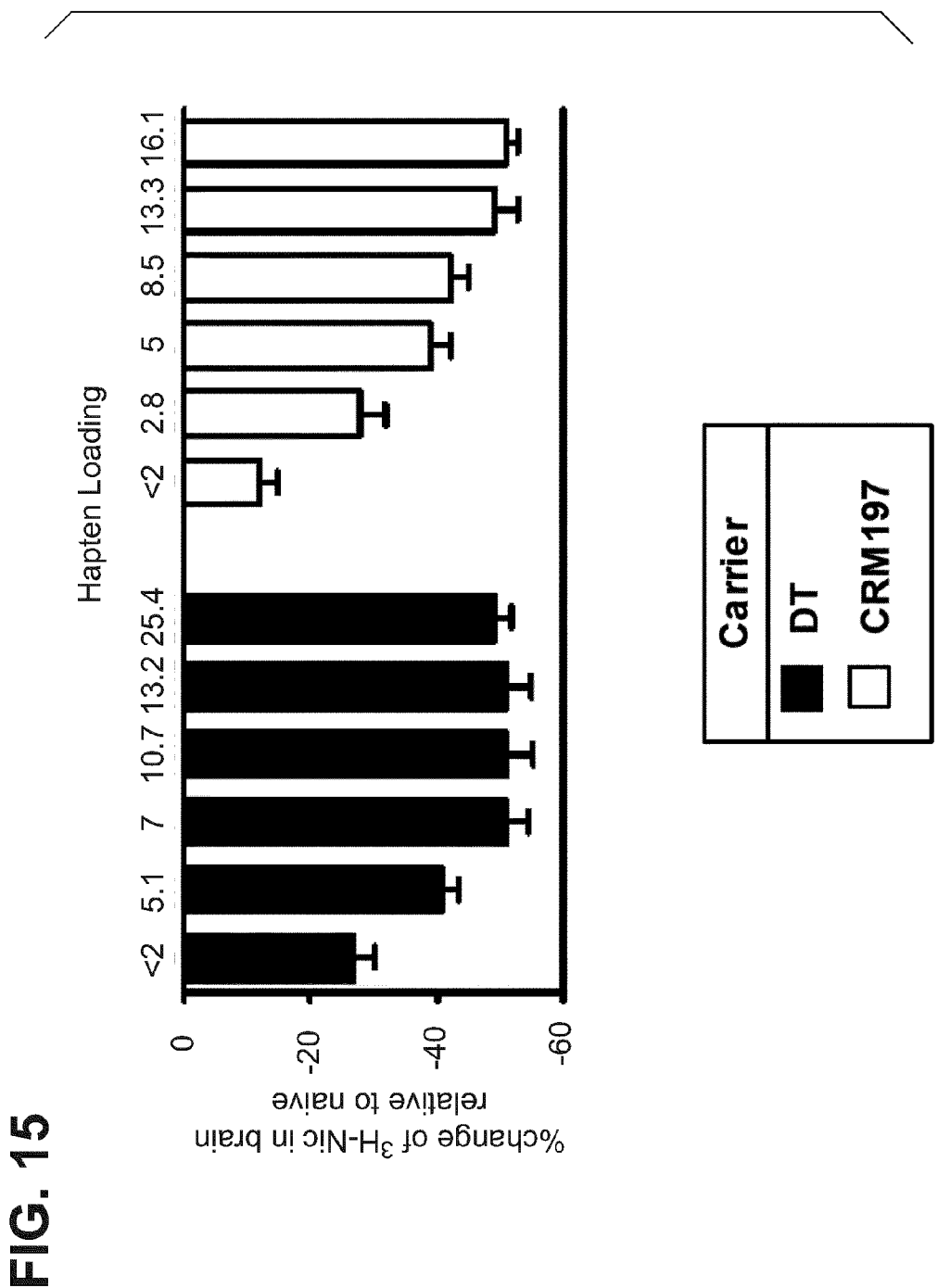

FIG. 15 shows the effect of immunization of mice with anti-nicotine vaccines on the $^3$H-nicotine distribution in mice. BALB/c mice (n=12 per group) were immunized with nicotine-derived hapten (Preparation 12; 5'aminoethoxy nicotine) conjugated to diphtheria toxoid (DT; 10 μg) or $CRM_{197}$ (10 μg) by intra-muscular vaccination (on days 0, 28, 42) in the presence of aluminium hydroxide (alum; Alhydrogel-85: 40 μg $Al^{3+}$) and CpG 24555 (50 μg). A range of different hapten loadings were evaluated. At two weeks post the third immunization, $^3$H-nicotine (0.05 mg/kg nicotine containing 3 μCi $^3$H-nic) was administered by IV injection, blood collected, animals perfused, brains removed, levels of $^3$H quantified and % change in $^3$H-nicotine in brains relative to control animals was determined.

Figure 17:
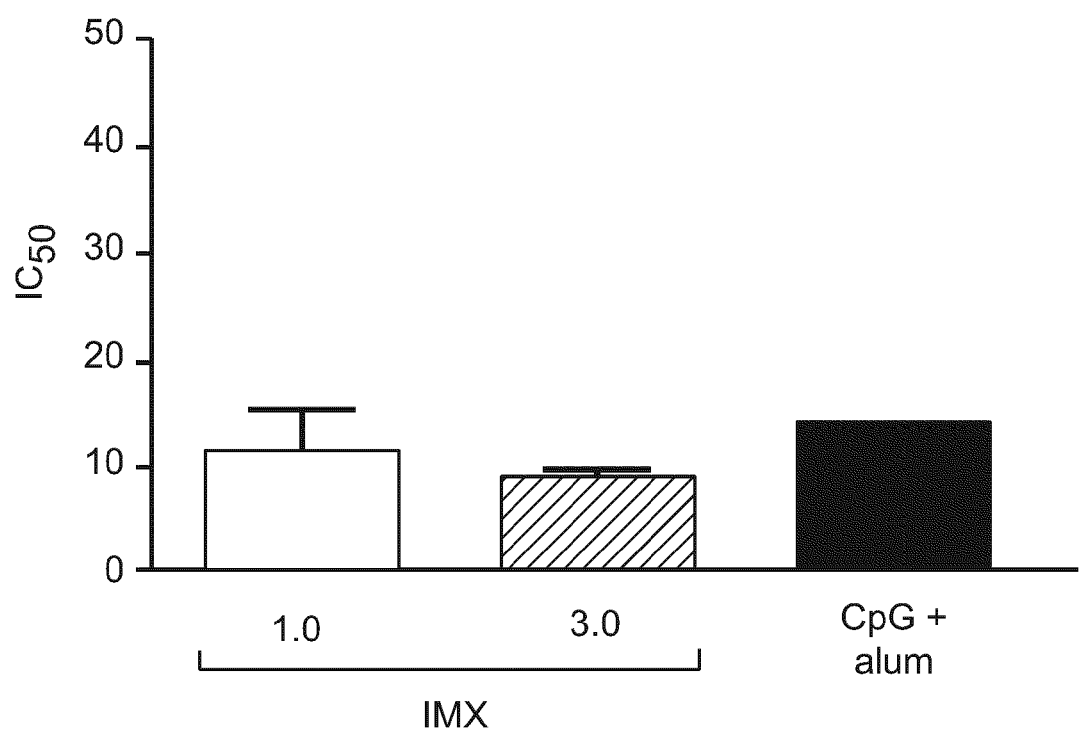
Figure 18:
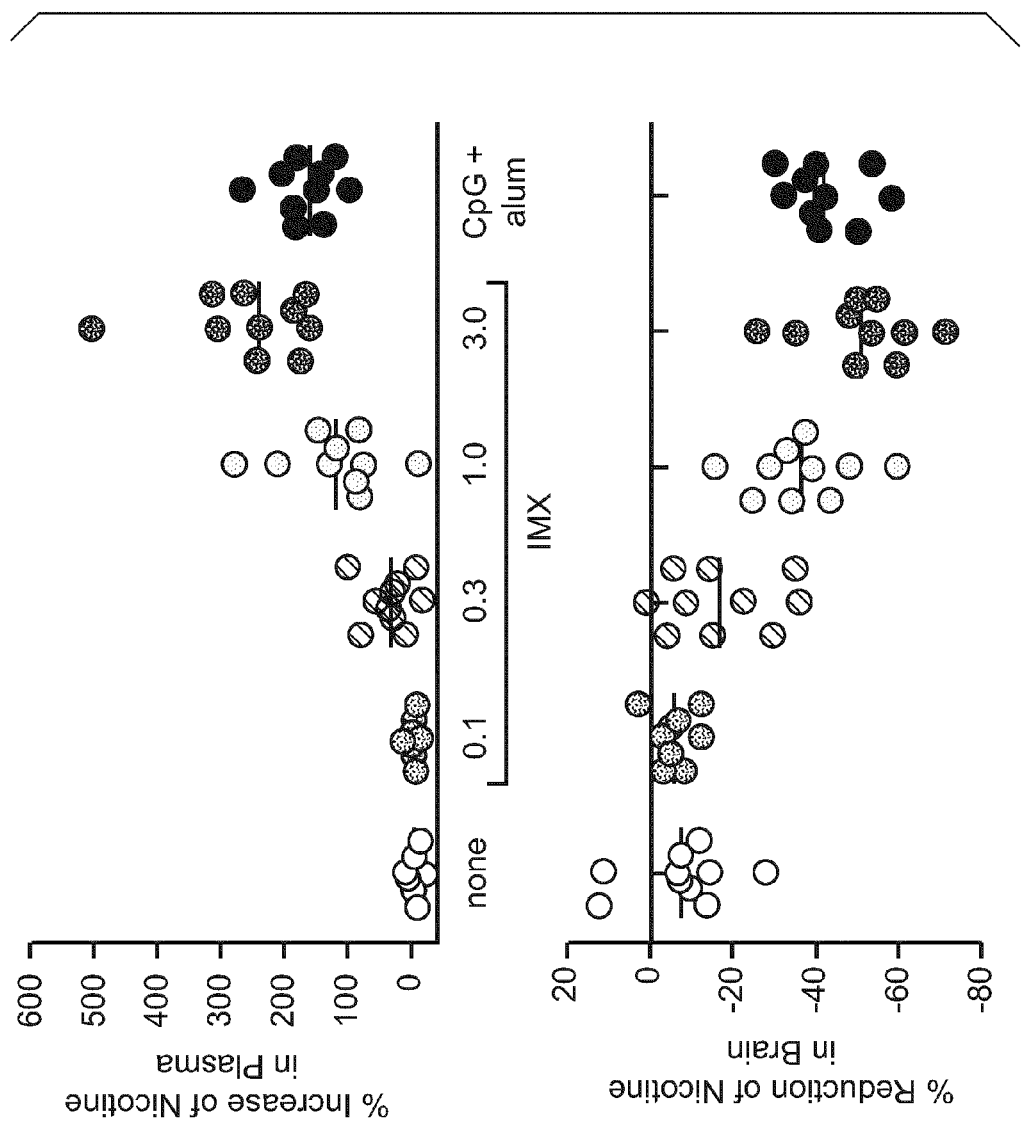

FIGS. 16-18 show the effect of immunization of mice with anti-nicotine vaccines on anti-nicotine antibody levels and avidity in plasma at various time points. BALB/c mice (n=10 per group) were immunized with nicotine-derived hapten (Preparation 12; 5'aminoethoxy nicotine) conjugated to $CRM_{197}$ (10 μg) by intra-muscular vaccination in the presence of aluminium hydroxide (alum; Alhydrogel-85: 40 μg $Al^{3+}$) and CpG 24555 (50 μg), or in the presence of ISCOMATRIX (IMX; 0.1 to 3.0 Units). Anti-nicotine antibody levels (total IgG) in plasma were measured by ELISA (day 21 and 28) and avidity was measured by inhibition ELISA. FIG. 16 [i] shows results 3 weeks post $1^{st}$ dose; and [ii] shows results 1 week post $2^{nd}$ does. FIG. 17 shows avidity ($IC_{50}$) 1 week post $2^{nd}$ dose. FIG. 18 shows sequestration of nicotine in plasma (top); and uptake of nicotine into brain (bottom).

Figure 19:
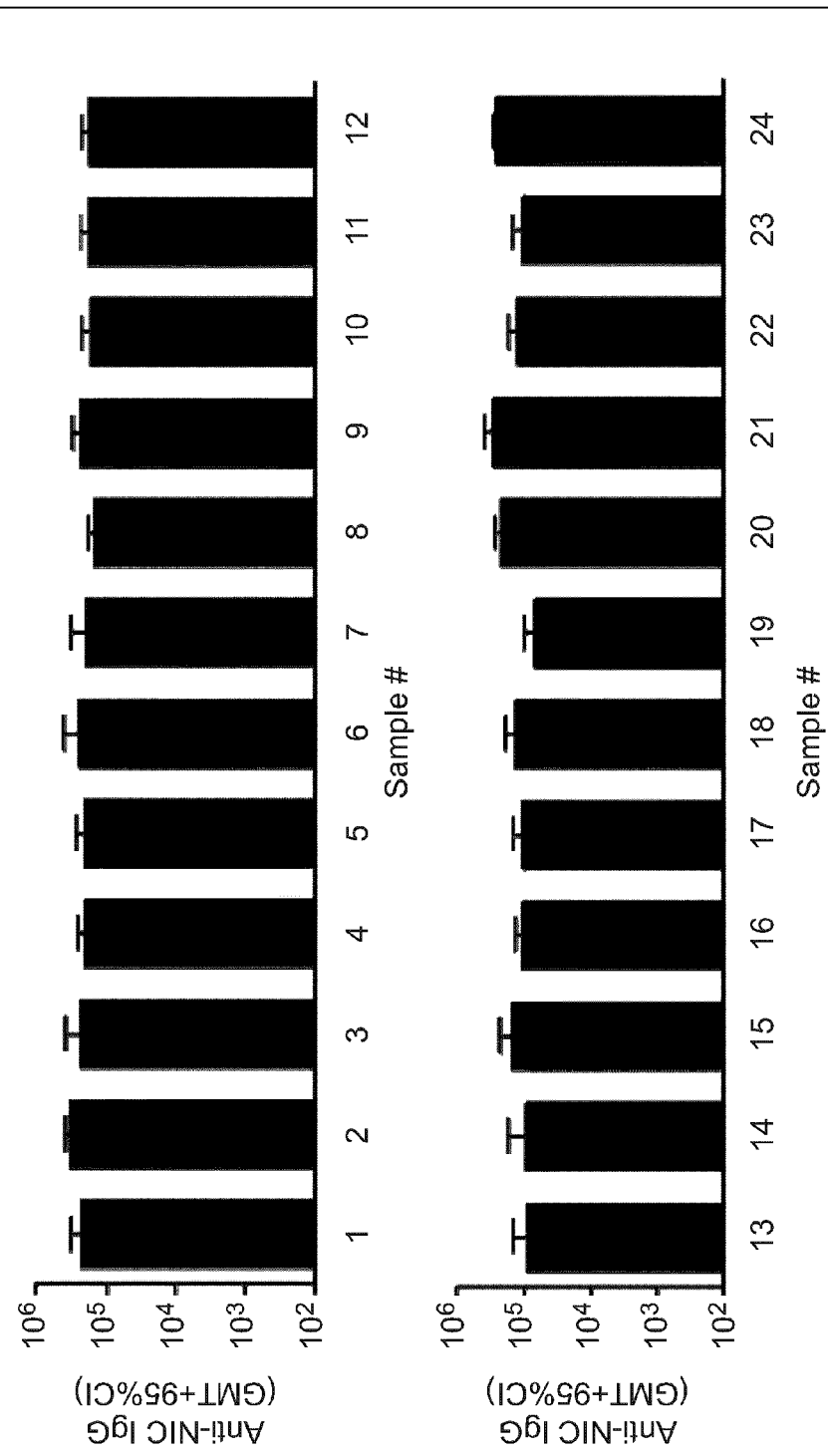
Figure 20:
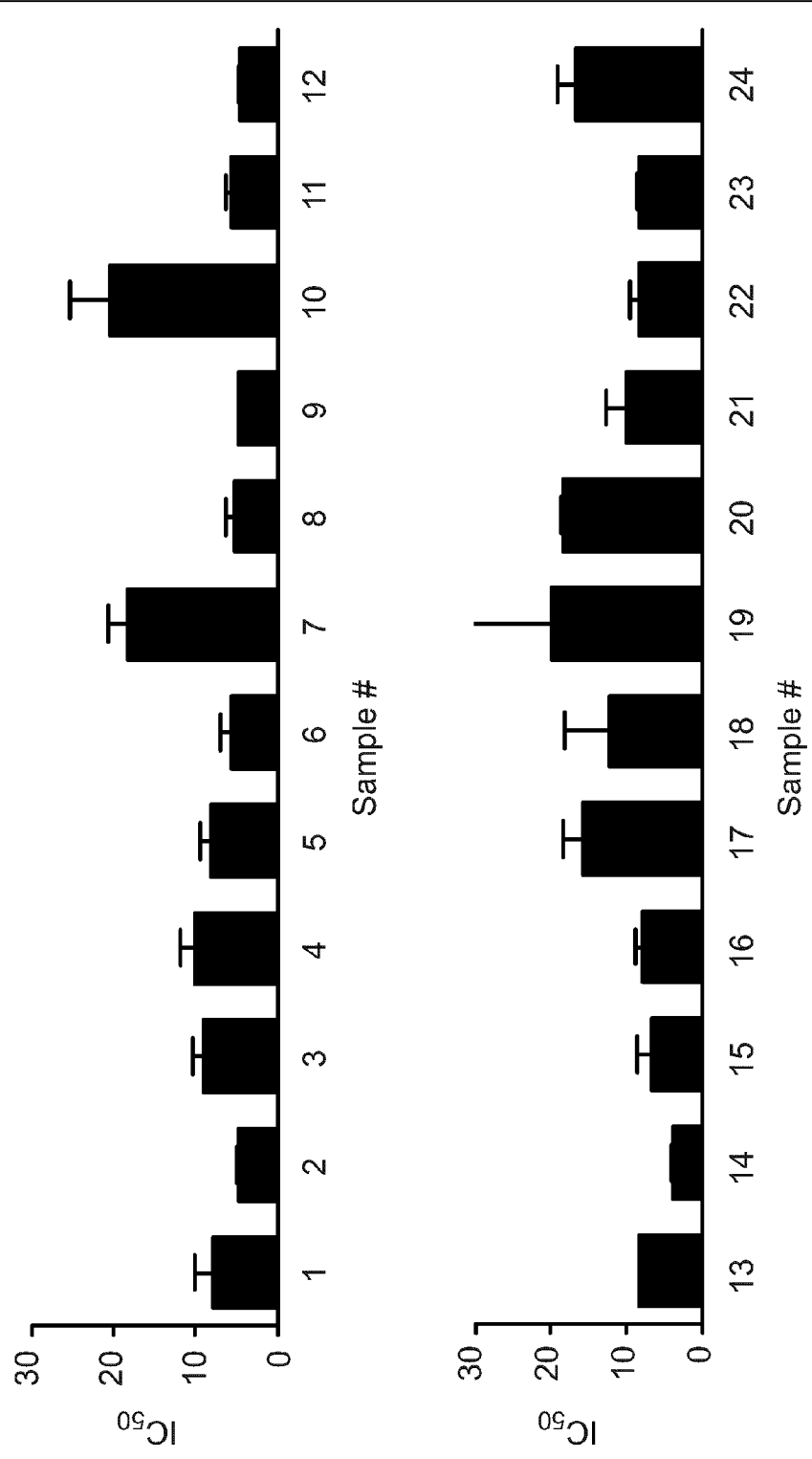

FIGS. 19 and 20 show the effect of conjugation conditions of the nicotine-derived hapten-carrier conjugates of Table 6 on anti-nicotine antibody levels and corresponding $IC_{50}$ values. BALB/c mice (n=10 per group) were immunized with the nicotine-derived hapten by intra-muscular vaccination in the presence of aluminium hydroxide (alum; Alhydrogel-85: 40 μg $Al^{3+}$) and CpG 24555 (50 μg). Anti-nicotine antibody levels (total IgG) in plasma were measured by ELISA and avidity was measured by inhibition ELISA.

Figure 21:
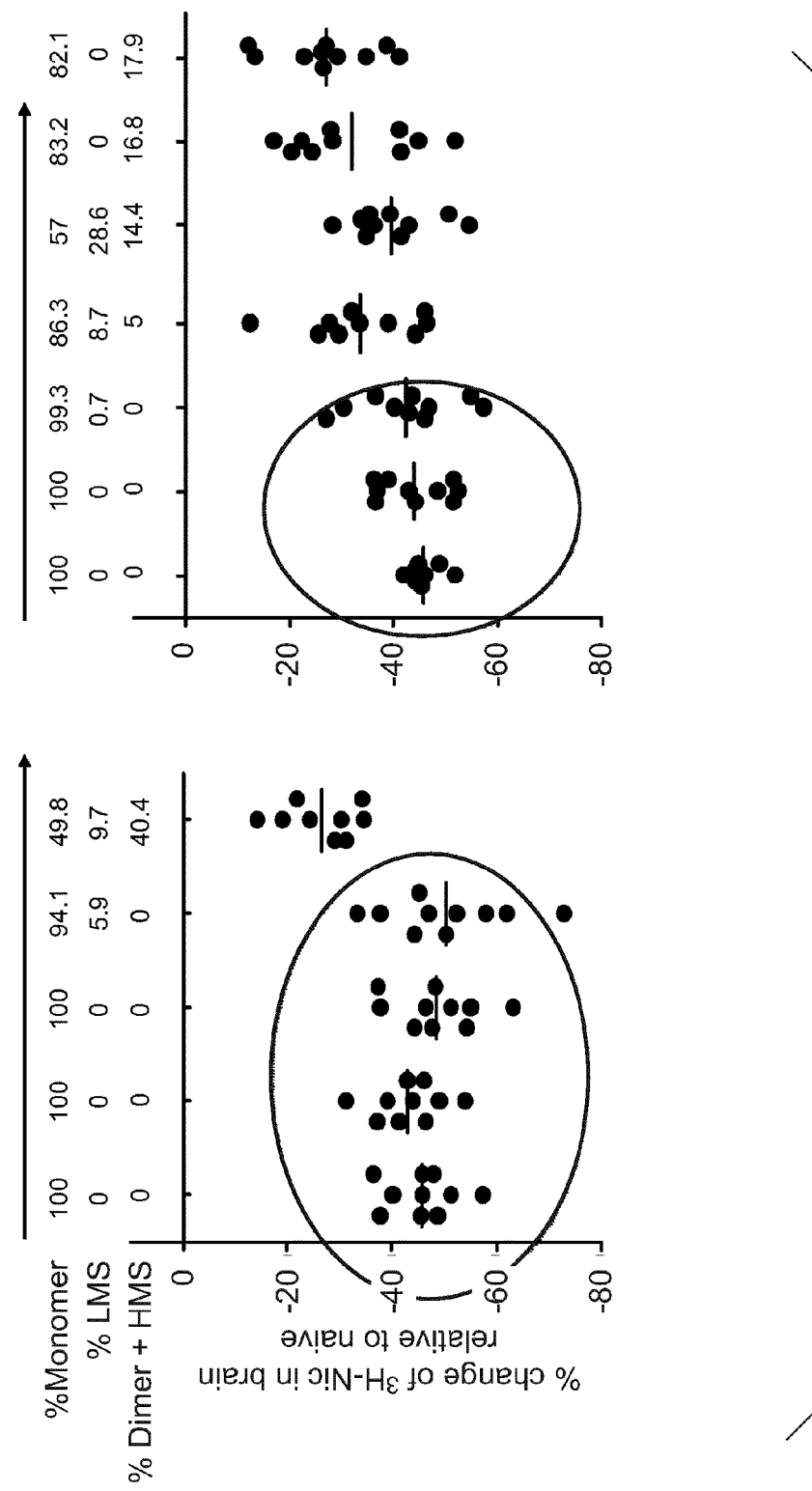
Figure 22:
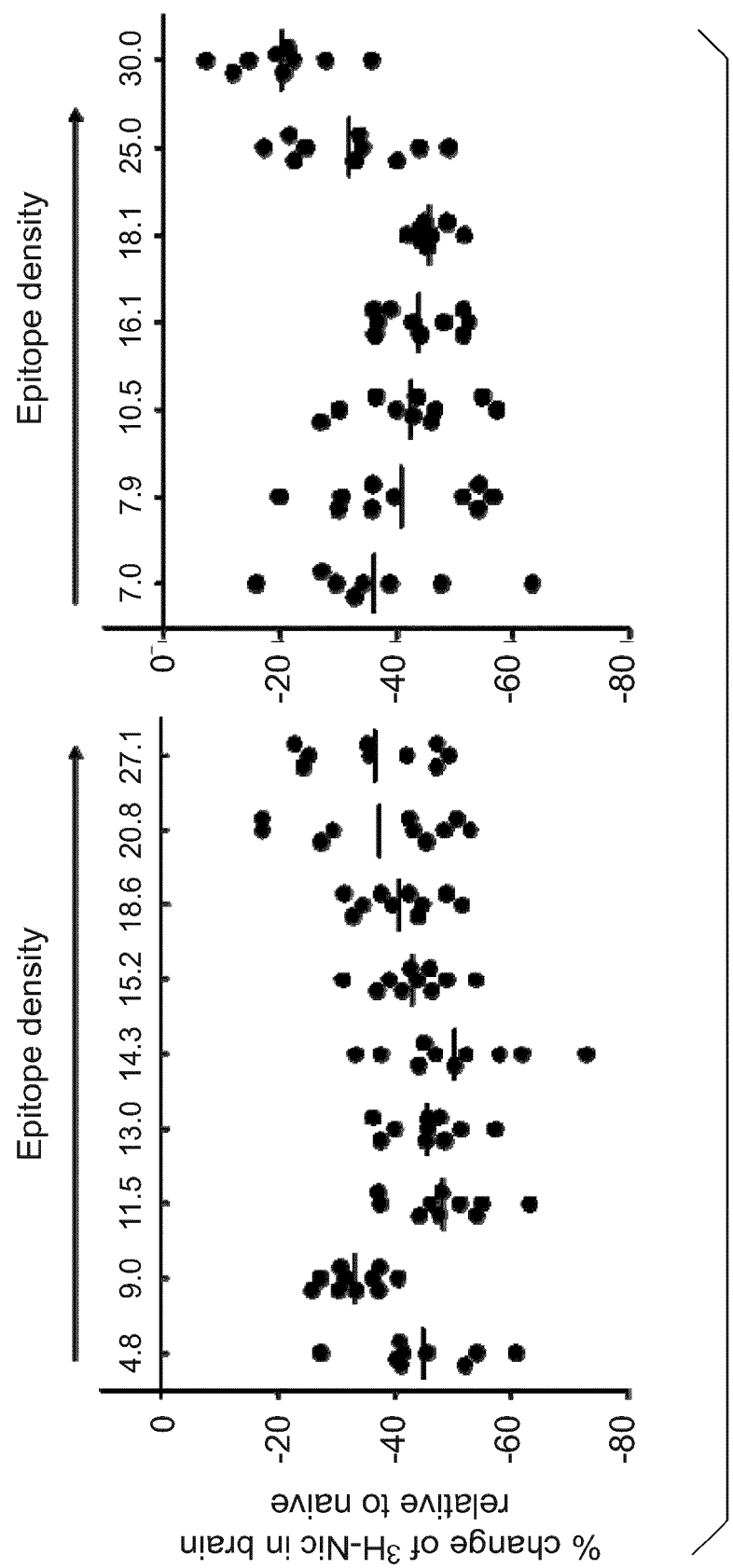

FIGS. 21 and 22 show distribution of $^3$H-nicotine in blood and brain for the hapten-carrier conjugates of Table 6. BALB/c mice (n=10 per group) were immunized with the nicotine-derived hapten by intra-muscular vaccination in the presence of aluminium hydroxide (alum; Alhydrogel-85: 40 μg $Al^{3+}$) and CpG 24555 (50 μg). At one week post the second immunization, $^3$H-nicotine (0.05 mg/kg nicotine containing 3 μCi $^3$H-nic) was administered by IV injection, blood collected, animals perfused, brains removed, levels of $^3$H quantified and % change in $^3$H-nicotine in blood and brains relative to control animals was determined.

Figure 23:
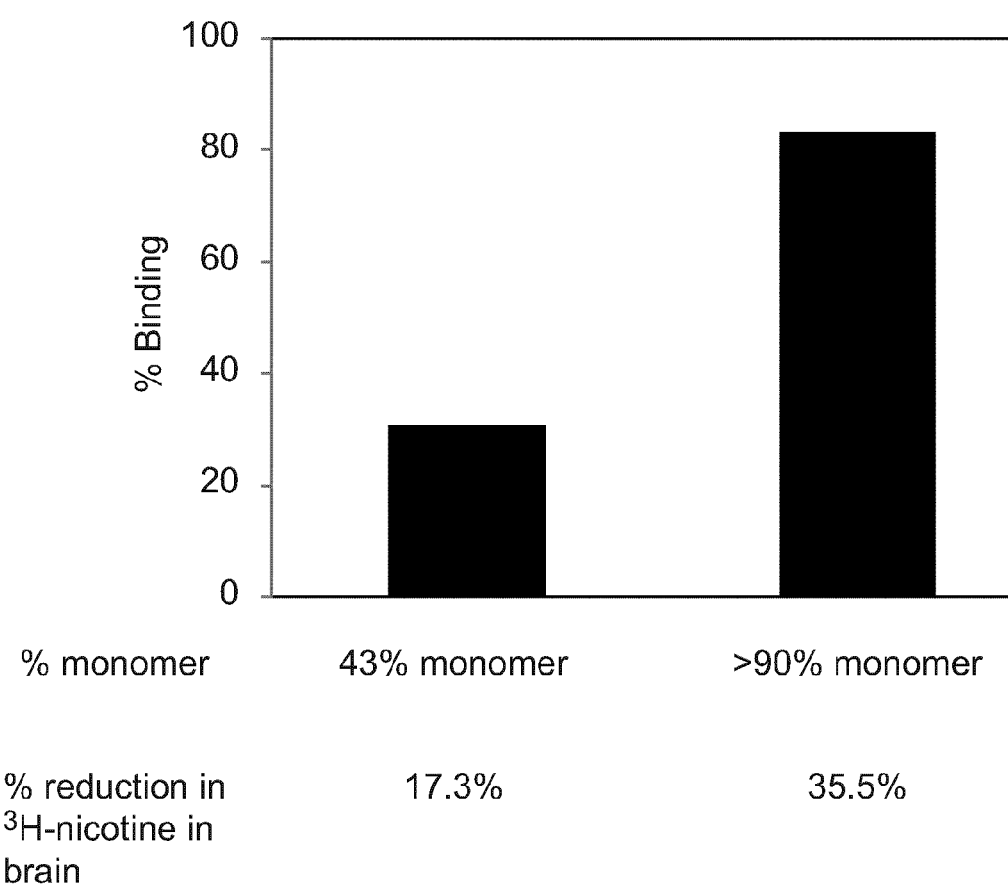

FIG. 23 shows the results of testing for binding of the hapten-carrier conjugates with differing percent monomeric carrier protein to CpG/Alhydrogel. Binding was determined by incubating CpG/Alhydrogel with a known amount of hapten-carrier conjugate and then measuring the concentration of conjugate left in solution after incubation. The % decrease in concentration of conjugate is equivalent to % conjugate binding to the CpG/Alhydrogel. BALB/c mice (n=10 per group) were immunized with 10 μg of different conjugates by intra-muscular injection in the presence of aluminium hydroxide (alum; Alhydrogel-85: 40 μg $Al^{3+}$) and 10 μg CpG 24555. At one week post the second immunization, $^3$H-nicotine (0.05 mg/kg nicotine containing 3 μCi $^3$H-nic) was administered by IV injection, blood collected, animals perfused, brains removed, levels of $^3$H quantified and % change in $^3$H-nicotine in blood and brains relative to control animals was determined.

SEQUENCE LISTING

SEQ ID NO:1 is the nucleotide sequence of immunostimulatory oligonucleotide ODN CpG 24555.

DETAILED DESCRIPTION

In one aspect of the invention relates to a hapten of the formula (I):

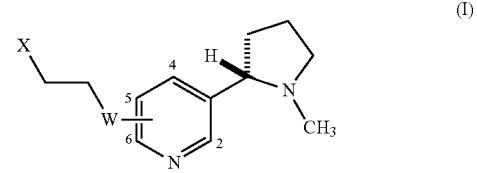

(I)

wherein W is —$CH_2$— or —O—; and X is —$NH_2$ or —SH.

In one embodiment, W is in position 2, 5 or 6 of the pyridine ring.

In another embodiment, W is in position 5 of the pyridine ring.

In another embodiment, W is —O—.

In another embodiment, W is —O—; and W is in position 5 of the pyridine ring.

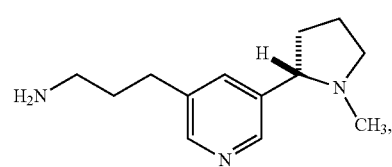

-continued

[Chemical structures of haptens shown]

In a further embodiment, the hapten is
In another embodiment, the hapten is

[Chemical structures shown] or

In a further embodiment, the hapten is

[Chemical structure shown]

In a second aspect, the invention relates to a hapten-spacer conjugate of the formula (II):

[Structure (II) shown]

wherein W is —CH$_2$— or —O—; -(spacer)- is a C$_1$-C$_8$ alkylene group, a C$_3$-C$_{10}$ cycloalkylene group or a C$_1$-C$_{12}$ alkylene group interrupted by 1 to 4 oxygen atoms and optionally interrupted by a —N(H)C(O)—; and X is —NH$_2$ or —SH.

As used herein, an 'alkylene group' is meant a —(CH$_2$)$_n$— group in which n is the required number of carbon atoms. As used herein, an 'alkylene group interrupted by 1 to 4 oxygen atoms' is, for example, —CH$_2$CH$_2$OCH$_2$—, —CH$_2$CH$_2$OCH$_2$CH$_2$OCH$_2$— or —CH$_2$CH$_2$OCH$_2$CH$_2$OCH$_2$CH$_2$OCH$_2$CH$_2$OCH$_2$CH$_2$—.

As used herein, an 'alkylene group interrupted by 1 to 4 oxygen atoms and interrupted by a —N(H)C(O)-' is, for example, —CH$_2$CH$_2$CH$_2$OCH$_2$CH$_2$OCH$_2$CH$_2$OCH$_2$CH$_2$CH$_2$NHCOCH$_2$CH$_2$—.

In one embodiment, W is in position 2, 5 or 6 of the pyridine ring.

In another embodiment, W is in position 5 of the pyridine ring.

In a further embodiment, W is —O—.

In another embodiment, W is —O—; and W is in position 5 of the pyridine ring.

In one embodiment, -(spacer)- is a C$_1$-C$_6$ alkylene group.

In another embodiment, -(spacer)- is a C$_1$-C$_{10}$ alkylene group interrupted by 1 to 4 oxygen atoms.

In yet another embodiment, -(spacer)- is a C$_1$-C$_{12}$ alkylene group interrupted by 3 oxygen atoms and interrupted by a —N(H)C(O)—.

In one embodiment, the hapten-spacer conjugate is

[Structure shown]

The following further embodiments are envisaged:
(i) a hapten-spacer conjugate of formula (II) as described above, wherein W is —O—;
(ii) a hapten-spacer conjugate of formula (II) as described above, wherein W is —CH$_2$—;
(iii) a hapten-spacer conjugate of formula (II) as described above or in embodiments (i) and (ii), wherein X is —SH.
(iv) a hapten-spacer conjugate of formula (II) as described above or in embodiments (i) to (iii), wherein W is in position 2, 5 or 6 of the pyridine ring;
(v) a hapten-spacer conjugate of formula (II) as described above or in embodiments (i) to (iv), wherein W is in the 5 position of the pyridine ring;
(vi) a hapten-spacer conjugate of formula (II) as described above or in embodiments (i) to (v), wherein -(spacer)- is a C$_1$-C$_8$ alkylene group, a C$_6$ cycloalkylene group, or a C$_1$-C$_{12}$ alkylene group interrupted by 1 to 4 oxygen atoms and optionally interrupted by —N(H)C(O)—; and
(vii) a hapten-spacer conjugate of formula (II) as described above or in embodiments (i) to (vi), wherein -(spacer)- is a C$_1$-C$_8$ alkylene group.

In the following schemes, which depict general methods for obtaining the compounds of formula (I), the substituents are as defined above for the compounds of formula (I) or derivatives thereof, unless otherwise stated:

Scheme 1

[Structure (i) shown]

-continued

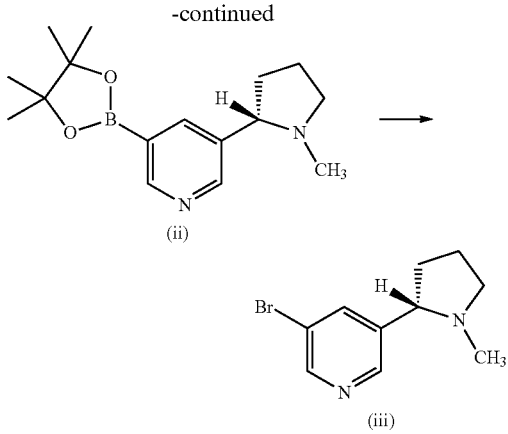

Boronate ester (ii) can be formed from the reaction of (S)-(−)-nicotine (i) with a suitable iridium catalyst, typically methoxy(cyclooctadiene)iridium(I) dimer, a ligand, such as 4,4'-di-tert-butyl-2,2'-dipyridyl, and a boron source, such as bis(pinacolato)diboron or 4,4,5,5-tetramethyl-1,3,2-dioxaborolane, in a suitable solvent, such as 1,4-dioxane or THF, at a temperature between room temperature and reflux. Boronate ester (ii) can then be converted to bromide (iii) using copper (II) bromide in a suitable solvent system, such as methanol/water or ethanol/water, at a temperature of, typically, between 60° C. and reflux.

under a hydrogen atmosphere in a suitable solvent, such as methanol, ethanol or ethyl acetate, at a temperature typically around room temperature.

Reduction of nitrile (v) to amine (vi) is typically carried out using a suitable catalyst, such as Raney Nickel, under a hydrogen atmosphere (typically around 50-100 psi pressure) in a suitable solvent, such as methanol or ethanol, in the presence of concentrated ammonia, at a temperature of typically around 40-70° C.

The formation of amides of type (viii) can be carried out under standard literature conditions. The acid (vii) can be converted to an acid chloride using a suitable chlorinating agent, such as oxalyl chloride or thionyl chloride, in a suitable solvent, such as dichloromethane or toluene, optionally in the presence of catalytic DMF, at a suitable temperature, typically between 0° C. and room temperature. The acid chloride can then be reacted with the amine (vi) in the presence of a base, such as triethylamine or diisopropylethylamine, in a suitable solvent, such as dichloromethane or toluene, at a temperature of between 0° C. and room temperature. Alternatively the acid (vii) can be converted to a suitable activated species with a coupling agent, such as $T_3P$, EDCl.HCl, EDCl.MeI, HBTU, HATU, PyBop, DCC, or CU, in a suitable solvent, such as dichloromethane or DMF. In the presence of EDCl.HCl or EDCl.MeI, HOBT is optionally added. A suitable base, such as triethylamine or diisopropylethylamine, is

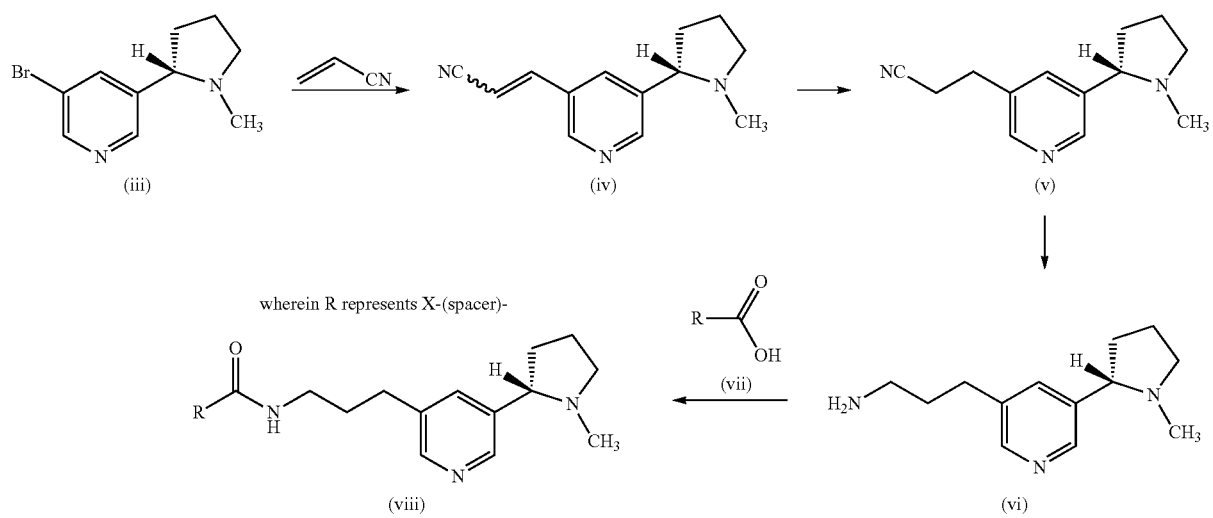

Bromide (iii) can then be converted to unsaturated cyanide (iv) with acrylonitrile, under palladium coupling conditions, using a suitable palladium source, such as palladium (II) acetate or tetrakis(triphenylphosphine)palladium, in the presence of a suitable phosphine ligand, such as tri(o-tolyl)phosphine or trifurylphosphine, in the presence of a suitable base, such as sodium carbonate, triethylamine or N-diisopropylethylamine, in a suitable solvent, such as acetonitrile or 1,4-dioxane, at a temperature, typically, around reflux.

Hydrogenation of (iv) to give (v) is typically carried out using a suitable catalyst, such as palladium on carbon, palladium hydroxide on carbon or platinum on activated charcoal, also used and the reaction is typically carried out at room temperature.

Scheme 3

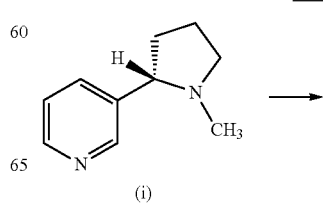

-continued

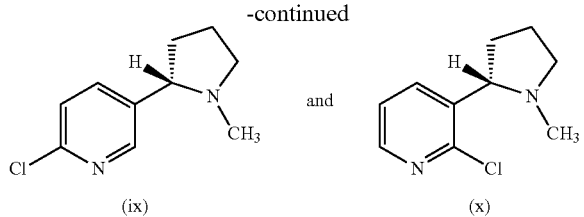

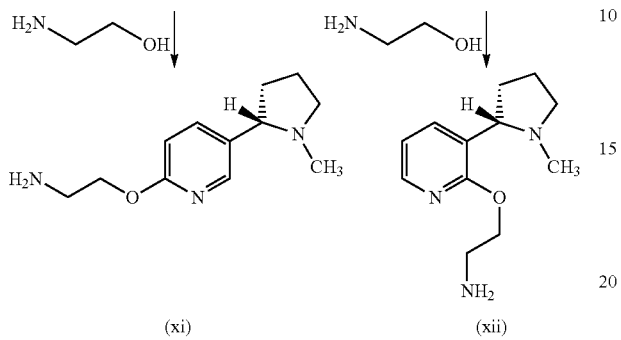

Deprotonation of (i) can be carried out with a suitable base, such as the super-base nBuLi-LiDMAE (formed by reaction of n-butyllithium with dimethylaminoethanol), in a suitable solvent, such as hexane, toluene, hexane/toluene or hexane/THF, at a suitable temperature, typically of between −78° C. and 0° C. The resulting anion can be quenched with a suitable chlorine source, such as hexachloroethane or N-chlorosuccinimide, at a temperature of between −78° C. and room temperature, to give the two chloropyridine analogues (ix) and (x).

Chloropyridine analogues (ix) and (x) can be converted to amines (xi) and (xii) using ethanolamine, preferably as solvent and reactant, and using a suitable strong base, such as sodium hydride or potassium tert-butoxide, at a temperature of typically between 50-100° C.

Scheme 4

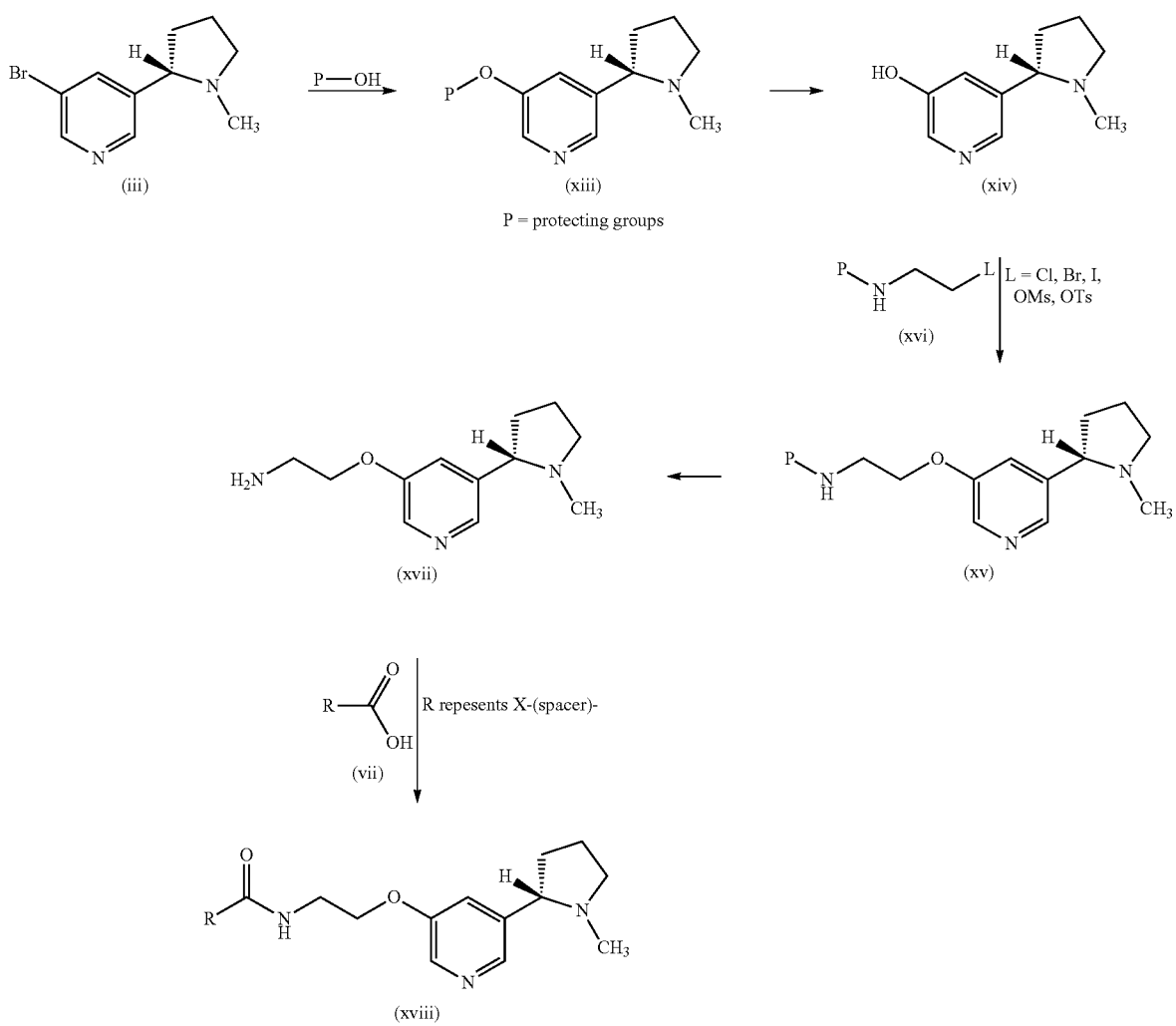

Bromide (iii) can be reacted with a protecting group carrying alcohol (for example benzyl alcohol or, preferably, p-methoxybenzylalcohol) using a suitable base, typically sodium hydride, in a suitable solvent, such as DMF or NMP, at a temperature of typically around 90-130° C. Removal of the protecting group to give (xiv) can be carried out using standard literature methods (for example, for the p-methoxybenzylalcohol, a suitable acid such as trifluoroacetic acid can be used).

Alcohol (xiv) can be converted to protected amine (xv) (the protecting group is preferably BOC) using a suitable alkylating agent (xvi), such as a halide, mesylate or tosylate, and a base, such as potassium carbonate or caesium carbonate, in a suitable solvent, such as acetonitrile or DMF, at a temperature of typically between 80° C. and reflux. Deprotection of the amine can be carried out, using standard literature methods, to give (xvii) (for example, for the case of the BOO protecting group, the deprotection can be carried out using a suitable acid source such as trifluoroacetic acid or hydrogen chloride in a suitable solvent such as 1,4-dioxane, THF or dichloromethane).

Formation of amides of type (xviii) can be carried out under standard literature conditions. The acid (vii) can be converted to an acid chloride using a suitable chlorinating agent, such as oxalyl chloride or thionyl chloride, in a suitable solvent, such as dichloromethane or toluene, optionally in the presence of catalytic DMF, at a suitable temperature, typically of between 0° C. and room temperature. The acid chloride can then be reacted with the amine (xvii) in the presence of a base, such as triethylamine or diisopropylethylamine, in a suitable solvent, such as dichloromethane or toluene, at a temperature of between 0° C. and room temperature. Alternatively the acid (vii) can be converted to a suitable activated species with a coupling agent, such as $T_3P$, EDCl.HCl, EDCl.MeI, HBTU, HATU, PyBop, DCC, or CU, in a suitable solvent, such as dichloromethane or DMF. In the presence of EDCl.HCl or EDCl.MeI, HOBT is optionally added. A suitable base, such as triethylamine or diisopropylethylamine, is also used and the reaction is typically carried out at room temperature. Alternatively, the amine (xvii) can be reacted with acid anhydrides or lactones to prepare further derivatives of general structure (xviii). For example, g-butyrolactone or g-thiobutyrolactone can be used as the acyl source in this step, or for example an anhydride such as succinic or phthalic anhydride to provide derivatives (xviii).

Scheme 5

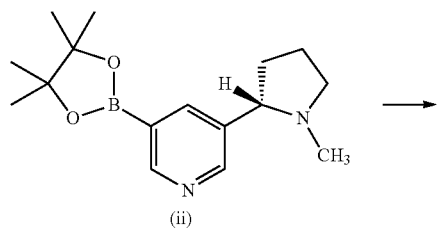

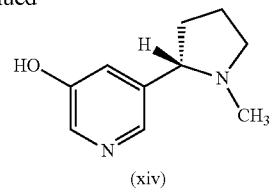

Alcohol (xiv) can also be prepared via boronate ester (ii) using a suitable oxidising agent, typically hydrogen peroxide, and a suitable acid, such as acetic acid, in a suitable solvent, such as THF or 1,4-dioxane.

In a third aspect, the invention relates to a hapten-carrier conjugate of formula (III):

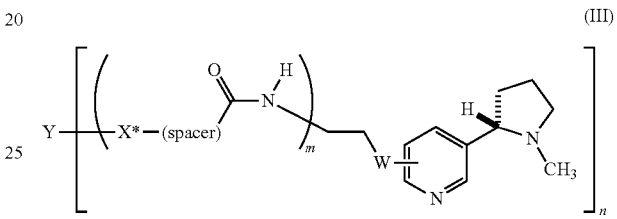

wherein W is —$CH_2$— or —O—; -(spacer)- is a $C_1$-$C_8$ alkylene group, a $C_1$-$C_{12}$ alkylene group interrupted by 1 to 4 oxygen atoms and optionally interrupted by —N(H)C(O)—, or a $C_3$-$C_{10}$ cycloalkylene group; m is 0 or 1; X* is —N(H)— or —S—; n is an integer from 1 to 1000; and Y is an optionally modified carrier protein selected from bacterial toxoids, immunogenic substances, viruses, virus-like particles, protein complexes, proteins, polypeptides, liposomes and immuno-stimulating complexes.

In certain embodiments, Y is a diphtheria toxoid or $CRM_{197}$.

For attachment of the haptens to the carrier proteins, the following methods are illustrative. The carrier protein, such as diphtheria toxoid (DT) or $CRM_{197}$, for example, can be activated by treatment with an anhydride, for example succinic anhydride, to produce a derivatized version of the carrier protein (xix). This derivative can then be coupled to a hapten (xvii) in the presence of a standard coupling reagent by conversion to a suitable activated species with, for example, $T_3P$, EDCl.HCl, EDCl.MeI, HBTU, HATU, PyBop, DCC, or CU, in a suitable solvent or buffer (such as Dulbeccos' Phosphate Buffered Saline). In the presence of EDCl.HCl or EDCl.MeI, HOBT or N-hydroxysuccinimide (or sulfated versions thereof) is optionally added and the reaction is typically carried out at room temperature to provide the conjugates (xx). Alternatively, the succinylation/derivatization step may be omitted, and direct coupling of the hapten to free carboxyl groups on the carrier protein can be carried out using the above methods to provide the conjugates (xxiv). Alternatively, the carrier protein may be treated with an alternative derivatizing reagent such as bromoacetic acid N-hydroxysuccinimide to give a derivatized species (xxi), which may be treated with a thiol-containing hapten (xxii) to provide the conjugate (xxiii).

Scheme 6

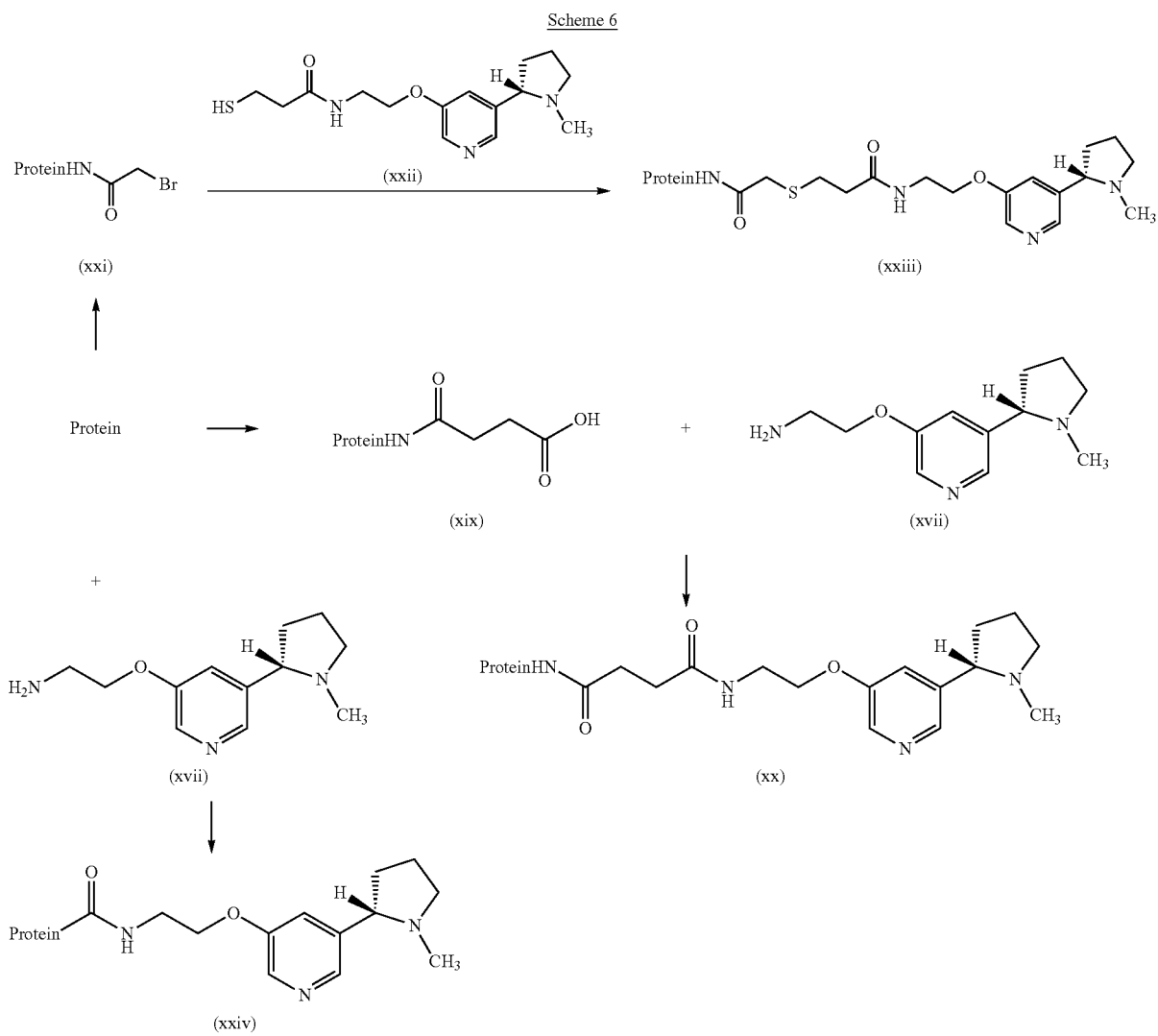

The following embodiments are envisaged:

(i) a hapten-carrier conjugate of formula (III) as described above, wherein W is —O—;
(ii) a hapten-carrier conjugate of formula (III) as described above, wherein W is —CH$_2$—;
(iii) a hapten-carrier conjugate of formula (III) as described above or in embodiments (i) and (ii), wherein W is in position 2, 5 or 6 of the pyridine ring;
(iv) a hapten-carrier conjugate of formula (III) as described above or in embodiments (i) to (iii), wherein W is in the 5 position of the pyridine ring;
(v) a hapten-carrier conjugate of formula (III) as described above or in embodiments
(i) to (iv), wherein -(spacer)- is a $C_1$-$C_8$ alkylene group, a $C_6$ cycloalkylene group or a $C_1$-$C_{12}$ alkylene group interrupted by 1 to 4 oxygen atoms and optionally interrupted by —N(H)C(O)—;
(vi) a hapten-carrier conjugate of formula (III) as described above or in embodiments (i) to (iv), wherein -(spacer)- is $C_1$-$C_8$ alkylene;
(vii) a hapten-carrier conjugate of formula (III) as described above or according to embodiments (i) to (vi), wherein m is 0;

(viii) a hapten-carrier conjugate of formula (III) as described above or according to embodiments (i) to (vii), wherein the carrier is an optionally modified protein selected from tetanus toxoid, diphtheria toxoid or derivatives thereof such as non-toxic mutant diphtheria toxoid CRM$_{197}$, keyhole limpet hemocyanin (KLH), hemocyanine, albumin, outer membrane protein complex (OMPC) from *Neisseria meningitidis*, the B subunit of heat-labile *Escherichia coli*, recombinant exoprotein A from *Pseudomonas aeruginosa* (rEPA) and virus-like particles such as those assembled from recombinant coat protein of bacteriophage Qb;
(ix) a hapten-carrier conjugate of formula (III) as described above or according to embodiments (i) to (viii), wherein the carrier is a protein selected from diphtheria toxoid and CRM$_{197}$, which are optionally modified;
(x) a hapten-carrier conjugate of formula (III) as described above or according to embodiments (i) to (ix), wherein the carrier is optionally modified CRM$_{197}$;
(xi) a hapten-carrier conjugate of formula (III) as described above or according to embodiments (i) to (x), wherein n is an integer in the range of 1 to 40;
(xii) a hapten-carrier conjugate of formula (III) as described above or according to embodiments (i) to (x), wherein n is an integer in the range of 10 to 18;

(xiii) a hapten-carrier conjugate of formula (III) as described above or according to embodiments (i) to (xii) or as described above, wherein the carrier protein is a modified succinylated protein.

Diphtheria toxin is converted to diphtheria toxoid by incubation at 37° C. in the presence of formaldehyde and other excipients for between 4 to 6 weeks. This treatment creates a highly cross-linked protein of heterogeneous molecular weight that renders the protein non-toxic but retains its immunogenicity. The use of this protein as a vaccine carrier protein is well documented, and has been used as an anti-gonadotrophin releasing factor (GnRF) vaccine for pigs, as an alternative to surgical castration (Improvac™, Pfizer). It is also commercially available in an unconjugated form as a human vaccine against diphtheria as part of the DTaP vaccine to treat diphtheria, tetanus and acellular pertussis respectively.

$CRM_{197}$ is a genetically detoxified version of diphtheria toxin, rendered non-toxic by a single point mutation of a glycine residue at position 52 for a glutamic acid residue. The mutation removes the ability of the protein to bind to NAD+, and as such, the protein is enzymatically inactive. Due to the absence of cross-linking, the protein is a more homogenous molecular weight product than diphtheria toxoid, a formaldehyde inactivated preparation of diphtheria toxin. $CRM_{197}$ has also been used as a carrier protein for the commercially available anti-pneumococcal vaccine treatment (Prevnar®, Pfizer).

In a fourth aspect, the invention relates to a method of making nicotine-derived hapten-carrier conjugates as described above, comprising coupling an optionally modified carrier protein with a nicotine-derived hapten of formula (I) or a hapten-spacer conjugate of formula (II), as described above.

In certain embodiments, the attachment of the haptens to the carrier proteins can be done in a way which minimizes the number of carrier proteins which are linked together. In certain embodiments, the number of carrier proteins linked together is less than 5%, less than 10%, less than 15%, less than 20%, less than 25% or less than 30% of the total number of carrier proteins.

In a preferred embodiment, the invention relates to a method of making a nicotine-derived hapten carrier conjugate of formula (III), as described above, wherein X* is —NH—, comprising treating an optionally modified carrier protein with sulfo-N-hydroxysuccinimide, followed by 1-ethyl-3-(3-dimethylaminopropyl) carbodiimide hydrochloride, then adding a hapten of formula (I) or a hapten-spacer conjugate of formula (II), as described above, wherein X is —$NH_2$.

In an alternative embodiment, the invention relates to a method of making a hapten carrier conjugate of formula (III) as described above, wherein X* is —NH—, comprising treating the carrier protein with succinic anhydride to give a modified succinylated carrier protein; treating the modified succinylated carrier protein with sulfo-N-hydroxysuccinimide, followed by 1-ethyl-3-(3-dimethylaminopropyl) carbodiimide hydrochloride, then adding a hapten of formula (I) or a hapten-spacer conjugate of formula (II), as described above, wherein X is —$NH_2$.

In an alternative embodiment, the invention relates to a method of making a hapten carrier conjugate of formula (III), as described above, wherein X* is —S—, comprising treating the carrier protein with bromoacetic acid N-hydroxysuccinimide ester, then adding a hapten of formula (I) or a hapten-spacer conjugate of formula (II), as described above, wherein X is —SH.

In a fifth aspect, the invention relates to vaccines (or vaccine compositions) comprising a plurality of hapten-carrier conjugates of formula (III), as defined above, and one or more adjuvants.

Examples of suitable adjuvants are those known to enhance antibody responses to antigens, including the antibody responses against the nicotine hapten when it is coupled to a carrier molecule. Adjuvants are well known in the art (J. C. Aguilar, E. G. Rodriguez, Review: Vaccine Adjuvants Revisited, 2007, Vaccine, 25, 3752-3762). The adjuvant may act by one or more mechanisms including direct innate immune activation, creating a depot, or acting as a delivery vehicle for the antigen. The adjuvant that acts by direct innate immune activation may be an agonist for a Toll-like receptor (TLR) including, but not limited to, stabilized poly I:C that activates TLR3, a derivative of lipopolysaccharide such as monophosphoryl-lipid A (MPL) or Glycopyranosyl Lipid Adjuvant (GLA) that activate via TLR4, flagellin that activates via TLR5, small molecules of the imidazoquinoline family such as Imiquimod or resiquimod that activate via TLR7 or TLR8 or both TLR7 and TLR8, oligoribonucleotides (ORN) that activate via TLR7 and/or TLR8, and oligodeoxynucleotides (ODN) containing CpG motifs that activate via TLR9. The CpG ODN TLR9 agonists may be of the A-Class, B-Class, C-Class or P-Class, with or without halogenation of the 5'T known as an E modification, and may be made with a wholly phosphodiester backbone, a wholly phosphorothioate backbone, a chimeric backbone, a "semi-soft" backbone that is wholly phosphorothioate except between the cytosines and guanosines of the CpG motif. The adjuvant that acts by direct innate immune activation may act through a non-TLR mechanism, such as QS21 or other saponins.

The adjuvant may be an aluminium salt that act as both a depot system as well as an innate immune activator via the inflammasome. The aluminium salt is preferentially selected from aluminium hydroxide or aluminium phosphate. The aluminium hydroxide is preferentially Alhydrogel original or Alhydrogel'85.

The adjuvant that acts through both immune activation and delivery vehicle may be an immune stimulatory complex (ISCOM) such as ISCOMATRIX.

The adjuvant that has delivery vehicle properties may be macromolecular complexes, nanocapsules, nanoparticles, microspheres, microparticles, or virosomes and these may have moieties on their surfaces for the purpose of targeting to specific cell types. The adjuvant may be a lipid-based system including oil-in-water emulsions, water-in-oil emulsions, micelles, mixed micelles, and liposomes. Liposomes may be unilamellar or multilamellar. The emulsion may be squalene based such as MF-59.

The adjuvant may be a virosome.

Preferred adjuvants are selected from CpG oligodeoxynucleotides (CpG ODN), aluminium salts, QS21 and ISCOMS.

Preferred CpG ODN are of the B Class that preferentially activate B cells. In aspects of the invention, the CpG ODN has the nucleic acid sequence 5' T*C*G*T*C*G*T*T*T*T*T*C*G*G*T*G*C*T*T*T*T 3' (SEQ ID NO:1) wherein * indicates a phosphorothioate linkage. The CpG ODN of this sequence is known as CpG 24555.

As used herein, the term "oligodeoxynucleotide" (ODN) means multiple nucleotides (i.e., molecules comprising a deoxyribose sugar linked to a phosphate group and to an exchangeable organic base, which is either a substituted pyrimidine (e.g., cytosine (C) or thymidine (T)) or a substituted purine (e.g., adenine (A) or guanine (G)). Nucleic acid molecules can be obtained from existing nucleic acid sources (e.g., genomic or cDNA), but are preferably synthetic (e.g., produced by nucleic acid synthesis). Oligonucleotides having phosphorothioate linkages are relatively resistant to degradation in vivo (e.g., via endo- and exo-nucleases), providing enhanced activity in vivo.

Methods for synthesis and chemical modification of oligonucleotides are known to the skilled person and are described, for example in Uhlmann E. et al. (1990), Chem. Rev. 90:543; "Protocols for Oligonucleotides and Analogs" Synthesis and Properties & Synthesis and Analytical Techniques, S. Agrawal, Ed., Humana Press, Totowa, USA 1993; Crooke, S. T. et al. (1996) Annu. Rev. Pharmacol. Toxicol. 36:107-129; and Hunziker J. et al., (1995), Mod. Synth. Methods 7:331-417. The oligonucleotides of the invention can be synthesized de novo using any of a number of procedures well known in the art. For example, the b-cyanoethyl phosphoramidite method (Beaucage, S. L., and Caruthers, M. H., (1981) Tet. Let. 22:1859); nucleoside H-phosphonate method (Garegg et al., (1986) Tet. Let. 27:4051-4054; Froehler et al., (1986) Nucl. Acid Res. 14:5399-5407; Garegg et al., (1986) 27:4055-4058; Gaffney et al., (1988) Tet. Let. 29:2619-2622). These chemistries can be performed by a variety of automated nucleic acid synthesizers available in the market. These oligonucleotides are referred to as synthetic oligonucleotides. Modified backbones such as phosphorothioates may be synthesized using automated techniques employing either phosphoramidate or H-phosphonate chemistries. Aryl- and alkyl-phosphonates can be made, e.g., as described in U.S. Pat. No. 4,469,863, and alkylphosphotriesters (in which the charged oxygen moiety is alkylated as described in U.S. Pat. No. 5,023,243) can be prepared by automated solid phase synthesis using commercially available reagents. Methods for making other DNA backbone modifications and substitutions have been described (e.g. Uhlmann, E. and Peyman, A., Chem. Rev. 90:544, 1990; Goodchild, J., Bioconjugate Chem. 1:165, 1990).

The most preferred adjuvants are CpG 24555 (as described in co-pending application number PCT/IB2009/055444, hereby incorporated by reference in its entirety) used together with an aluminium hydroxide salt such as Alhydrogel. Thus, in one embodiment there is provided a vaccine (or vaccine composition) comprising a hapten-carrier conjugate of formula (III) as defined above, and CpG 24555. In a further embodiment there is provided a vaccine (or vaccine composition) comprising a hapten-carrier conjugate of formula (III) as described above, CpG 24555 and an aluminium hydroxide salt. In another embodiment there is provided a vaccine (or vaccine composition) comprising CpG 24555 and a plurality of hapten-carrier conjugates of formula (IV):

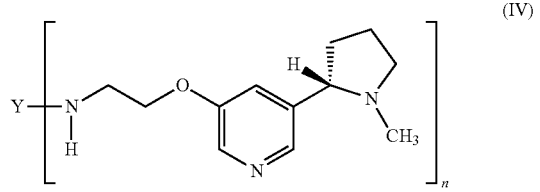

wherein, Y is diphtheria toxoid or $CRM_{197}$ and n is an integer in the range of 1 to 40.

In yet another embodiment there is provided a vaccine (or vaccine composition) comprising CpG 24555, an aluminium hydroxide salt, and a plurality of hapten-carrier conjugates of formula (IV):

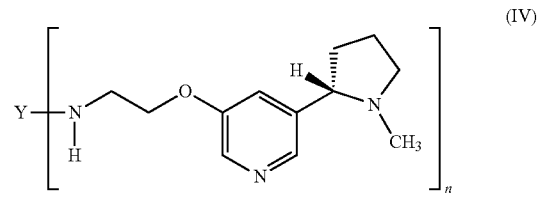

wherein, Y is diphtheria toxoid or $CRM_{197}$ and n is an integer in the range of 1 to 40.

In yet another embodiment there is provided a vaccine (or vaccine composition) comprising an aluminium hydroxide salt (e.g. Alhydrogel), and a plurality of hapten-carrier conjugates of formula (IV):

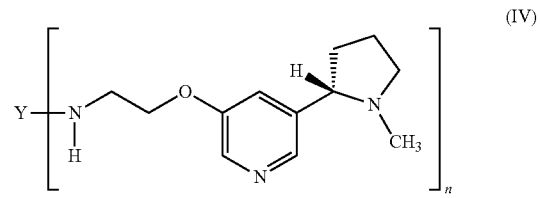

wherein, Y is diphtheria toxoid or $CRM_{197}$ and n is an integer in the range of 1 to 40.

In certain embodiments, n is an integer in the range of 1 to 30 inclusive. In certain embodiments, n is an integer in the rage of 5 to 23 inclusive. In certain embodiments, n is an integer in the range of 10 to 18 inclusive. In certain embodiments, n is 10. In certain embodiments, n is 11. In certain embodiments, n is 12. In certain embodiments, n is 13. In certain embodiments, n is 14. In certain embodiments, n is 15. In certain embodiments, n is 16. In certain embodiments, n is 17. In certain embodiments, n is 18.

By varying the coupling conditions which form the hapten-carrier conjugate, see Exemplification below, the cross-coupling of carrier proteins can be minimized. When carrier proteins cross-couple, the resulting hapten-carrier conjugate comprises multiple carrier proteins covalently or non-covalently bound together and is referred to herein as a "high molecular mass species." In contrast, a "low molecular mass species," as used herein, refers to hapten-carrier conjugates wherein a portion of the carrier protein is lost during the preparation of the conjugate. In certain embodiments it has been observed that high molecular weight species lead to a less effective vaccine. Therefore, in certain embodiments, the present invention relates to any of the aforementioned vaccine compositions wherein less than 5%, less than 10%, less than 15%, less than 20%, less than 25% or less than 30% of the carrier proteins which are a part of the hapten-carrier conjugates are cross-coupled (i.e. are high molecular mass species).

In certain embodiments, the present invention relates to any of the aforementioned vaccine compositions wherein at least 70%, at least 75%, at least 80%, at least 85%, at least 90% or at least 95% of the carrier proteins which are part of the hapten-carrier conjugates are not cross-coupled.

In certain embodiments, more than 70%, more than 75%, more than 80%, more than 85%, more than 90% or more than 95% of the antigenic components of any one of the aforementioned vaccine compositions are hapten-carrier conjugates of formula IV.

In certain embodiments, the present invention relates to any of the aforementioned vaccine compositions wherein at least 70%, at least 75%, at least 80%, at least 85%, at least 90% or at least 95% or the carrier proteins have molecular weights between 50,000 Daltons and 70,000 Daltons. In certain embodiments, the present invention relates to any of the aforementioned vaccine compositions wherein at least 70%, at least 75%, at least 80%, at least 85%, at least 90% or at least 95% or the carrier proteins have molecular weights of about 58,000 Daltons.

The vaccine compositions of the present invention may optionally contain one or more pharmaceutically acceptable excipients. Suitable excipients include sterile water, salt solutions and buffers. In one embodiment, the hapten-carrier conjugate is solubilised in an aqueous, saline solution at a pharmaceutically acceptable pH. The vaccine composition may also optionally contain at least one auxiliary agent, such as dispersion media, coatings, surfactants, preservatives and stabilizers. The vaccine composition of the present invention preferably is sterile.

The vaccine composition of the present invention will be generally administered for both priming and boosting doses. It is expected that an initial series will include several doses that will be spaced several weeks apart with additional boosting doses being spaced months or years apart, or at such times where the levels of circulating antibody fall below a desired level that has been shown clinically to correlate with enhanced quit rates. Preferably the vaccine composition of the present invention is administered as an initial series of 3 to 6 doses administered over 6 to 24 weeks and boosting doses are administered every 3 to 12 months thereafter.

The vaccine composition of the present invention may be administered by a parenteral route, for example via intramuscular (IM), intradermal (ID) or subcutaneous (SC) injection, or, if using an appropriate device, by topical administration to the skin (transdermal) or a mucosal surface.

In certain embodiments, hapten carrier conjugates and/or vaccines of the invention can be administered intradermally (ID) through the use of microneedle devices In one aspect, the invention provides a microneedle device comprising one or more microneedles that is coated with, contains, or is effective to deliver a nicotine-derived hapten-carrier conjugate or a vaccine composition of the invention. In certain embodiments, the one or more microneedles can be prepared as patches wherein the microneedles allow simple non-invasive administration to the skin. Another aspect of the invention contemplates the use of microneedle technology for delivery of a nicotine-derived hapten-carrier conjugate or a vaccine composition of the invention.

Microneedle delivery technologies can facilitate delivery of vaccine compositions containing nicotine-derived hapten-carrier conjugate to specific and desired skin depths using arrays of short (e.g., less than 4 mm in length) needle(s). Such microneedles pierce the stratum corneum and underlying layers of the epidermis to present drug directly into the epidermis or adjacent dermis. Due to the small size of microneedles, application is relatively pain-free, with minimal (if any) bleeding or application site reaction. Herein, the term "microneedle" refers to an elongated structure that is sufficiently long to penetrate through the stratum corneum skin layer and into the epidermal/dermal layer, but sufficiently short to not result in substantial pain due to activation of nerve endings.

Microneedles that facilitate transdermal delivery are described in Prausnitz, Advanced Drug Delivery Reviews 56 (2004) 581-587; Zahn et al., Biomed. Microdevices 6 (2004) 183-190; Shirkhandeh J. Materials Sci. 16 (2005) 37-45; Park, J. Controlled Release 104 (2005) 51-66; U.S. Pat. Nos. 3,964,482, 6,503,231, 6,745,211; 6,611,707; 6,334,856; and US Patent Application Publication Nos. 2005/0209565, 2004/0106904, 2004/0186419, 2002/0193754 and 2010/0196445; all of which are hereby incorporate by reference in their entireties. Suitable microneedles have been fabricated from many materials, including silicon, metals, and polymers. Davis et al. describe the mechanics of microneedle insertion into the skin (Davis et al., J. Biomech. 37 (2004) 1155-1163).

Solid or hollow microneedles can be used in the embodiments described herein. In one embodiment, the microneedles for use in the invention are solid. For example, channels can be made by penetrating the skin with a microneedle array, followed by removal of the needles and subsequent application of the drug (see, e.g., Martanto et al., Pharm. Res. 21 (2004) and McAllister et al., PNAS 100 (2003) 13755-13760). The formulation comprising therapeutic agent according to the invention may be applied to the microneedle-treated site as a gel, hydrogel, topical cream, salve, ointment, or other topical formulation; and/or by using delivery devices such as bandages, occlusive bodies, patches, and/or the like.

In another embodiment, solid (non-porous) microneedles are coated with a nicotine-derived hapten-carrier conjugate or a vaccine composition according to the invention prior to application to the skin. The epidermis is then punctured using the microneedles, which are kept in contact with the skin surface for a sufficient period of time, allowing diffusion of the hapten-carrier conjugate or a vaccine composition into the surrounding skin tissue. (For administration of a therapeutic agent in such a fashion, see Prausnitz, Advanced Drug Delivery Reviews 56 (2004) 581-587). In another embodiment, hollow (porous) microneedles are used, which contain channels that allow storage of a hapten-carrier conjugates or a vaccine composition of the invention. Upon application to skin, the hapten-carrier conjugate or vaccine composition diffuses into the skin tissue by diffusion or pressure-driven flow. (For administration of a therapeutic agent in such a fashion, see Zahn et al., Biomed. Microdevices 6 (2004) 183-190).

In yet another embodiment, in contrast to conventional hollow needle technologies, certain aspects of the invention relate to microneedles formed from a solid matrix of dissolvable and/or biodegradable material which can be used to deliver vaccine compositions of the invention. For examples of solid microneedles see U.S. Pat. Nos. 6,945,952, 7,611,481, 2002/0082543, 2005/0197308 and 2008/0269685, all of which describe microneedle arrays made of biodegradable polymers and are hereby incorporated by reference in their entireties.

In certain embodiments, the solid microneedles can be composed of fast-dissolving and/or swelling materials, including thermoforming polymer materials that are synthetically and/or naturally derived. In certain embodiments, the solid microneedles can be formed from suitable biocompatible, biodegradable polymers such as poly(lactide)s, poly(glycolide)s, poly(lactide-co-glycolide)s, polyanhydrides, polyorthoesters, polyetheresters, polycaprolactones, polyesteramides, poly(butyric acid), poly(valeric acid), polyurethanes and copolymers and blends thereof. In other embodiments, the solid microneedles can be formed from non-biodegradable polymers such as polyacrylates, polymers of ethylene-vinyl acetates and other acyl substituted cellulose acetates, non-degradable polyurethanes, polystyrenes, polyvinyl chloride, polyvinyl fluoride, poly(vinyl imidazole), chlorosulphonate polyolefins, polyethylene oxide, blends and copolymers thereof.

Microneedles can be used alone or as arrays of more than one microneedle. Various sizes of arrays are suitable for use with the invention. In one embodiment, 1-10 microneedles are used. In other embodiments, a microneedle array comprising 10-25, 10-50, 25-50, 25-200, 25-100, or 50-100 needles is used. An array of microneedles can vary on the basis of several factors, including but not limited to, length, diameter, interneedle distance, sharpness, and the total number of microneedles used. In an exemplary embodiment, an array of microneedles comprises a 10×10 matrix. In another embodiment, an array of microneedles comprises a 20×20 matrix. In some embodiments, the distance between each microneedle in an array is from approximately 100 µm to approximately 400 µm. In an embodiment, the particular dimensions of the array can be chosen depending on the desired enhancement of skin permeability.

In some embodiments, a microneedle has a length from 20 µm to approximately 1000 µm, for example from approximately 50 µm to approximately 150 µm, or from approximately 150 µm to approximately 500 µm, or from 500 µm to approximately 1000 µm, or from 600 µm to approximately 800 µm. In other embodiment, a microneedle is approximately 50, 100, 250, 500, 600, 700, 800, 900 or 1000 µm in length. In still other embodiments, the microneedle is at least 50, 100, 250, 500, 600, 700, 800, 900 or 1000 µm in length. In other embodiments, the microneedle is less than 50, 100, 250, 500, 600, 700, 800, 900 or 1000 µm in length. In one embodiment, the microneedle is approximately 700 µm in length. In some embodiments, the microneedle penetrates skin at a depth of approximately 400 µm to approximately 700 µm. In an embodiment, the microneedle penetrates skin at a depth approximately corresponding to the bottom of the stratum corneum. In another embodiment, the microneedle penetrates skin to approximately the top of the dermal layer. In still other embodiments, the microneedle penetrates skin up to a depth approximately in between the bottom of the stratum corneum and the top of the dermal layer. The microneedle may be any of a variety of diameters as needed to maintain efficacy. In some embodiments, the outer diameter of a microneedle can be from approximately 20 µm to approximately 100 µm. In other embodiments, the outer diameter of a microneedle can be from approximately 10 µm to approximately 50 µm. The inner diameter of a hollow microneedle can be from approximately 5 µm to approximately 70 µm in some embodiments. In addition the outer or inner diameters of a microneedle can be up to 10, 20, 30, 40, 50, 60, 70, 80, 90, or 100 µm. Any combination of the above microneedle dimensions may be used as necessary with the systems and methods described herein.

A microneedle can be manufactured from a variety of materials, including but not limited to, silicon, a metal, a polymer, and glass. In some embodiments, silicon microneedles are used. Silicon microneedles, whether solid or hollow, can be etched from silicon wafers. For example, the location of each microneedle is marked and the surrounding silicon is etched away, resulting in an array of microneedles attached to a common base. In some embodiments, the thickness of a silicon wafer is between approximately 300-600 µm.

In other embodiments, microneedles are made of a metal, including but not limited to nickel, titanium, and alloys such as stainless steel. In some embodiments, metal microneedles are made from epoxy molds which are then electroplated with a chosen metal, while the epoxy mold is subsequently etched away. The resulting microneedles may either be reusable or disposable. Microneedles may also be obtained from commercial sources, including Zosano Pharma, Inc., Corium and 3M. Both Zosano and 3M have developed coated microneedle-containing patches. Corium has developed biodegradable microneedles. 3M has developed hollow microneedles (e.g. Intanza®/IDflu®.

The hapten-carrier conjugate or vaccine composition can be applied to microneedles using a variety of methods. In one embodiment, a solution comprising the hapten-carrier conjugate or vaccine composition is prepared and the solution is deposited onto/within the microneedles, followed by drying of the solution. Alternatively, the microarray is dipped into a solution comprising the hapten-carrier conjugate or vaccine composition, resulting in coating of the microneedles with the hapten-carrier conjugate or vaccine composition. When additional proteins or components are to be coated onto or within the microneedles of the invention, additional coating steps may be performed. Alternatively, several or all components of the solution are mixed into one solution which is then deposited onto/within the microneedle. Dip coating, spray coating, or other techniques known in the art may be used, for example those described in PCT Pub. No. WO 2006/138719, which is hereby incorporated by reference in its entirety. Coatings may be solid or semi-solid.

The amount of hapten-conjugated carrier protein in each vaccine dose is selected as an amount which induces an immunoprotective response without significant, adverse side effects in typical vaccines. Suitable dosage ranges are 0.01 to 10 mg/dose, preferably 0.1 to 1.0 mg/dose. It generally takes a person two or more weeks to generate antibodies against a foreign antigen after a single vaccine dose, and it generally requires several vaccine doses administered over several weeks to induce high sustained antibody titers such as those desired for an anti-nicotine vaccine to aid in smoking cessation. The production of antibodies in a person's blood can be monitored by using techniques that are well-known to the skilled artisan, such as ELISA, radioimmunoassay, surface plasma resonance, and Western blotting methods.

Thus, in a sixth aspect, the present invention relates to a hapten-carrier conjugate, or a vaccine composition as defined above, for use as a medicament.

In yet a further aspect, the present invention relates to a hapten-carrier conjugate, or a vaccine composition as defined above, for use in increasing quit rates and reducing relapse rates in smokers wishing to quit, ex-smokers wishing to avoid relapse, or for the prevention of nicotine addiction.

In yet a further aspect, the present invention relates to a nicotine-derived hapten-carrier conjugate, or a vaccine composition, as defined above, for the manufacture of a medicament for the treatment or prevention of nicotine dependence in a person in need of such treatment.

In yet a further aspect, the present invention related to a nicotine-derived hapten-carrier conjugate, or a vaccine composition, as defined above, for use in treating, or preventing, nicotine addiction in a person in need of such treatment.

In yet a further aspect, the present invention relates to a treatment method for aiding smoking cessation in smokers wishing to quit, or preventing relapse in smokers who have quit, or preventing nicotine addiction in person who might be exposed to smoking or nicotine from another source, the method comprising administering to the person an effective amount of a hapten-carrier conjugate, or a vaccine composition, as defined above.

In one embodiment, the method further comprises administering to the person another non-vaccine smoking cessation product. Suitable products include pharmacotherapy products that targets nicotinic acetylcholine receptors, such as varenicline, or bupropion, optionally in sustained-release form. Other products that can be used in the method of the invention include clonidine and nortriptyline. Additional suitable products include nicotine replacement therapy (NRT) products, in the form, for example, of a patch (16 h and 24 h), a gum, a nasal spray or an inhaler.

In yet a further aspect, the present invention relates to a method of making a hapten carrier conjugate according to the invention, comprising coupling an optionally modified carrier protein with a hapten according to the invention or a hapten-spacer conjugate according to the invention.

In yet a further aspect, the present invention relates to a method of making a hapten carrier conjugate of formula (III):

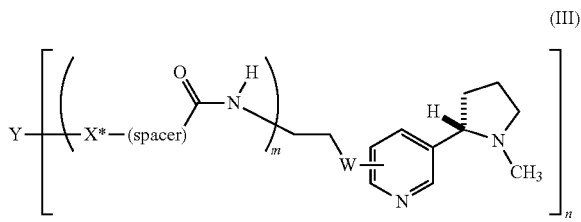

wherein W is —$CH_2$— or —O—; -(spacer)- is a $C_1$-$C_8$ alkylene group, a $C_3$-$C_{10}$ cycloalkylene group or a $C_1$-$C_{12}$ alkylene group interrupted by 1 to 4 oxygen atoms and optionally interrupted by a —N(H)C(O)—; X* is —NH—; m is 0 or 1; n is an integer from 1 to 1000; and Y is an optionally modified carrier protein selected from bacterial toxoids, immunogenic substances, viruses, virus-like particles, protein complexes, proteins, polypeptides, liposomes and immuno-stimulating complexes; comprising treating an optionally modified carrier protein with sulfo-N-hydroxysuccinimide, followed by 1-ethyl-3-(3-dimethylaminopropyl) carbodiimide hydrochloride, then adding either a hapten of the formula (I):

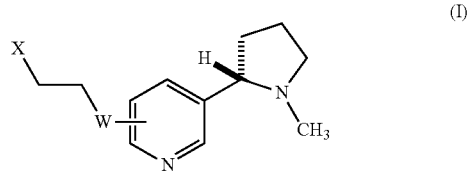

wherein W is —$CH_2$— or —O—; and X is —$NH_2$; or a hapten-spacer conjugate according to formula (II):

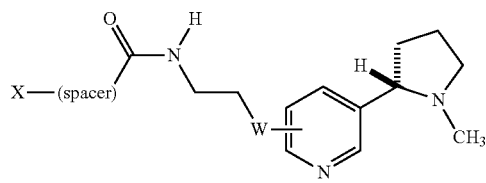

wherein W is —$CH_2$— or —O—; -(spacer)- is a $C_1$-$C_8$ alkylene group, a $C_3$-$C_{10}$ cycloalkylene group or a $C_1$-$C_{12}$ alkylene group interrupted by 1 to 4 oxygen atoms and optionally interrupted by a —N(H)C(O)—; and X is —$NH_2$.

In yet a further aspect, the present invention relates to a method of making a conjugate of formula (III):

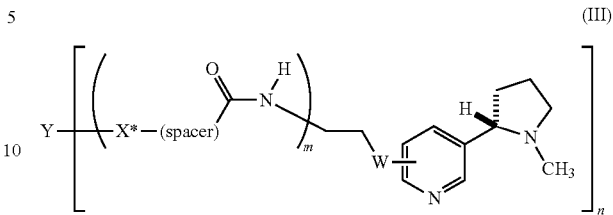

wherein W is —$CH_2$— or —O—; -(spacer)- is a $C_1$-$C_8$ alkylene group, a $C_3$-$C_{10}$ cycloalkylene group or a $C_1$-$C_{12}$ alkylene group interrupted by 1 to 4 oxygen atoms and optionally interrupted by a —N(H)C(O)—; X* is —NH—; m is 0 or 1; n is an integer from 1 to 1000; and Y is an optionally modified carrier protein selected from bacterial toxoids, immunogenic substances, viruses, virus-like particles, protein complexes, proteins, polypeptides, liposomes and immuno-stimulating complexes; comprising treating the carrier protein with succinic anhydride to give a modified succinylated carrier protein; treating the modified succinylated carrier protein with sulfo-N-hydroxysuccinimide, followed by 1-ethyl-3-(3-dimethylaminopropyl) carbodiimide hydrochloride, then adding either a hapten of the formula (I):

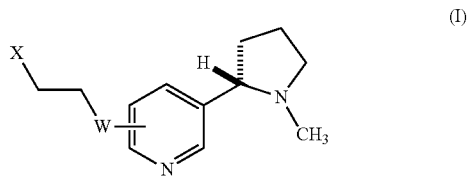

wherein W is —$CH_2$— or —O—; and X is —$NH_2$; or a hapten-spacer conjugate according to formula (II):

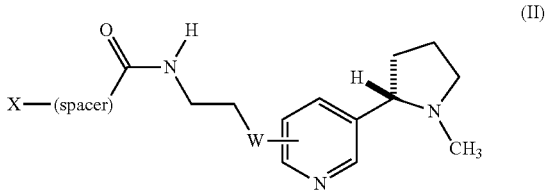

wherein W is —$CH_2$— or —O—; -(spacer)- is a $C_1$-$C_8$ alkylene group, a $C_3$-$C_{10}$ cycloalkylene group or a $C_1$-$C_{12}$ alkylene group interrupted by 1 to 4 oxygen atoms and optionally interrupted by a —N(H)C(O)—; and X is —$NH_2$.

Biological Assays

Anti-nicotine antibody ELISA. The levels of anti-nicotine antibodies in mouse plasma were quantified using an ELISA assay as follows. Since the nicotine molecule is not suitable for coating to ELISA plates, it was therefore linked to a larger molecule (bovine serum albumin) having bioadhesive properties. The nicotine derivative (rac-trans3'-thio methyl nicotine) was conjugated to bovine serum albumin and the nicotine-BSA conjugate obtained was used to coat 96 well Immuno Maxi-Sorp ELISA plates (VWR) (100 μL/well) at a final concentration of 1 μg/mL in carbonate buffer (Sigma-Aldrich), and incubated overnight at 4° C. The plates were then aspirated and washed with phosphate buffered saline containing 0.05% Tween® 20 (Sigma-Aldrich, P3563). Plates were blocked with 200 µL of blocking buffer (carbonate buffer+10% Bovine Calf Serum, Fisher) at 37° C. for 1 hour and then washed as above. Samples and reference plasma were serially diluted in dilution buffer (1×PBS with 0.05% Tween® 20+10% BCS) and added to the plates (100 µL/well). The plates were incubated at 37° C. for 2 hours. They were washed again and then incubated with goat Anti-mouse IgG-HRP (Southern Biotech), diluted with dilution buffer (1×PBS with 0.05% Tween® 20+10% BCS) for 1 hour at 37° C. The plates were then washed again and incubated with O-phenylenediamine dihydrochloride (OPD) substrate (1×5 mg OPD tablet dissolved in Phosphate Citrate Buffer, Sigma-Aldrich) in the dark for 30 min at room temperature. The reaction was stopped by the addition of 50 µL of 4N sulphuric acid (VWR) to each well and read at 450 nm using an automated plate reader. The samples were quantified as the highest plasma dilution that resulted in an antibodiesorbance value (OD 450) two times greater than that of non-immune plasma, with a cut-off value of 0.05.

Measurement of Avidity of Anti-Nicotine Antibodies.

The avidity of anti-nicotine antibodies was measured using an ammonium thiocyanate elution based ELISA method as follows. 96 well Immuno Maxi-Sorp ELISA plates (VWR) were coated (100 µL/well) with a Nicotine-BSA antigen solution at a concentration of 1 µg/mL in carbonate buffer (Sigma-Aldrich) and incubated overnight at 4° C. The plates were washed with phosphate buffered saline (PBS) containing 0.05% Tween® 20 (Sigma-Aldrich), and then blocked with 200 µL carbonate buffer+10% bovine calf serum (Fisher) for 1 hour at 37° C. The plates were washed again. Plasma samples, previously determined to contain anti-nicotine antibodies, were diluted in PBS containing 0.05% Tween® 20+10% bovine calf serum (BCS) to achieve optimal antibodiesorbance values of approximately 1.0 at 450 nm, and were then added to the plates at 100 µL/well. The plates were incubated for 2 hours at 37° C. and then washed. Next, elution was performed by adding ammonium thiocyanate (NH$_4$SCN) (100 µL/well) in concentrations ranging from 0 to 2.0 M diluted in PBS/0.05% Tween® 20 and incubated for 15 min at room temperature. The plates were then washed and antibody binding was detected using goat anti-mouse IgG-HRP (Southern Biotech) diluted with dilution buffer (1×PBS with 0.05% Tween® 20+10% BCS) for 1 hour at 37° C. The plates were then washed again and incubated with O-phenylenediamine dihydrochloride (OPD) substrate (1×5 mg OPD tablet dissolved in Phosphate Citrate Buffer, Sigma-Aldrich) in the dark for 30 min at room temperature. The reaction was stopped by the addition of 50 µL of 4N sulphuric acid (VWR) to each well and read at 450 nm using an automated plate reader. The results were then expressed as the percent reduction in binding of antigen-antibody (% reduction in OD) in the presence of NH$_4$SCN and plotted against the molar concentration of NH$_4$SCN. The avidity index was calculated as the concentration of NH$_4$SCN required to produce 50% reduction in binding.

Evaluation of Nicotine Distribution in Plasma and Brain.

The effect of immunization on nicotine distribution in the plasma and brain was determined by administering to animals (pre-immunized with an anti-nicotine vaccine) 0.05 mg/kg of (−) nicotine hydrogen tartrate containing 3 µCi $^3$H-nicotine in 100 µL of PBS over 10 seconds via tail vein infusion. Blood was obtained 5 min later via cardiac puncture and the plasma was collected. The mouse was immediately perfused with PBS by injecting 20 mL into the left ventricle of the heart over 1 to 2 min and the brain was harvested and weighed. The brain was digested at ~50° C. for 72 hours in 1 mL digestion buffer (100 mM sodium chloride, 25 mM Tris, 25 mM EDTA, 0.5% Igepal CA-630 and 0.3 mg/mL proteinase K per 100 mg tissue). 100 µL aliquots of brain digest or plasma were mixed with 5 mL liquid scintillation fluid and levels of radiolabelled nicotine were determined by liquid scintillation counting.

Competition ELISA to Determine Specificity of Antibodies Induced by Anti-Nicotine Vaccines.

The specificity of anti-nicotine antibodies was determined using a competition ELISA as follows. 96 well Immuno Maxi-Sorp ELISA plates (VWR) were coated (100 µL/well) with a Nicotine-BSA antigen solution at a concentration of 1 µg/mL in carbonate buffer (Sigma-Aldrich) and incubated overnight at 4° C. The plates were washed with phosphate buffered saline (PBS) containing 0.05% Tween® 20 (Sigma-Aldrich), blocked with 200 µL carbonate buffer+10% bovine calf serum (Fisher) for 1 hour at 37° C. and then washed again. During this incubation, plasma samples, previously determined to contain anti-nicotine antibodies, were diluted in PBS containing 0.05% Tween® 20+10% bovine calf serum (BCS) to achieve optimal antibodiesorbance values of approximately 1.0 to 1.5 at 450 nm, and different inhibitors (nicotine, cotinine, acetylcholine, varenicline) were diluted serially starting at 20,000 µM. Equal volumes (65 µL) of diluted samples and selected inhibitor were added to wells of a non-coated 96 well plate and allowed to incubate for 1 hour at 37° C. Following incubation, the plasma/inhibitor mixtures were added at 100 µL/well to the previously blocked Nicotine-BSA coated plates. The plates were incubated for 30 min at 37° C. and then washed again. Antibody binding was detected using goat anti-mouse IgG-HRP (Southern Biotech) diluted with dilution buffer (1×PBS with 0.05% Tween® 20+10% BCS) for 1 hour at 37° C. The plates were then washed again and incubated with O-phenylenediamine dihydrochloride (OPD) substrate (1×5 mg OPD tablet dissolved in Phosphate Citrate Buffer, Sigma-Aldrich) in the dark for 30 min at room temperature. The reaction was stopped by the addition of 50 µL of 4N sulphuric acid (VWR) to each well and read at 450 nm using an automated plate reader. OD readings at 450 nm were plotted against the molar concentration of inhibitor and the 50% inhibition was extrapolated for each sample tested.

EXEMPLIFICATION

The present invention is illustrated by but not limited to the following preparations and examples, in which the following abbreviations are used:

| | |
|---|---|
| Ammonia | Concentrated solution of ammonia in water possessing a specific gravity of 0.880 |
| CDCl$_3$ | Chloroform-d1 |
| Celite ® | Filtration agent |
| CI | Chemical ionisation |
| DCM | Dichloromethane |
| dPBS | Dulbecco's Phosphate buffered saline |
| DMF | N,N-Dimethylformamide |
| ES+ | Electrospray ionisation positive scan |
| EtOAc | Ethyl acetate |
| Et$_3$N | Triethylamine |
| h | Hour |
| $^1$H NMR | Proton Nuclear Magnetic Resonance |
| [Ir(cod)(OMe)]$_2$ | bis($\eta^4$-1,5-cyclooctadiene)-di-µ-methoxy-diiridium(I) |
| LCMS | Liquid chromatography-mass spectroscopy |
| MeCN | Acetonitrile |
| MeOH | Methanol |
| MgSO$_4$ | Magnesium sulfate |
| min | Minute |
| m/z | Mass spectrum peak |

| | |
|---|---|
| Pd/C | Palladium on charcoal |
| T3P | propanephosphonic anhydride, 50% w/v solution in ethyl acetate |

$^1$H NMR spectra were in all cases consistent with the proposed structures. Characteristic chemical shifts (δ) are given in parts-per-million downfield from tetramethylsilane using conventional abbreviations for designation of major peaks: e.g. s, singlet; d, doublet; t, triplet; q, quartet; m, multiplet; br, broad; brm, broad multiplet; brt, broad triplet.

LCMS, unless otherwise indicated, was performed under the following conditions: Waters XBridge C18 5 nm, 2.1×30 mm column, 0:100 to 95:5 over 3.1 min, MeCN: (10 mM $(NH_4)_2HCO_3$ aq).

PREPARATIONS

Preparation 1: (S)-3-bromo-5-(1-methylpyrrolidin-2-yl)pyridine (or 5-bromonicotine)

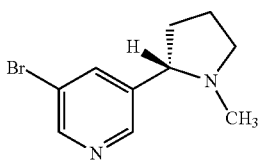

This compound was prepared following the method described in J. Am. Chem. Soc., 2007, 50, 15434-15435.

Bis(pinacolato)diboron (7.16 g, 28.21 mmol) was dissolved in 1,4-dioxane (60 mL) then degassed by bubbling argon through. (S)-(−)-Nicotine (6.48 mL, 40.3 mmol) was added, followed by 4,4'-di-tert-butyl-2,2'-dipyridyl (650 mg g, 2.42 mmol). Degassing was continued for 10 min then methoxy(cyclooctadiene)iridium(I) dimer (753 mg, 1.21 mmol) was added. The reaction mixture was heated at reflux temperature for 18 hours. The solvent was evaporated and the residue dissolved in MeOH (100 mL). Copper (II) bromide (27.0 g, 120.9 mmol) in water (100 mL) was added and the reaction mixture heated at 80° C. for 3 hours. Ammonia solution (10% aq., 100 mL) was added to the reaction mixture which was then extracted with ethyl acetate and dried over $MgSO_4$. The solvent was evaporated and the crude product was purified by flash chromatography (5% MeOH in DCM) to give the title compound as an orange oil (6.14 g, 63%).

$^1$H NMR (400 MHz, $CDCl_3$) δ=1.68-1.70 (m, 1H), 1.80-1.82 (m, 1H), 1.92-1.94 (m, 1H), 1.99-2.02 (m, 1H), 2.03 (s, 3H), 2.20-2.34 (m, 1H), 3.08 (t, 1H), 3.20 (t, 1H), 7.86 (s, 1H), 8.42 (s, 1H), 8.54 (s, 1H).

Preparation 2: (S)-3-(5-(1-methylpyrrolidin-2-yl)pyridin-3-yl)acrylonitrile

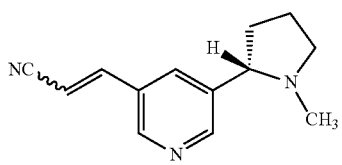 [SMILES: CN1CCC[C@H]1c1cncc(C=CC#N)c1]

A mixture of (S)-3-bromo-5-(1-methylpyrrolidin-2-yl)pyridine (preparation 1) (300 mg, 1.24 mmol), palladium (II) acetate (14 mg, 0.06 mmol), tri(o-tolyl)phosphine (75 mg, 0.25 mmol) and triethylamine (0.35 mL, 2.48 mmol) in MeCN (10 mL) was degassed by bubbling argon through. Acrylonitrile (0.12 mL, 1.87 mmol) was then added and the reaction mixture heated at reflux temperature for 18 hours. The reaction mixture was cooled to room temperature, filtered through Celite, and the solvents evaporated to give a brown solid. The crude product was purified by flash chromatography (2% [20% ammonia in MeOH] in DCM) to give the title compound as a red-brown oil (188 mg, 71%, mixture of cis and trans isomers).

$^1$H NMR (400 MHz, $CDCl_3$) δ=1.60-1.79 (m, 1H), 1.80-1.90 (m, 1H), 1.90-2.04 (m, 1H), 2.17 and 2.19 (2×s, 3H), 2.16-2.40 (m, 2H), 3.11-3.30 (m, 2H), 5.57 and 6.00 (2×d, 1H), 7.16 and 7.40 (2×d, 1H), 7.80 and 8.26 (2×s, 1H), 8.57 (s, 1H), 8.60 and 8.71 (2×s, 1H).

Preparation 3: (S)-3-(5-(1-methylpyrrolidin-2-yl)pyridin-3-yl)propanenitrile

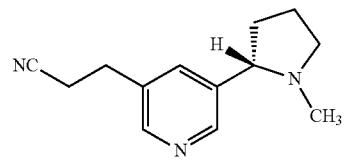 [SMILES: CN1CCC[C@H]1c1cncc(CCC#N)c1]

(S)-3-(5-(1-Methylpyrrolidin-2-yl)pyridin-3-yl)acrylonitrile (preparation 2) (185 mg, 0.87 mmol) and 5% Pd/C (50 mg) in MeOH (5 mL) were stirred under an atmosphere of hydrogen for 72 hours. The reaction mixture was filtered through Celite then the solvent evaporated. The crude product was purified by flash chromatography (5% [20% ammonia in MeOH] in DCM) to give the title compound as a pale yellow oil (141 mg, 75%).

$^1$H NMR (400 MHz, $CDCl_3$) δ=1.66-1.78 (m, 1H), 1.78-1.89 (m, 1H), 1.89-2.02 (m, 1H), 2.17 (s, 3H), 2.17-2.25 (m, 1H), 2.31 (q, 1H), 2.65 (t, 2H), 2.97 (t, 2H), 3.10 (t, 1H), 3.24 (t, 1H), 7.61 (d, 1H), 8.38 (s, 1H), 8.44 (s, 1H).

Preparation 4: (S)-3-(5-(1-methylpyrrolidin-2-yl)pyridin-3-yl)propan-1-amine

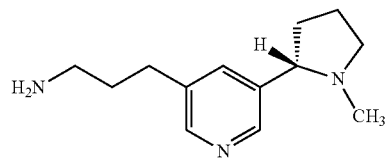 [SMILES: CN1CCC[C@H]1c1cncc(CCCN)c1]

(S)-3-(5-(1-Methylpyrrolidin-2-yl)pyridin-3-yl)propanenitrile (preparation 3) (140 mg, 0.65 mmol) and Raney nickel (50 mg) in 20% ammonia in MeOH (50 mL) were stirred under 50 psi hydrogen at 50° C. for 4 hours. The reaction mixture was filtered through Celite then the solvent evaporated. The crude product was purified by flash chromatography (7% [20% ammonia in MeOH] in DCM) to give the title compound as a pale yellow oil (126 mg, 88%).

$^1$H NMR (400 MHz, $CD_3OD$) δ=1.70-1.85 (m, 3H), 1.85-2.03 (m, 2H), 2.15 (s, 3H), 2.35 (q, 2H), 2.59-2.78 (m, 4H), 3.12-3.37 (m, 2H), 7.70 (s, 1H), 8.31 (br s, 2H).

LCMS: 1.91 min (97%), m/z=220.16 [M+H]$^+$

Preparations 5 and 6: (S)-2-chloro-5-(1-methylpyrrolidin-2-yl)pyridine (or 6-chloronicotine) and (S)-2-chloro-3-(1-methylpyrrolidin-2-yl)pyridine (or 2-chloronicotine)

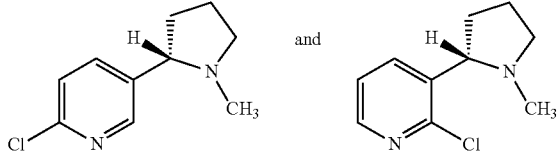

These compounds were prepared following the method described in Eur. J. Org. Chem., 2006, 3562-3565.

Butyl lithium (2M in hexanes, 83 mL, 166 mmol) was added to a solution of dimethylaminoethanol (9.3 mL, 92.5 mmol) in hexanes (70 mL) at −20° C. (S)-(−)-Nicotine (5.0 g, 30.8 mMol) in hexanes (30 mL) was added and the reaction mixture stirred at −20° C. for 1 hour. The green solution was then cooled to −78° C. and hexachloroethane (29.1 g, 123 mmol) was added. The reaction mixture was stirred for 30 min at −78° C. then quenched by the addition of ammonium chloride (sat. aq.). DCM and 2M HCl (aq.) were added. The aqueous layer was washed with DCM (×2) and then basified by the addition of ice/ammonia (aq.). The aqueous layer was extracted with DCM (×2), dried over MgSO$_4$ and evaporated. The crude products were purified by flash chromatography (20% ethyl acetate in hexanes) to give 6-chloronicotine (preparation 5) (2.2 g, 36%) and 2-chloronicotine (preparation 6) (120 mg, 2%), both as yellow oils.

6-chloronicotine: $^1$H NMR (300 MHz, CDCl$_3$) δ=1.58-2.01 (m, 3H), 2.14 (s, 3H), 2.10-2.23 (m, 1H), 2.28 (q, 1H), 3.05 (t, 1H), 3.19 (dt, 1H), 7.26 (d, 1H), 7.64 (dd, 1H), 8.27 (d, 1H).

2-chloronicotine: $^1$H NMR (300 MHz, CDCl$_3$) δ=1.45-1.60 (m, 1H), 1.76-1.98 (m, 2H), 2.22 (s, 3H), 2.31-2.49 (m, 2H), 3.24 (t, 1H), 3.55 (t, 1H), 7.20-7.29 (m, 1H), 7.93 (d, 1H), 8.24 (dd, 1H).

Preparation 7: (S)-2-(5-(1-methylpyrrolidin-2-yl)pyridin-2-yloxy)ethanamine

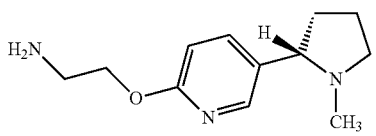

Sodium hydride (60% in oil, ~500 mg) was added to 6-chloronicotine (preparation 5) (690 mg, 3.5 mmol) in ethanolamine (3 mL). After 15 min at room temperature the reaction mixture was heated at 80° C. for 16 hours. The reaction mixture was partitioned between ethyl acetate and water. The aqueous layer was extracted with ethyl acetate, dried over MgSO$_4$ and evaporated. The crude product was purified by flash chromatography (5% [20% ammonia in MeOH] in DCM) to give the title compound as a colourless oil (44 mg, 6%).

$^1$H NMR (400 MHz, CD$_3$OD) δ=1.71-2.00 (m, 3H), 2.17 (s, 3H), 2.17-2.23 (m, 1H), 2.31 (q, 1H), 2.99 (t, 2H), 3.09 (t, 1H), 3.20 (t, 1H), 4.26 (t, 2H), 6.83 (d, 1H), 7.68 (d, 1H), 8.02 (d, 1H).

LCMS: 2.02 min (100%), m/z=222.1 [M+H]$^+$

Preparation 8: (S)-2-(3-(1-methylpyrrolidin-2-yl)pyridin-2-yloxy)ethanamine

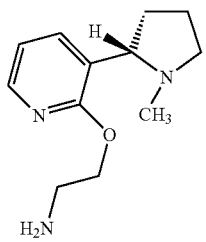

Sodium hydride (60% in oil, ~200 mg) was added to 2-chloronicotine (preparation 6) (120 mg, 0.61 mmol) in ethanolamine (2 mL). After 15 min at room temperature the reaction mixture was heated at 80° C. for 16 hours. The reaction mixture was partitioned between ethyl acetate and water. The aqueous layer was extracted with ethyl acetate, dried over MgSO$_4$ and evaporated. The crude product was purified by flash chromatography (5% [20% ammonia in MeOH] in DCM) to give the title compound as a colourless oil (8.5 mg, 6%).

$^1$H NMR (400 MHz, CD$_3$OD) δ=1.60-1.70 (m, 1H), 1.81-1.99 (m, 2H), 2.20 (s, 3H), 2.23-2.40 (m, 2H), 3.03 (t, 2H), 3.19 (t, 1H), 3.53 (t, 1H), 4.27-4.41 (m, 2H), 6.96 (d, 1H), 7.74 (d, 1H), 8.00 (d, 1H).

LCMS: 2.03 min (99%), m/z=222.1 [M+H]$^+$

Preparation 9: (S)-3-(4-methoxybenzyloxy)-5-(1-methylpyrrolidin-2-yl)pyridine

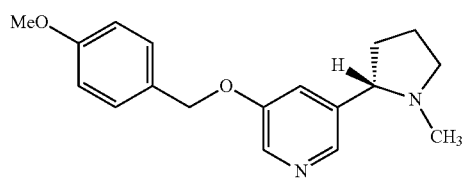

(plus 4 or 6 isomer)

Sodium hydride (60% in oil, 650 mg, 32.5 mmol) was added to 4-methoxybenzyl alcohol (1.4 g, 11.6 mmol) in DMF (10 mL). After 30 min at room temperature 5-bromonicotine (preparation 1) (1.4 g, 11.6 mmol) in DMF (2 mL) was added. The reaction mixture was heated at 90° C. for 16 hours. The reaction mixture was partitioned between ethyl acetate and water. The aqueous layer was extracted with ethyl acetate, the organic layers combined, dried over MgSO$_4$ and evaporated. The crude product was purified by flash chromatography (2.5%→5% MeOH in DCM) to give the title compound as a yellow oil, mixed with ~30% of another isomer (402 mg, 23%).

Preparation 10: (S)-5-(1-methylpyrrolidin-2-yl)pyridin-3-ol (or 5-hydroxynicotine)

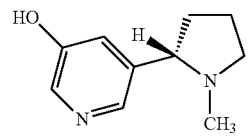

Preparation 10a: (S)-3-(4-Methoxybenzyloxy)-5-(1-methylpyrrolidin-2-yl)pyridine (preparation 9) (400 mg, 1.34 mmol) was stirred in trifluoroacetic acid (2 mL) and DCM (5 mL) for 2 hours. The reaction mixture was evaporated, then co-evaporated with DCM (×5) and 20% ammonia in MeOH. The crude product was purified by flash chromatography (10% MeOH in DCM) to give the title compound as a yellow oil (225 mg, 94%).

¹H NMR (400 MHz, CDCl₃) δ=2.20-2.39 (m, 3H), 2.48-2.59 (m, 1H), 2.76 (s, 3H), 3.83 (br s, 1H), 4.38 (br s, 1H), 7.42 (d, 1H), 8.16 (s, 1H), 8.20 (s, 1H).

LCMS: 1.26 min (100%), m/z=179.1 [M+H]⁺

Preparation 10b: (S)—Nicotine (54 mL, 336.2 mmol) and 4,4'-di-tertbutyl-2,2'-dipyridyl (5.41 g, 20.2 mmol) were added successively to a solution of bis(pinacolato)diboron (59.8 g, 235.5 mmols) in 1,4-dioxane (218 mL). The resulting solution was degassed under vacuum, at room temperature, for 15 to 20 minutes and then released to nitrogen. The procedure was then repeated twice more.

[Ir(cod)(OMe)]₂ (6.7 g, 10.1 mmol) was charged to the reaction vessel and the reaction mixture was degassed under vacuum, at room temperature, for 5 minutes, then released to nitrogen. The procedure was then repeated twice more.

The resulting solution was heated at 85° C. for 16 hours, after which time analysis indicated complete reaction. The reaction mixture was cooled to room temperature and concentrated to dryness under reduced pressure, at 50 to 55° C. The resulting orange residue was dissolved in tetrahydrofuran (740 mL) and the solution was cooled to between 0 and 5° C. Acetic acid (52.1 mL, 908.8 mmol) was charged to the vessel, followed by slow addition of hydrogen peroxide solution (30%, 43.1 mL, 454.4 mmol), maintaining the temperature at between 0 and 10° C. The resulting mixture was stirred for 16 hours at room temperature, after which time analysis indicated complete reaction.

The reaction mixture then was cooled to between 0 and 5° C., and quenched by the addition of aqueous sodium metabisulphite solution (30%, 50 mL). The pH of the resulting mixture was adjusted by the addition of concentrated ammonium hydroxide solution (130 mL). The layers of the resulting biphasic mixture were separated and the aqueous layer was re-extracted with tetrahydrofuran (300 mL). The combined organic layers were concentrated to give the crude compound as an orange gum. This was purified by column chromatography on silica gel (MeOH in DCM, 5 to 20%) to remove the majority of impurities, followed by further column chromatography (100% THF) to remove isomeric impurities. Pure 5-hydroxynicotine was isolated as a yellow solid (26 g, 48% yield).

¹H NMR (400 MHz, CDCl₃) δ=1.70-2.05 (m, 4H), 2.21 (s, 3H), 2.31 (m, 1H), 3.11 (t, 1H), 3.25 (m, 1H), 7.32 (d, 1H), 8.01 (s, 1H), 8.05 (s, 1H).

Preparation 11: (S)-tert-butyl 2-(5-(1-methylpyrrolidin-2-yl)pyridin-3-yloxy)ethylcarbamate

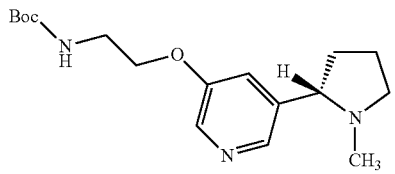 [SMILES: CN1CCC[C@H]1c1cncc(OCCNC(=O)OC(C)(C)C)c1]

(S)-5-(1-Methylpyrrolidin-2-yl)pyridin-3-ol (preparation 10) (175 mg, 0.98 mmol), tert-butyl 2-bromoethylcarbamate (550 mg, 2.45 mmol) and potassium carbonate (676 mg, 4.9 mmol) in DMF (7 mL) were heated at 90° C. for 16 hours. The reaction mixture was partitioned between ethyl acetate and water. The aqueous layer was extracted with ethyl acetate, dried over MgSO₄ and evaporated. The crude product was purified by flash chromatography (5%→10% MeOH in DCM) to give the title compound as a yellow oil (108 mg, 34%).

¹H NMR (400 MHz, CDCl₃) δ=1.42 (s, 9H), 1.70-2.00 (m, 3H), 2.17 (s, 3H), 2.09-2.20 (m, 1H), 2.20-2.30 (q, 1H), 3.15-3.26 (m, 2H), 3.45 (t, 2H), 4.08 (t, 2H), 7.43 (d, 1H), 8.07 (s, 1H), 8.13 (s, 1H).

LCMS: 2.62 min (100%), m/z=322.15 [M+H]⁺

Preparation 12: (S)-2-(5-(1-methylpyrrolidin-2-yl)pyridin-3-yloxy)ethanamine

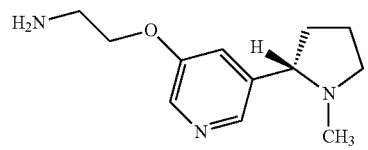 [SMILES: CN1CCC[C@H]1c1cncc(OCCN)c1]

Preparation 12a: (S)-tert-butyl 2-(5-(1-Methylpyrrolidin-2-yl)pyridin-3-yloxy)ethylcarbamate (preparation 11) (105 mg, 0.33 mmol) was stirred in trifluoroacetic acid (1 mL) and DCM (5 mL) for 1.5 h. The reaction mixture was evaporated, then co-evaporated with DCM (×5) and 20% ammonia in MeOH. The crude product was purified by flash chromatography (5% [20% ammonia in MeOH] in DCM) to give the title compound as a yellow oil (62 mg, 85%).

¹H NMR (400 MHz, CDCl₃) δ=1.70-2.01 (m, 3H), 2.17 (s, 3H), 2.18-2.30 (m, 1H), 2.30-2.40 (m, 1H), 3.03 (t, 2H), 3.14-3.28 (m, 2H), 4.08 (t, 2H), 7.44 (d, 1H), 8.08 (s, 1H), 8.16 (s, 1H).

LCMS: 1.87 min (100%), m/z=222.12 [M+H]⁺

Preparation 12b: Potassium methoxide (3.37 g, 46.2 mmol), in methanol (40 mL), was charged to a solution of 5-hydroxynicotine (preparation 10b) (8.0 g, 44.0 mmol) in methanol (40 mL), at between 0 and 5° C. The resulting mixture was stirred for 90 minutes and then concentrated to dryness under reduced pressure at 45° C.

Boc-1-Amino-2-bromoethane (14.8 g, 66.0 mmol) in dimethyl formamide (80 mL) was heated to 50° C. under nitrogen, at which point the previously prepared potassium salt of 5-hydroxynicotine was charged to the vessel, followed immediately by potassium carbonate (6.7 g, 48.4 mmol).

The resulting mixture was heated at 85° C. for 4 hours and then cooled to room temperature. It was concentrated under reduced pressure at 50° C. and the resulting orange mixture was stirred in 1,4-dioxane (50 mL) for 15 minutes. The solution was then filtered and the liquors were cooled to between 0 and 5° C., then acidified with 4M HCl in 1,4-dioxane (65 mL). The mixture was concentrated under reduced pressure at 50° C. and the resulting residue was dissolved in tetrahydrofuran (30 mL). This mixture was then cooled to between 0 and 5° C., and the pH was adjusted with sodium hydroxide solution (10M, 45 mL). The layers of the resulting biphasic mixture were separated and the aqueous layer was re-extracted with tetrahydrofuran (2×50 mL) The combined organic layers were concentrated to give the crude compound as a red oil. The crude product was dissolved in DCM and stirred for 10 minutes, then filtered and the liquors were loaded onto a silica column and purified by eluting with 5 to 30% methanol (containing 20% ammonium hydroxide) in ethyl acetate. The title compound was obtained as a yellow oil, 7.15 g (73% yield).

¹H NMR (400 MHz, CDCl₃) δ=1.65-1.80 (m, 3H), 1.85 (m, 1H), 1.95 (m, 1H), 2.19 (s, 3H), 2.21 (m, 1H), 2.35 (q, 1H), 3.12 (m, 3H), 3.28 (t, 1H), 4.08 (t, 2H), 7.28 (s, 1H), 8.15 (s, 1H), 8.23 (s, 1H).

Preparation 13: tert-butyl {trans-4-[(3-{5-[(2S)-1-methylpyrrolidin-2-yl]pyridin-3-yl}propyl)carbamoyl]cyclohexyl}carbamate

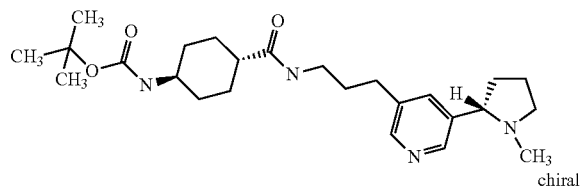 [SMILES: CN1CCC[C@H]1c1cncc(CCCNC(=O)[C@H]2CC[C@H](NC(=O)OC(C)(C)C)CC2)c1]

A solution of 3-{5-[(2S)-1-methylpyrrolidin-2-yl]pyridin-3-yl}propan-1-amine (preparation 4) (100 mg, 0.45 mmol) in 2-methyltetrahydrofuran (2 ml) was treated, with stirring, with trans-4-tert-butoxycarbonyl-cyclohexane carboxylic acid (132 mg, 0.502 mmol) followed by T3P (580 μl, 0.91 mmol) and then Et₃N (118 μl, 0.91 mmol). After stirring for 3 hours, the solution was treated with T3P (240 μL, 0.38 mmol). After stirring for 18 hours the solution was concentrated in vacuo and the residue was taken up in MeOH and applied to an SCX-2 cartridge which was eluted with MeOH followed by ammonia in MeOH (~2M). Product containing fractions were concentrated in vacuo and the residue purified by column chromatography on silica gel eluting with EtOAc:MeOH:NH₃ (gradient from 1:0:0 to 90:10:1) to give the title compound as a gum (130 mg, 64%).

¹H NMR (400 MHz, CDCl₃) δ=1.04-1.14 (m, 2H), 1.42 (s, 9H), 1.48-1.59 (m, 2H), 1.65-1.74 (m, H), 1.79-2.02 (m, 7H), 2.05-2.09 (brm, 2H), 2.13-2.22 (m, 4H), 2.26-2.33 (m, H), 2.60-2.64 (t, 2H), 3.04-3.08 (t, H), 3.20-3.30 (m, 3H), 3.40 (brm, H), 4.39 (brm, H), 5.56 (brt, H), 7.50 (t, H), 8.30-8.31 (d, H), 8.34-8.35 (d, H).

MS, m/z=568 ES+ [M+H]⁺, 567 Cl [M+H]⁺

Preparation 14: tert-butyl (19-{5-[(2S)-1-methylpyrrolidin-2-yl]pyridin-3-yl}-15-oxo-3,6,9,12-tetraoxa-16-azanonadec-1-yl)carbamate

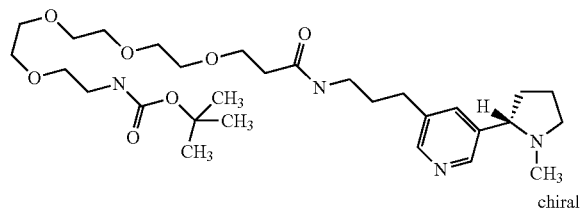 [SMILES: CN1CCC[C@H]1c1cncc(CCCNC(=O)CCOCCOCCOCCOCCNC(=O)OC(C)(C)C)c1]

The title compound was prepared by the general method described above for preparation 13, using 3-(2-{2-[2-(2-tert-Butoxycarbonylamino-ethoxy)-ethoxy]-ethoxy}-ethoxy)-propionic acid instead of trans-4-tert-butoxycarbonyl-cyclohexane carboxylic acid, to yield a pale yellow gum (180 mg, 70%).

¹H NMR (400 MHz, CDCl₃) δ=1.41 (s, 9H), 1.65-1.76 (m, H), 1.78-1.86 (m, 3H), 1.88-2.01 (m, H), 2.13-2.21 (m, 4H), 2.25-2.32 (m, H), 2.44-2.47 (t, 2H), 2.61-2.65 (t, 2H), 3.03-3.07 (t, H), 3.19-3.29 (m, 6H), 3.49-3.52 (t, 2H), 3.57-3.62 (m, 11H), 3.70-3.73 (t, 2H), 5.21 (brm, H), 6.66 (brm, H), 7.51 (t, H), 8.30-8.31 (d, H),] 8.33 (d, H).

MS, m/z=445 ES+ [M+H]⁺, 445 Cl [M+H]⁺

Preparation 15: tert-butyl {2-[(3-{5-[(2S)-1-methylpyrrolidin-2-yl]pyridin-3-yl}propyl)amino]-2-oxoethyl}carbamate

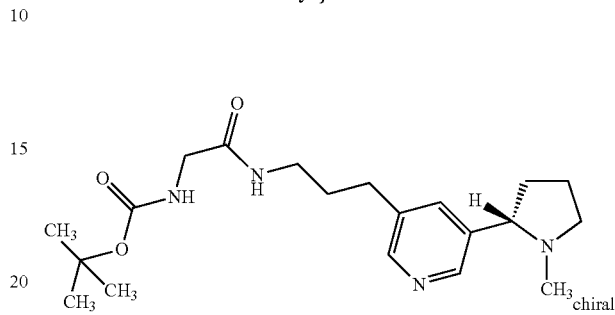

The title compound was prepared by the general method described above for preparation 13, using tert-butoxylcarbonylamino-acetic acid instead of trans-4-tert-butoxycarbonyl-cyclohexane carboxylic acid, to yield a pale yellow gum (133 mg, 77%).

¹H NMR (400 MHz, CDCl₃) δ=1.45 (s, 9H), 1.66-1.77 (m, H), 1.79-1.90 (m, 3H), 1.91-2.02 (m, H), 2.14-2.23 (m, 4H), 2.27-2.34 (q, H), 2.62-2.66 (m, 2H), 3.04-3.09 (t, H), 3.21-3.26 (m, H), 3.28-3.34 (m, 2H), 3.75-3.76 (d, 2H), 5.21 (brm, H), 6.29 (brm, H), 7.52 (t, H), 8.31-8.32 (d, H), 8.34-8.35 (d, H).

MS, m/z=377 ES+ [M+H]⁺, 377 Cl [M+H]⁺

Preparation 16: tert-butyl {3-[(3-{5-[(2S)-1-methylpyrrolidin-2-yl]pyridin-3-yl}propyl)amino]-3-oxopropyl}carbamate

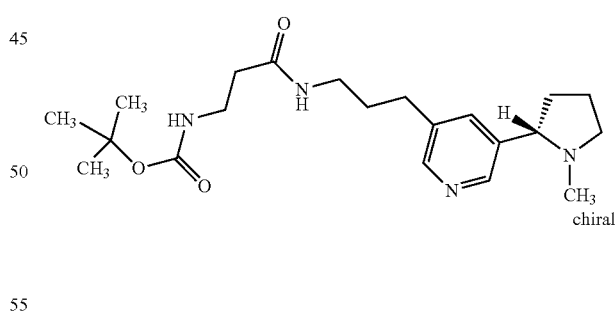

The title compound was prepared by the general method described above for preparation 13, using tert-butoxylcarbonylamino-propionic acid instead of trans-4-tert-butoxycarbonyl-cyclohexane carboxylic acid, to yield a pale yellow gum (130 mg, 73%).

¹H NMR (400 MHz, CDCl₃) δ=1.41 (s, 9H), 1.67-1.75 (m, H), 1.79-1.88 (m, 3H), 1.91-2.00 (m, H), 2.14-2.23 (m, 4H), 2.27-2.33 (q, H), 2.37-2.40 (t, 2H), 2.62-2.66 (m, 2H), 3.04-3.08 (t, H), 3.20-3.30 (m, 3H), 3.37-3.41 (q, 2H), 5.26 (brm, H), 6.00 (brm, H), 7.52 (t, H), 8.31-8.32 (d, H), 8.34 (d, H).

MS, m/z=391 ES+ [M+H]⁺, 391 Cl [M+H]⁺

Preparation 17: tert-butyl {4-[(3-{5-[(2S)-1-methylpyrrolidin-2-yl]pyridin-3-yl}propyl)amino]-4-oxobutyl}carbamate

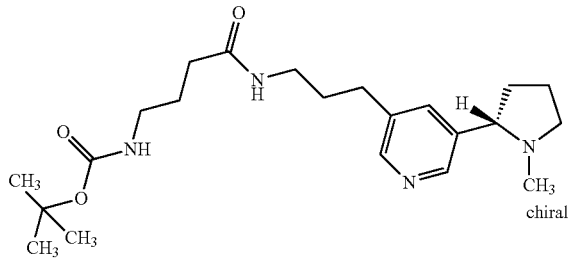 [SMILES: CN1CCC[C@H]1c1cncc(CCCNC(=O)CCCNC(=O)OC(C)(C)C)c1]

The title compound was prepared by the general method described above for preparation 13, using tert-butoxylcarbonylamino-butanoic acid instead of trans-4-tert-butoxycarbonyl-cyclohexane carboxylic acid, to yield a pale yellow gum (140 mg, 76%).

$^1$H NMR (400 MHz, CDCl$_3$) δ=1.40 (s, 9H), 1.64-1.72 (m, H), 1.74-1.87 (m, 5H), 1.87-1.89 (m, H), 2.12-2.20 (m, 6H), 2.24-2.31 (q, H), 2.62-2.66 (m, 2H), 3.02-3.06 (t, H), 3.11-3.16 (q, 2H), 3.18-3.29 (m, 3H), 4.91 (brm, H), 6.57 (brm, H), 7.51 (t, H), 8.30 (d, H), 8.32 (d, H).

MS, m/z=405 ES+ [M+H]$^+$, 405 Cl [M+H]$^+$

Preparation 18: tert-butyl [2-(2-{2-[(3-{5-[(2S)-1-methylpyrrolidin-2-yl]pyridin-3-yl}propyl)amino]-2-oxoethoxy}ethoxy)ethyl]carbamate

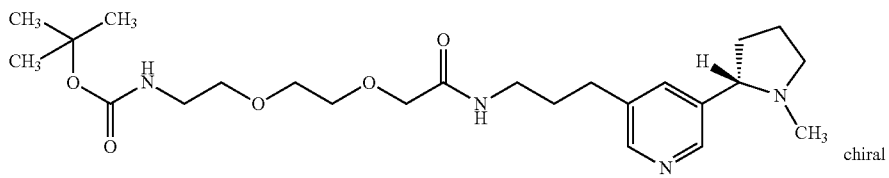 [SMILES: CN1CCC[C@H]1c1cncc(CCCNC(=O)COCCOCCNC(=O)OC(C)(C)C)c1]

The title compound was prepared by the general method described above for preparation 13, using [2-(2-tert-Butoxycarbonylamino-ethoxy)-ethoxy]-acetic acid (prepared as described in Angew. Chemie Int. Ed. (2006), 45(30), 4936-4940) instead of trans-4-tert-butoxycarbonyl-cyclohexane carboxylic acid, to yield a colourless gum (60 mg, 28%).

$^1$H NMR (400 MHz, CDCl$_3$) δ=1.42 (s, 9H), 1.67-1.98 (m, 7H), 2.14-2.23 (m, 4H), 2.27-2.33 (q, H), 2.64-2.68 (m, 2H), 3.04-3.09 (t, H), 3.21-3.26 (m, H), 3.29-3.37 (m, 3H), 3.53-3.56 (t, 2H), 3.62-3.68 (m, 4H), 3.98 (s, 2H), 4.99 (brm, H), 6.88 (brm, H), 7.53 (t, H), 8.33 (d, H), 8.35 (d, H).

MS, m/z=465 ES+ [M+H]$^+$, 465 Cl [M+H]$^+$

Preparation 19: tert-butyl (2-{2-[(3-{5-[(2S)-1-methylpyrrolidin-2-yl]pyridin-3-yl}propyl)amino]-2-oxoethoxy}ethyl)carbamate The title compound was prepared by the general method described above for preparation 13, using (2-tert-butoxycarbonylamino-ethoxy)-acetic acid instead of trans-4-tert-butoxycarbonyl-cyclohexane carboxylic acid, to yield a pale yellow gum (105 mg, 55%).

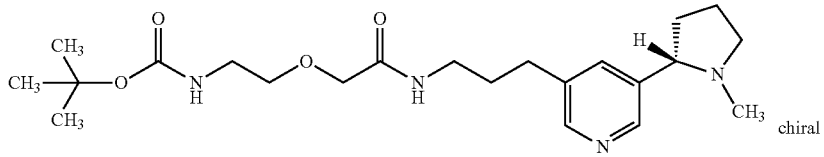 [SMILES: CN1CCC[C@H]1c1cncc(CCCNC(=O)COCCNC(=O)OC(C)(C)C)c1]

$^1$H NMR (400 MHz, CDCl$_3$) δ=1.43 (s, 9H), 2.16-2.24 (m, 5H), 2.31 (q, 4H), 2.66 (t, 1H), 3.07 (t, 2H), 3.24 (t, 1H), m, 1H), 3.32-3.37 (m, 4H), 3.56 (t, 2H), 3.94 (s, 2H), 4.98 (br, 1H), 6.69 (br, 1H), 7.54 (t, 1H), 8.33-8.36 (m, 2H).

MS m/z=421 ES+ [M+H]$^+$

Preparation 20: tert-butyl {5-[(3-{5-[(2S)-1-methylpyrrolidin-2-yl]pyridin-3-yl}propyl)amino]-5-oxopentyl}carbamate

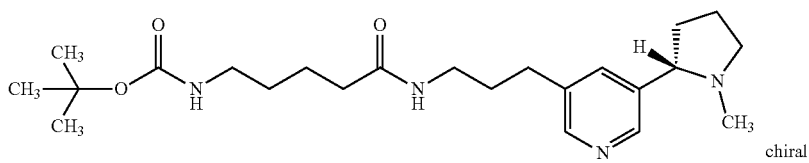 [SMILES: CN1CCC[C@H]1c1cncc(CCCNC(=O)CCCCNC(=O)OC(C)(C)C)c1]

The title compound was prepared by the general method described above for preparation 13, using tert-butoxylcarbonylamino-pentanoic acid instead of trans-4-tert-butoxycarbonyl-cyclohexane carboxylic acid, to yield a pale yellow gum (191 mg, 64%).

¹H NMR (400 MHz, CDCl₃) δ=1.43 (s, 9H), 1.47-1.53 (m, 2H), 1.63-1.75 (m, 3H), 1.80-1.89 (m, 4H), 1.94-2.05 (m, H), 2.16 (s, 3H), 2.16-2.23 (m, 2H), 2.31 (q, H), 2.65 (t, 2H), 3.07 (t, H), 3.14-31.6 (m, 2H), 3.22-3.30 (m, 3H), 5.30 (br, H), 5.80 (br, H), 7.53 (t, H), 8.33 (m, H), 8.35 (m, H).

MS m/z=420 ES+ [M+H]⁺

Preparation 21: tert-butyl {6-[(3-{5-[(2S)-1-methylpyrrolidin-2-yl]pyridin-3-yl}propyl)amino]-6-oxohexyl}carbamate

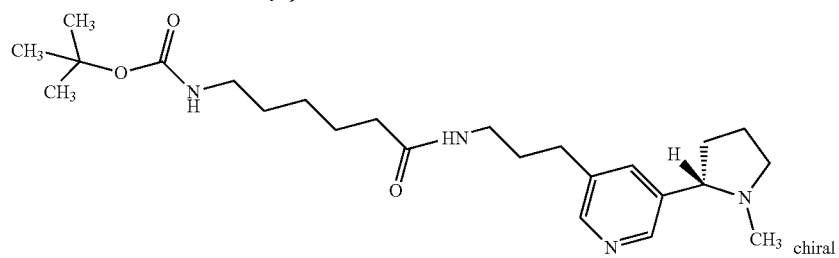

The title compound was prepared by the general method described above for preparation 13, using tert-butoxylcarbonylamino-hexanoic acid instead of trans-4-tert-butoxycarbonyl-cyclohexane carboxylic acid, to yield a pale yellow gum (197 mg, 50%).

¹H NMR (400 MHz, CDCl₃) δ=1.32-1.37 (m, 2H), 1.43 (s, 9H), 1.46-1.54 (m, 2H), 1.61-1.69 (m, 2H), 1.69-1.77 (m, H), 1.81-1.89 (m, 5H), 1.95-2.00 (m, H), 2.14-2.22 (m, 5H), 2.30 (q, H), 2.65 (t, 2H), 3.05-3.13 (m, 3H), 3.22-3.33 (m, 3H), 4.62 (br, H), 5.63 (br, H), 7.53 (t, H), 8.33 (m, H), 8.35 (m, H).

MS m/z=434 ES+ [M+H]⁺

Preparation 22: tert-butyl {7-[(3-{5-[(2S)-1-methylpyrrolidin-2-yl]pyridin-3-yl}propyl)amino]-7-oxoheptyl}carbamate

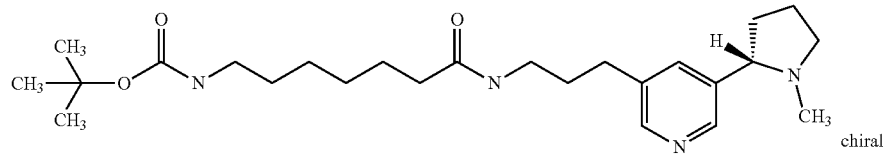 [SMILES: CN1CCC[C@H]1c1cncc(CCCNC(=O)CCCCCCNC(=O)OC(C)(C)C)c1]

The title compound was prepared by the general method described above for preparation 13, using tert-butoxylcarbonylamino-heptanoic acid instead of trans-4-tert-butoxycarbonyl-cyclohexane carboxylic acid, to yield a pale yellow gum (204 mg, 55%).

¹H NMR (400 MHz, CDCl₃) δ=1.31-1.35 (m, 4H), 1.44 (s, 9H), 1.44-1.49 (m, 2H), 1.60-1.67 (m, 2H), 1.70-1.77 (m, H), 1.81-1.89 (m, 5H), 1.94-1.99 (m, H), 2.13-2.23 (m, 5H), 2.30 (q, H), 2.65 (t, 2H), 3.05-3.12 (m, 3H), 3.22-3.33 (m, 3H), 4.37 (br, H), 5.68 (br, H), 7.53 (t, H), 8.33 (m, H), 8.35 (m, H).

MS m/z=448 ES+ [M+H]⁺

Preparation 23: tert-butyl (22-{5-[(2S)-1-methylpyrrolidin-2-yl]pyridin-3-yl}-15,18-dioxo-4,7,10-trioxa-14,19-diazadocos-1-yl)carbamate

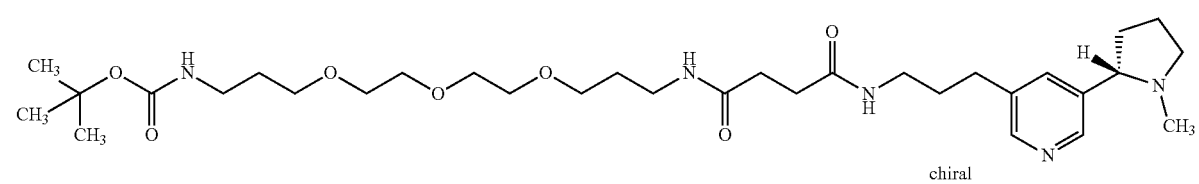 [SMILES: CN1CCC[C@H]1c1cncc(CCCNC(=O)CCC(=O)NCCCOCCOCCOCCCNC(=O)OC(C)(C)C)c1]

The title compound was prepared by the general method described above for preparation 13, using N-(3-{2-[2-(3-tert-butoxycarbonylamino-propoxy)-ethoxy]-ethoxy}-propyl)-succinamic acid instead of trans-4-tert-butoxycarbonyl-cyclohexane carboxylic acid, to yield a pale yellow gum (284 mg, 53%).

¹H NMR (400 MHz, CDCl₃) δ=1.43 (s, 9H), 1.71-1.77 (m, 9H), 1.87-2.02 (m, 4H), 2.16-2.22 (m, 4H), 2.30 (q, H), 2.63 (t, 2H), 3.06 (t, H), 3.19-3.28 (m, 5H), 3.33-3.37 (m, 2H), 3.51-3.65 (m, 12H), 5.09 (br, H), 6.59 (br, H), 6.64 (br, H), 7.52 (t, H), 8.32 (m, H), 8.35 (m, H).

MS m/z=622 ES+ [M+H]⁺

Preparation 24: trans-4-amino-N-(3-{5-[(2S)-1-methylpyrrolidin-2-yl]pyridin-3-yl}propyl)cyclohexanecarboxamide

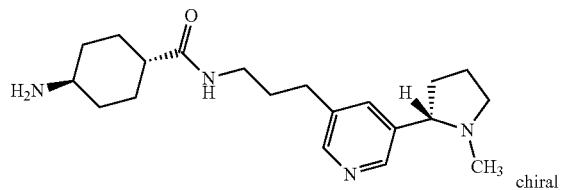 [SMILES: CN1CCC[C@H]1c1cncc(CCCNC(=O)[C@H]2CC[C@H](N)CC2)c1]

A solution of tert-butyl {trans-4-[(3-{5-[(2S)-1-methylpyrrolidin-2-yl]pyridin-3-yl}propyl)carbamoyl]cyclohexyl}carbamate (preparation 13) (130 mg, 0.29 mmol) in DCM (3 mL) was treated with trifluoroacetic acid (1 mL). The resulting solution was stirred at ambient temperature for 2 hours after which time it was concentrated in vacuo. The residue was dissolved in MeOH and applied to an SCX-2 cartridge and eluted with MeOH followed by ammonia in MeOH (2M). The fractions containing product were concentrated in vacuo to give the title compound as a colourless gum (98 mg, 97%).

¹H NMR (400 MHz, CDCl₃) δ=1.02-1.12 (m, 2H), 1.45-1.76 (m, 5H), 1.77-2.03 (m, 9H), 2.12-2.21 (m, 4H), 2.25-2.32 (q, H), 2.59-2.68 (m, 3H), 3.02-3.06 (t, H), 3.19-3.29 (m, 3H), 5.66 (br, H), 7.49 (t, H), 8.29 (d, H), 8.33 (d, H).

MS, m/z=345 and 367 ES+ [M+H]⁺ and [M+Na]⁺, 345 Cl [M+H]⁺

Preparation 25: 1-amino-N-(3-{5-[(2S)-1-methylpyrrolidin-2-yl]pyridin-3-yl}propyl)-3,6,9,12-tetraoxapentadecan-15-amide

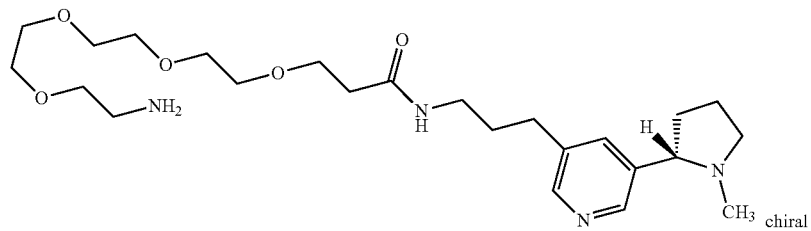 [SMILES: CN1CCC[C@H]1c1cncc(CCCNC(=O)CCOCCOCCOCCOCCN)c1]

The title compound was prepared by the general method described above for preparation 24, starting from preparation 14, to yield a colourless gum (149 mg, 100%).

¹H NMR (400 MHz, CDCl₃) δ=1.64-1.75 (m, H), 1.77-1.99 (m, 7H), 2.12-2.21 (m, 4H), 2.25-2.32 (q, H), 2.44-2.46 (t, 2H), 2.60-2.64 (t, 2H), 2.82-2.85 (t, 2H), 3.02-3.06 (t, H), 3.19-3.29 (m, 3H), 3.47-3.50 (t, 2H), 3.59-3.61 (m, 11H), 3.69-3.72 (t, 2H), 6.76 (brm, H), 7.50 (t, H), 8.30-8.31 (d, H), 8.33 (d, H).

MS, m/z=467 and 489 ES+ [M+H]⁺ and [M+Na]⁺, 467 Cl [M+H]⁺

Preparation 26: N-(3-{5-[(2S)-1-methylpyrrolidin-2-yl]pyridin-3-yl}propyl)glycinamide

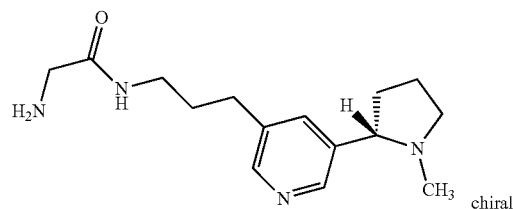 [SMILES: CN1CCC[C@H]1c1cncc(CCCNC(=O)CN)c1]

The title compound was prepared by the general method described above for preparation 24, starting from preparation 15, to yield a colourless gum (99 mg, 100%).

¹H NMR (400 MHz, CDCl₃) δ=1.66-2.01 (m, 7H), 2.13-2.22 (m, 4H), 2.27-2.33 (q, H), 2.62-2.66 (t, 2H), 3.05-3.09 (t, H), 3.21-3.26 (t, H), 3.29-3.34 (m, 4H), 7.35 (brm, H), 7.53 (t, H), 8.32 (d, H), 8.33-8.34 (d, H).

MS, m/z=277 and 291 ES+ [M+H]⁺ and [M+Na]⁺, 277 Cl [M+H]⁺

Preparation 27: N-(3-{5-[(2S)-1-methylpyrrolidin-2-yl]pyridin-3-yl}propyl)-beta-alaninamide

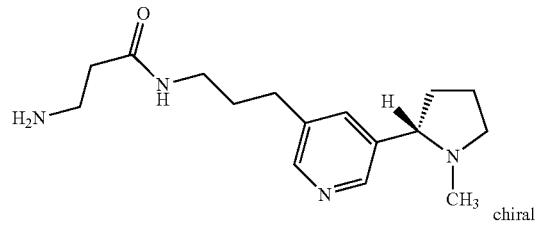 [SMILES: CN1CCC[C@H]1c1cncc(CCCNC(=O)CCN)c1]

The title compound was prepared by the general method described above for preparation 24, starting from preparation 16, to yield a colourless gum (99 mg, 100%).

¹H NMR (400 MHz, CDCl₃) δ=1.65-1.76 (m, H), 1.77-2.00 (m, 6H), 2.13-2.22 (m, 4H), 2.26-2.32 (m, 3H), 2.62-2.66 (t, 2H), 2.98-3.01 (t, 2H), 3.03-3.08 (t, 2H) 3.20-3.31 (m, 3H), 7.26 (brm, H), 7.51 (t, H) 8.31-8.32 (d, H), 8.33-8.34 (d, H).

MS, m/z=291 and 313 ES+ [M+H]⁺ and [M+Na]⁺, 291 Cl [M+H]⁺

Preparation 28: 4-amino-N-(3-{5-[(2S)-1-methylpyrrolidin-2-yl]pyridin-3-yl}propyl) butanamide

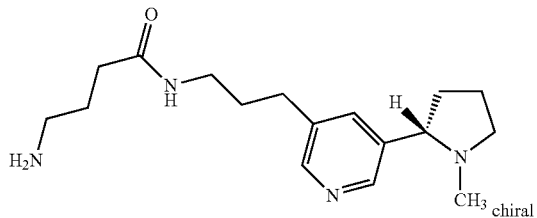 [SMILES: CN1CCC[C@H]1c1cncc(CCCNC(=O)CCCN)c1]

The title compound was prepared by the general method described above for preparation 24, starting from preparation 17, to yield a colourless gum (104 mg, 99%).

$^1$H NMR (400 MHz, CDCl$_3$) δ=1.65-2.00 (m, 9H), 2.13-2.32 (m, 7H), 2.61-2.65 (t, 2H), 2.72-2.76 (t, 2H) 3.03-3.07 (t, H) 3.20-3.30 (m, 3H), 6.22 (brm, H), 7.50 (t, H), 8.30-8.31 (d, H) 8.33-8.34 (d, H).

MS, m/z=305 and 327 ES+ [M+H]$^+$ and [M+Na]$^+$, 305 Cl [M+H]$^+$

Preparation 29: 2-[2-(2-aminoethoxy)ethoxy]-N-(3-{5-[(2S)-1-methylpyrrolidin-2-yl]pyridin-3-yl}propyl)acetamide

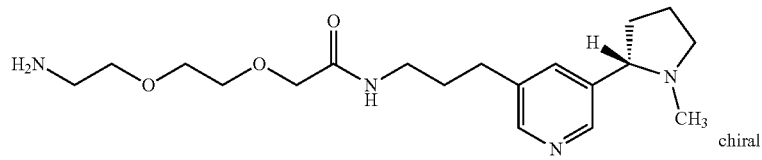 [SMILES: CN1CCC[C@H]1c1cncc(CCCNC(=O)COCCOCCN)c1]

The title compound was prepared by the general method described above for preparation 24, starting from preparation 18, to yield a colourless gum (49 mg, 100%).

$^1$H NMR (400 MHz, CDCl$_3$) δ=1.67-1.78 (m, H), 1.79-2.02 (m, 4H), 2.15-2.34 (m, 7H), 2.64-2.67 (t, 2H), 2.88-2.91 (t, 2H), 3.06-3.10 (t, 1H), 3.22-3.27 (t, 1H), 3.31-3.36 (q, 2H), 3.54-3.57 (t, 2H), 3.63-3.70 (m, 4H), 3.99 (s, 2H), 7.02 (dm, 2H), 7.54 (t, H), 8.33-8.34 (d, H), 8.35 (d, H).

MS, m/z=365 and 387 ES+ [M+H]$^+$ and [M+Na]$^+$, 365 Cl [M+H]$^+$

Preparation 30: 2-(2-aminoethoxy)-N-(3-{5-[(2S)-1-methylpyrrolidin-2-yl]pyridin-3-yl}propyl)acetamide

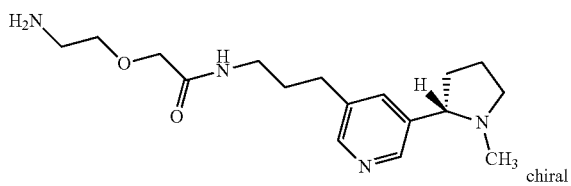 [SMILES: CN1CCC[C@H]1c1cncc(CCCNC(=O)COCCN)c1]

The title compound was prepared by the general method described above for preparation 24, starting from preparation 19, yielding a pale yellow gum (87 mg, 100%).

$^1$H NMR (400 MHz, CDCl$_3$) δ=1.70-1.97 (m, 6H), 2.17 (s, 3H), 2.18-2.23 (m, H), 2.31 (q, H), 2.67 (t, 2H), 2.94 (m, 2H), 3.08 (t, H), 3.26 (m, H), 3.35 (q, 2H), 3.56 (t, 2H), 3.98 (s, 2H), 7.35 (br, H), 7.55 (t, H), 8.34 (d, H), 8.35 (d, H).

MS, m/z=321 ES+ [M+H]$^+$

Preparation 31 5-amino-N-(3-{5-[(2S)-1-methylpyrrolidin-2-yl]pyridin-3-yl}propyl)pentanamide

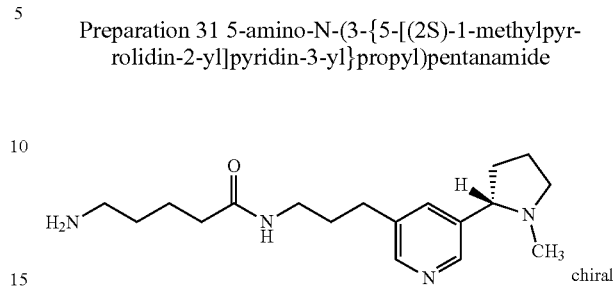

The title compound was prepared by the general method described above for preparation 24, starting from preparation 20, yielding a pale yellow gum (78 mg, 54%).

$^1$H NMR (400 MHz, CDCl$_3$) δ=1.46-1.52 (m, H), 1.64-1.72 (m, 3H), 1.81-2.02 (m, 7H), 2.15-2.24 (m, 5H), 2.31 (q, H), 2.65 (t, 2H), 2.72 (t, H), 3.07 (t, H), 3.20-3.32 (m, 4H), 5.79 (br, H), 6.25 (br, H), 7.53 (s, H), 8.33 (m, H), 8.35 (m, H).

MS, m/z=319 ES+ [M+H]$^+$

Preparation 32: 6-amino-N-(3-{5-[(2S)-1-methylpyrrolidin-2-yl]pyridin-3-yl}propyl) hexanamide

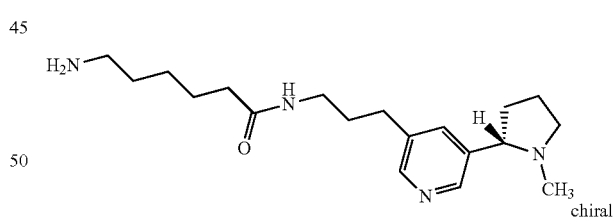

The title compound was prepared by the general method described above for preparation 24, starting from preparation 21, yielding a pale yellow gum (70 mg, 46%).

$^1$H NMR (400 MHz, CDCl$_3$) δ=1.32-1.41 (m, 2H), 1.50-1.57 (m, H), 1.59-1.70 (m, 4H), 1.81-1.85 (m, 3H), 1.87-2.01 (m, 2H), 2.15 (s, 3H), 2.15-23 (m, 3H), 2.30 (q, H), 2.63 (t, 2H), 2.765 (t, H), 3.06 (t, H), 3.19-2.29 (m, 3H).

MS, m/z=333 ES+ [M+H]$^+$

Preparation 33: 7-amino-N-(3-{5-[(2S)-1-methylpyrrolidin-2-yl]pyridin-3-yl}propyl) heptanamide

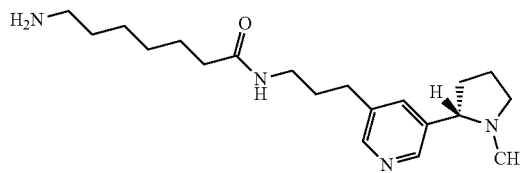

The title compound was prepared by the general method described above for preparation 24, starting from preparation 22, yielding a pale yellow gum (59 mg, 37%).

$^1$H NMR (400 MHz, CDCl$_3$) δ=1.32-1.29 (m, 3H), 1.46-1.50 (m, H), 1.61-1.66 (m, 2H), 1.70-1.74 (m, H), 1.82-1.89 (m, 3H), 1.94-2.04 (m, 3H), 2.17 (s, 3H), 2.15-2.23 (m, 3H), 2.32 (q, H), 2.65 (t, 2H), 2.71 (t, H), 3.08 (t, H), 3.18-3.33 (m, 4H), 5.58 (br, H), 5.65 (br, H), 7.53 (d, H), 8.34 (m, H), 8.36 (m, H).

MS, m/z=347 ES+ [M+H]$^+$

Preparation 34: N-(3-{2-[2-(3-aminopropoxy)ethoxy]ethoxy}propyl)-N'-(3-{5-[(2S)-1-methylpyrrolidin-2-yl]pyridin-3-yl}propyl)succinamide

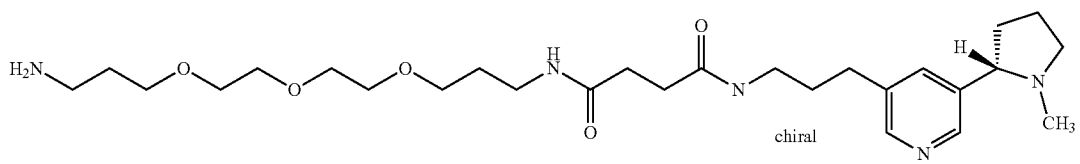 [SMILES: CN1CCC[C@H]1c1cncc(CCCNC(=O)CCC(=O)NCCCOCCOCCOCCCN)c1]

The title compound was prepared by the general method described above for preparation 24, starting from preparation 23, yielding a pale yellow gum (120 mg, 51%).

$^1$H NMR (400 MHz, CDCl$_3$) δ=1.71-1.87 (m, 6H), 1.90-2.02 (m, H), 2.16 (s, 3H), 2.17-2.24 (m, H), 2.30 (q, H), 2.40-2.51 (m, 6H), 2.61-2.67 (m, 2H), 2.87 (t, 2H), 3.22-3.29 (m, 3H), 3.31 (q, 2H), 3.51-3.65 (m, 12H), 6.85 (br, H), 6.95 (br, H), 7.53 (s, H), 8.33 (m, H), 8.35 (m, H).

MS, m/z=522 ES+ [M+H]$^+$

Preparation 35: tert-butyl (trans-4-{[2-({5-[(2S)-1-methylpyrrolidin-2-yl]pyridin-3-yl}oxy)ethyl]carbamoyl}cyclohexyl)carbamate

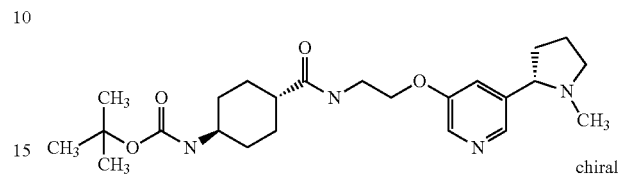

A solution of 2-({5-[(2S)-1-methylpyrrolidin-2-yl]pyridin-3-yl}oxy)ethanamine (preparation 12) (55 mg, 0.25 mmol) in 2-methyltetrahydrofuran (2 ml) was treated, with stirring, with trans-4-tert-butoxycarbonyl-cyclohexane carboxylic acid (91 mg, 0.373 mmol) followed by T3P (317 μl, 0.498 mmol) and the Et$_3$N (118 μl, 0.91 mmol). After stirring for 3 hours, the solution was treated with T3P (69 μL, 0.498 mmole). After stirring for 18 hours the solution was concentrated in vacuo and the residue was taken up in MeOH and applied to an SCX-2 cartridge which was eluted with methanol followed by ammonia in MeOH (~2M). Product containing fractions were concentrated in vacuo and the residue purified by column chromatography on silica gel eluting with EtOAc:MeOH:NH3 (gradient from 1:0:0 to 90:10:1). This material was then dissolved in DCM and treated with PS-Isocyanate resin for 3 hours then filtered and evaporated in-vacuo to give the title compound as a pale yellow gum (35 mg, 35%);

$^1$H NMR (400 MHz, CDCl$_3$) δ=1.14-1.25 (m, 2H), 1.42 (d, 9H), 1.47-1.58 (m, 2H), 1.75-1.85 (m, 3H), 1.87-2.06 (m, 4H), 2.09-2.18 (m, 1H), 2.21 (s, 3H), 2.23-2.32 (m, 1H), 2.38-2.45 (q, 1H), 3.24-3.29 (m, 3H), 3.55-3.58 (t, 2H), 4.11-4.14 (t, 2H), 7.45-7.43 (m, 1H), 8.10 (d, 1H), 8.15-8.16 (d, 1H).

MS m/z=447 ES+ [M+H]$^+$, 447 Cl [M+H]$^+$

Preparation 36: tert-butyl {2-[2-(2-{[2-({5-[(2S)-1-methylpyrrolidin-2-yl]pyridin-3-yl}oxy)ethyl]amino}-2-oxoethoxy)ethoxy]ethyl}carbamate

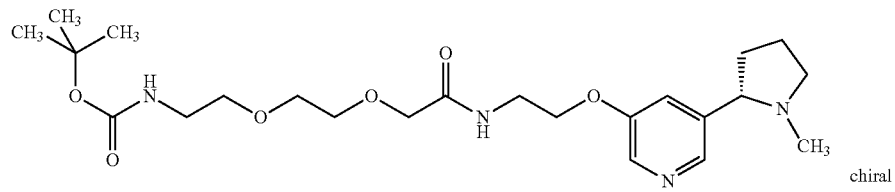 [SMILES: CN1CCC[C@H]1c1cncc(OCCNC(=O)COCCOCCNC(=O)OC(C)(C)C)c1]

The title compound was prepared by the general method described above for preparation 35, using [2-(2-tert-Butoxycarbonylamino-ethoxy)-ethoxy]-acetic acid (prepared as described in Angew. Chemie Int. Ed. (2006), 45(30), 4936-4940) instead of trans-4-tert-butoxycarbonyl-cyclohexane carboxylic acid, to yield a pale yellow gum (50 mg, 43%).

$^1$H NMR (400 MHz, CDCl$_3$) δ=1.41 (s, 9H), 1.72-1.81 (m, 1H), 1.84-2.01 (m, 2H), 2.18 (s, 3H), 2.21-2.30 (m, 1H), 2.33-2.40 (q, 1H), 3.16-3.26 (m, 4H), 3.50-3.52 (t, 2H), 3.62-3.69 (m, 6H), 4.01 (s, 2H), 4.16-4.19 (t, 2H), 7.44-7.45 (m, 1H), 8.10 (d, 1H), 8.15-8.16 (d, 1H).

MS m/z=467 ES+ [M+H]$^+$, 467 Cl [M+H]$^+$

Preparation 37: tert-butyl (2-{[2-({5-[(2S)-1-methylpyrrolidin-2-yl]pyridin-3-yl}oxy)ethyl]amino}-2-oxoethyl)carbamate

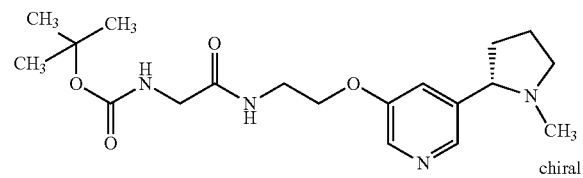 [SMILES: CN1CCC[C@H]1c1cncc(OCCNC(=O)CNC(=O)OC(C)(C)C)c1]

The title compound was prepared by the general method described above for preparation 35, using tert-butoxylcarbonylamino-acetic acid instead of trans-4-tert-butoxycarbonyl-cyclohexane carboxylic acid, to yield a pale yellow gum (50 mg, 53%).

$^1$H NMR (400 MHz, CDCl$_3$) δ=1.42 (s, 9H), 1.87-2.09 (m, 3H), 2.30-2.38 (m, 4H), 2.60-2.67 (q, 1H), 3.37-3.43 (brt, 1H), 3.52-3.56 (brt, 1H), 3.61-3.64 (t, 2H), 3.70 (s, 2H), 4.14-4.17 (t, 2H), 7.49-7.50 (m, 1H), 8.14-8.15 (d, 1H), 8.20-8.21 (d, 1H).

MS m/z=379 ES+ [M+H]$^+$, 379 Cl [M+H]$^+$

Preparation 38: tert-butyl (3-{[2-({5-[(2S)-1-methylpyrrolidin-2-yl]pyridin-3-yl}oxy)ethyl]amino}-3-oxopropyl)carbamate

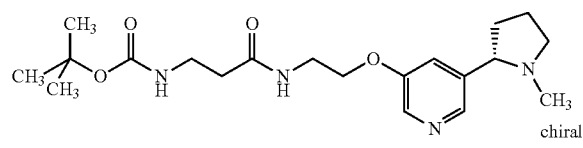 [SMILES: CN1CCC[C@H]1c1cncc(OCCNC(=O)CCNC(=O)OC(C)(C)C)c1]

The title compound was prepared by the general method described above for preparation 35, using tert-butoxylcarbonylamino-propionic acid instead of trans-4-tert-butoxycarbonyl-cyclohexane carboxylic acid, to yield a pale yellow gum (70 mg, 72%).

$^1$H NMR (400 MHz, CDCl$_3$) δ=1.39 (s, 9H), 1.75-1.84 (m, 1H), 1.87-2.04 (m, 2H), 2.21 (s, 3H), 2.23-2.31 (m, 1H), 2.37-2.47 (m, 3H), 3.24-3.33 (m, 4H), 3.58-3.61 (t, 2H), 4.12-4.15 (t, 2H), 7.44-7.45 (m, 1H), 8.10-8.11 (d, 1H), 8.16-8.17 (d, 1H).

MS m/z=393 ES+ [M+H]$^+$, 393 Cl [M+H]$^+$

Preparation 39: tert-butyl (4-{[2-({5-[(2S)-1-methylpyrrolidin-2-yl]pyridin-3-yl}oxy)ethyl]amino}-4-oxobutyl)carbamate

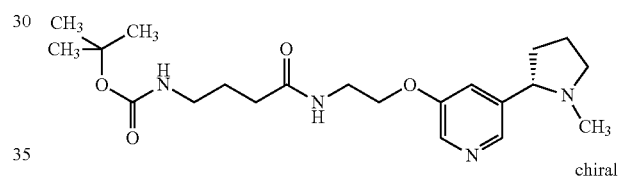

The title compound was prepared by the general method described above for preparation 35, using tert-butoxylcarbonylamino-butanoic acid instead of trans-4-tert-butoxycarbonyl-cyclohexane carboxylic acid, to yield a pale yellow gum (43 mg, 42%).

$^1$H NMR (400 MHz, CDCl$_3$) δ=1.41 (s, 9H), 1.70-1.78 (m, 2H), 1.96-2.12 (m, 3H), 2.21-2.24 (t, 2H), 2.33-2.42 (m, 4H), 2.69-2.76 (q, 1H), 3.02-3.07 (m, 2H), 3.43-3.49 (brt, 1H), 3.58-3.61 (t, 2H), 3.64-3.69 (brt, 1H), 4.15-4.18 (t, 2H), 7.51-7.52 (m, 1H), 8.16-8.17 (d, 1H), 8.23-8.24 (d, 1H).

MS m/z=407 ES+ [M+H]$^+$, 407 Cl [M+H]$^+$

Preparation 40: tert-butyl (5-{[2-({5-[(2S)-1-methylpyrrolidin-2-yl]pyridin-3-yl}oxy)ethyl]amino}-5-oxopentyl)carbamate

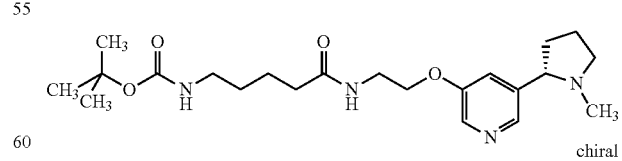

The title compound was prepared by the general method described above for preparation 35, using tert-butoxylcarbonylamino-pentanoic acid instead of trans-4-tert-butoxycarbonyl-cyclohexane carboxylic acid, to yield a pale yellow gum (49 mg, 47%).

¹H NMR (400 MHz, CDCl₃) δ=1.41-1.50 (m, 11H), 1.57-1.65 (m, 2H), 2.01-2.18 (m, 3H), 2.20-2.24 (t, 2H), 2.37-2.44 (m, 1H), 2.46 (s, 3H), 2.78-2.85 (q, 1H), 3.00-3.05 (m, 2H), 3.49-3.55 (m, 1H), 3.58-3.61 (t, 2H), 3.76-3.80 (brt, 1H), 4.15-4.16 (t, 2H), 7.55-7.56 (m, 1H), 8.18-8.19 (d, 1H), 8.25-8.26 (d, 1H).

MS m/z=421 ES+ [M+H]⁺, 421 Cl [M+H]⁺

Preparation 41: tert-butyl (6-{[2-({5-[(2S)-1-methylpyrrolidin-2-yl]pyridin-3-yl}oxy)ethyl]amino}-6-oxohexyl)carbamate

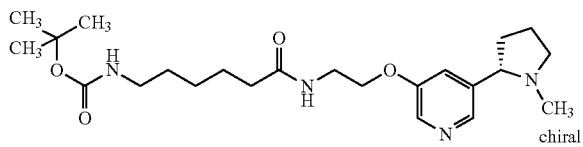 [SMILES: CN1CCC[C@H]1c1cncc(OCCNC(=O)CCCCCNC(=O)OC(C)(C)C)c1]

The title compound was prepared by the general method described above for preparation 35, using tert-butoxylcarbonylamino-hexanoic acid instead of trans-4-tert-butoxycarbonyl-cyclohexane carboxylic acid, to yield a pale yellow gum (65 mg, 60%).

¹H NMR (400 MHz, CDCl₃) δ=1.29-1.35 (m, 2H), 1.42-1.49 (m, 11H), 1.57-1.65 (m, 2H), 2.05-2.15 (m, 3H), 2.19-2.23 (t, 2H), 2.38-2.46 (m, 1H), 2.48 (s, 3H), 2.82-2.89 (m, 1H), 2.96-3.00 (t, 2H), 3.53-3.61 (m, 3H), 3.62-3.66 (brt, 1H), 4.15-4.18 (t, 2H), 7.55-7.56 (m, 1H), 8.19-8.20 (d, 1H), 8.26-8.27 (d, 1H).

MS m/z=435 ES+ [M+H]⁺, 435 Cl [M+H]⁺

Preparation 42: tert-butyl (7-{[2-({5-[(2S)-1-methylpyrrolidin-2-yl]pyridin-3-yl}oxy)ethyl]amino}-7-oxoheptyl)carbamate

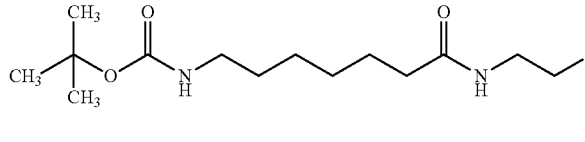

The title compound was prepared by the general method described above for preparation 35, using tert-butoxylcarbonylamino-heptanoic acid instead of trans-4-tert-butoxycarbonyl-cyclohexane carboxylic acid, to yield a pale yellow gum (67 mg, 60%).

¹H NMR (400 MHz, CDCl₃) δ=1.28-1.34 (m, 4H), 1.39-1.45 (m, 11H), 1.55-1.64 (m, 2H), 2.03-2.15 (m, 3H), 2.19-2.22 (t, 2H), 2.38-2.46 (m, 1H), 2.48 (s, 3H), 2.81-2.88 (m, 1H), 2.97-3.00 (t, 2H), 3.51-3.57 (m, 1H), 3.58-3.61 (t, 2H), 3.80-3.84 (m, 1H), 4.15-4.18 (t, 2H), 7.55-7.57 (m, 1H), 8.19 (d, 1H), 8.16 (d, 1H).

MS m/z=449 ES+ [M+H]⁺, 449 Cl [M+H]⁺

Preparation 43: tert-butyl [2-(2-{[2-({5-[(2S)-1-methylpyrrolidin-2-yl]pyridin-3-yl}oxy)ethyl]amino}-2-oxoethoxy)ethyl]carbamate

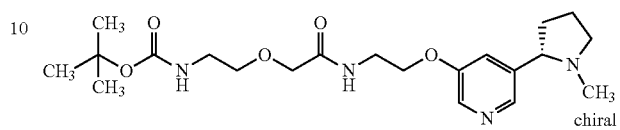

The title compound was prepared by the general method described above for preparation 35, using (2-tert-butoxycarbonylamino-ethoxy)-acetic acid instead of trans-4-tert-butoxycarbonyl-cyclohexane carboxylic acid, to yield a pale yellow gum (42 mg, 42%).

¹H NMR (400 MHz, CDCl₃) δ=1.42 (s, 9H), 2.15-2.32 (m, 3H), 2.43-2.52 (s, 1H), 2.61 (s, 3H), 3.03-3.10 (m, 1H), 3.24-3.29 (m, 2H), 3.52-3.55 (t, 2H), 3.66-3.69 (m, 3H), 3.98 (s, 2H), 4.06-4.13 (m, 1H), 4.21-4.24 (t, 2H), 7.62-7.63 (m, 1H), 8.24 (d, 1H), 8.32-8.33 (d, 1H).

MS m/z=423 ES+ [M+H]⁺, 423 Cl [M+H]⁺

Preparation 44: tert-butyl [21-({5-[(2S)-1-methylpyrrolidin-2-yl]pyridin-3-yl}oxy)-15,18-dioxo-4,7,113-trioxa-14,19-diazahenicos-1-yl]carbamate

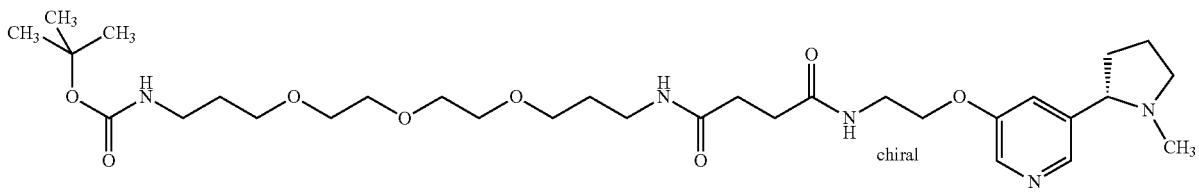 [SMILES: CN1CCC[C@H]1c1cncc(OCCNC(=O)CCC(=O)NCCCOCCOCCOCCCNC(=O)OC(C)(C)C)c1]

The title compound was prepared by the general method described above for preparation 35, using N-(3-{2-[2-(3-tert-butoxycarbonylamino-propoxy)-ethoxy]-ethoxy}-propyl)-succinamic acid instead of trans-4-tert-butoxycarbonyl-cyclohexane carboxylic acid, to yield an orange gum (80 mg, 51%).

¹H NMR (400 MHz, CDCl₃) δ=1.42 (s, 9H), 1.68-1.76 (m, 4H), 1.97-2.15 (m, 3H), 2.35-2.52 (m, 9H), 2.71-2.80 (m, 1H), 3.09-3.14 (m, 2H), 3.20-3.26 (m, 2H), 3.48-3.51 (t, 5H), 3.55-3.64 (m, 10H), 3.66-3.76 (m, 1H), 4.14-4.17 (t, 2H), 7.53-7.54 (m, 1H), 8.17-8.18 (d, 1H), 8.24-8.25 (d, 1H).

MS m/z=625 ES+ [M+H]⁺, 625 Cl [M+H]⁺

Preparation 45: tert-butyl [18-({5-[(2S)-1-methylpyrrolidin-2-yl]pyridin-3-yl}oxy)-15-oxo-3,6,9,12-tetraoxa-16-azaoctadec-1-yl]carbamate The title compound was prepared by the general method described above for preparation 35, using 3-(2-{2-[2-(2-tert-Butoxycarbonylamino-ethoxy)-ethoxy]-ethoxy}-ethoxy)-propionic acid instead of trans-4-tert-butoxycarbonyl-cyclohexane carboxylic acid, to yield an orange gum (80 mg, 56%).

¹H NMR (400 MHz, CDCl₃) δ=1.42 (s, 9H), 2.03-2.20 (m, 3H), 2.38-2.50 (m, 6H), 2.85-2.91 (m, 1H), 3.19-3.22 (m, 2H), 3.47-3.50 (t, 2H), 3.53-3.63 (m, 15H), 3.71-3.74 (t, 2H), 3.84-3.92 (m, 1H), 4.17-4.19 (t, 2H), 7.58-7.59 (m, 1H), 8.20-8.21 (d, 1H), 8.28 (d, 1H).

MS m/z=570 ES+ [M+H]⁺, 570 Cl [M+H]⁺

Preparation 46: trans-4-amino-N-[2-({5-[(2S)-1-methylpyrrolidin-2-yl]pyridin-3-yl}oxy)ethyl]cyclohexanecarboxamide

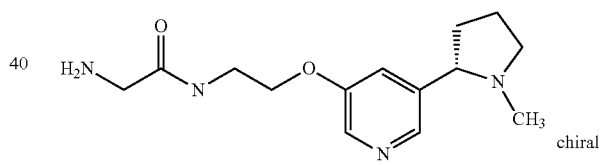

A solution of tert-butyl (trans-4-{[2-({5-[(2S)-1-methylpyrrolidin-2-yl]pyridin-3-yl}oxy)ethyl]carbamoyl}cyclohexyl)carbamate (preparation 35) (35 mg, 0.078 mmol) in DCM (3 mL) was treated with trifluoroacetic acid (1 mL). The resulting solution was stirred at ambient temperature overnight, after which time it was concentrated in vacuo. The residue was dissolved in MeOH and applied to an SCX-2 cartridge and eluted with MeOH followed by ammonia in MeOH (2M). The fractions containing product were concentrated in vacuo to give the title compound as an orange gum (17 mg, 62%).

¹H NMR (400 MHz, CDCl₃) δ=1.16-1.26 (m, 2H), 1.47-1.57 (m, 2H), 1.71-2.01 (m, 8H), 2.13-2.30 (m, 4H), 2.33-2.40 (q, 1H), 2.68-2.76 (m, 1H), 3.18-3.26 (m, 2H), 3.56-3.59 (t, 2H), 4.12-4.14 (t, 2H), 7.43-7.44 (m, 1H), 8.09-8.10 (d, 1H), 8.14-8.15 (m, 1H).

MS m/z=347 ES+ [M+H]⁺, 347 Cl [M+H]⁺

Preparation 47: 2-[2-(2-aminoethoxy)ethoxy]-N-[2-({5-[(2S)-1-methylpyrrolidin-2-yl]pyridin-3-yl}oxy)ethyl]acetamide

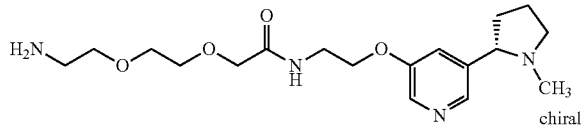 [SMILES: CN1CCC[C@H]1c1cncc(OCCNC(=O)COCCOCCN)c1]

The title compound was prepared by the general method described above for preparation 46, starting from preparation 36, to yield an orange gum (37 mg, 95%).

¹H NMR (400 MHz, CDCl₃) δ=1.72-1.81 (m, 1H), 1.84-2.03 (m, 2H), 2.18 (s, 3H), 2.22-2.30 (m, 1H), 2.34-2.41 (q, 1H), 2.83-2.86 (t, 2H), 3.19-3.26 (m, 2H), 3.54-3.57 (t, 2H), 3.65-3.71 (m, 6H), 4.02 (s, 2H), 4.16-4.19 (t, 2H), 7.44-7.45 (m, 1H), 8.10-8.11 (d, 1H), 8.15 (d, 1H).

MS m/z=367 ES+ [M+H]⁺, 367 Cl [M+H]⁺

Preparation 48: N-[2-({5-[(2S)-1-methylpyrrolidin-2-yl]pyridin-3-yl}oxy)ethyl]glycinamide

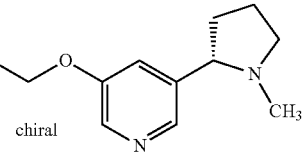

The title compound was prepared by the general method described above for preparation 46, starting from preparation 37, to yield an orange gum (37 mg, 100%).

¹H NMR (400 MHz, CDCl₃) δ=1.74-1.84 (m, 1H), 1.87-2.05 (m, 2H), 2.20 (s, 3H), 2.23-2.32 (m, 1H), 2.38-2.44 (q, 1H), 3.23-3.28 (m, 2H), 3.37 (s, 2H), 3.63-3.66 (t, 2H), 4.15-4.17 (t, 2H), 7.45-7.47 (m, 1H), 8.10-8.11 (d, 1H), 8.15-8.16 (d, 1H).

MS m/z=279 ES+ [M+H]⁺, 279 Cl [M+H]⁺

Preparation 49: N-[2-({5-[(2S)-1-methylpyrrolidin-2-yl]pyridin-3-yl}oxy)ethyl]-beta-alaninamide

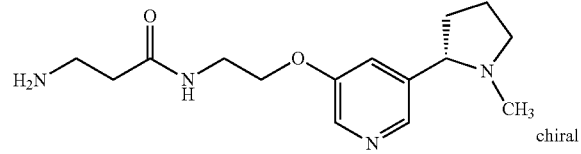 [SMILES: CN1CCC[C@H]1c1cncc(OCCNC(=O)CCN)c1]

The title compound was prepared by the general method described above for preparation 46, starting from preparation 38, to yield an orange gum (52 mg, 100%).

$^1$H NMR (400 MHz, CDCl$_3$) δ=1.72-1.81 (m, 1H), 1.84-2.03 (m, 2H), 2.18 (s, 3H), 2.21-2.30 (m, 1H), 2.33-2.44 (m, 3H), 2.93-2.96 (t, 2H), 3.16-3.26 (m, 2H), 3.60-3.62 (t, 2H), 4.13-4.16 (t, 2H), 7.43-7.44 (m, 1H), 8.10 (d, 1H), 8.14-8.15 (d, 1H).

MS m/z=293 ES+ [M+H]$^+$, 293 Cl [M+H]$^+$

Preparation 50: 4-amino-N-[2-({5-[(2S)-1-methylpyrrolidin-2-yl]pyridin-3-yl}oxy)ethyl]butanamide

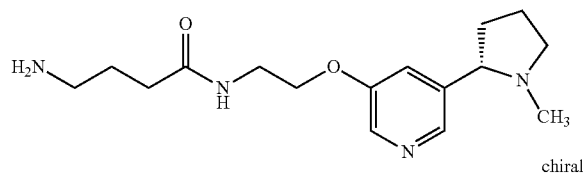 [SMILES: CN1CCC[C@H]1c1cncc(OCCNC(=O)CCCN)c1]

The title compound was prepared by the general method described above for preparation 46, starting from preparation 39, to yield an orange gum (28 mg, 88%).

$^1$H NMR (400 MHz, CDCl$_3$) δ=1.73-1.82 (m, 3H), 1.84-2.03 (m, 2H), 2.18 (s, 3H), 2.21-2.30 (m, 3H), 2.33-2.40 (q, 1H), 2.68-2.72 (t, 2H), 3.18-3.26 (m, 2H), 3.58-3.61 (t, 2H), 4.12-4.15 (t, 2H) 7.43-7.44 (m, 1H), 8.10 (d, 1H), 8.14-8.15 (d, 1H).

MS m/z=307 ES+ [M+H]$^+$, 307 Cl [M+H]$^+$

Preparation 51: 5-amino-N-[2-({5-[(2S)-1-methylpyrrolidin-2-yl]pyridin-3-yl}oxy)ethyl]pentanamide

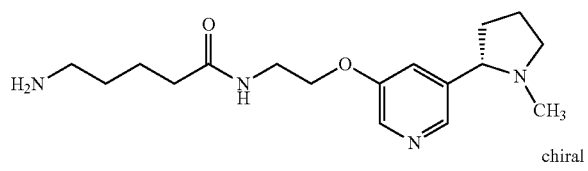 [SMILES: CN1CCC[C@H]1c1cncc(OCCNC(=O)CCCCN)c1]

The title compound was prepared by the general method described above for preparation 46, starting from preparation 40, to yield an orange gum (30 mg, 81%).

$^1$H NMR (400 MHz, CDCl$_3$) δ=1.48-1.56 (m, 2H), 1.61-1.68 (m, 2H), 1.71-1.81 (m, 1H), 1.85-2.03 (m, 2H), 2.18 (s, 3H), 2.22-2.30 (m, 3H), 2.33-2.40 (q, 1H), 2.68-2.72 (t, 2H), 3.18-3.26 (m, 2H), 3.58-3.61 (t, 2H), 4.12-4.15 (t, 2H), 7.43-7.44 (m, 1H), 8.10 (d, 1H), 8.14-8.15 (d, 1H).

MS m/z=321 ES+ [M+H]$^+$, 321 Cl [M+H]$^+$

Preparation 52: 6-amino-N-[2-({5-[(2S)-1-methylpyrrolidin-2-yl]pyridin-3-yl}oxy)ethyl]hexanamide

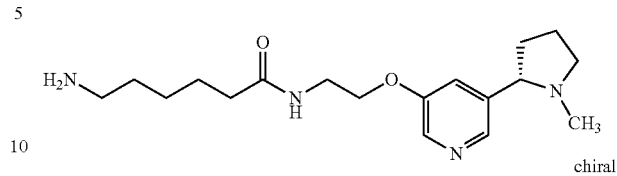

The title compound was prepared by the general method described above for preparation 46, starting from preparation 41, to yield an orange gum (38 mg, 76%).

$^1$H NMR (400 MHz, CDCl$_3$) δ=1.31-1.39 (m, 2H), 1.48-1.55 (m, 2H), 1.59-1.66 (m, 2H), 1.72-1.81 (m, 1H), 1.84-2.03 (m, 2H), 2.18 (s, 3H), 2.21-2.30 (m, 3H), 2.33-2.40 (q, 1H), 2.65-2.69 (t, 2H), 3.18-3.26 (m, 2H), 3.57-3.60 (t, 2H), 4.15-4.12 (t, 2H), 7.43-7.44 (m, 1H), 8.09-8.10 (d, 1H), 8.14-8.15 (d, 1H).

MS m/z=335 ES+ [M+H]$^+$, 335 Cl [M+H]$^+$

Preparation 53: 7-amino-N-[2-({5-[(2S)-1-methylpyrrolidin-2-yl]pyridin-3-yl}oxy)ethyl]heptanamide

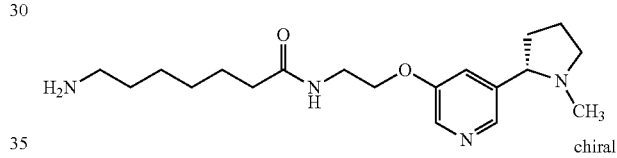

The title compound was prepared by the general method described above for preparation 46, starting from preparation 42, to yield an orange gum (37 mg, 72%).

$^1$H NMR (400 MHz, CDCl$_3$) δ=1.32-1.37 (m, 4H), 1.44-1.51 (m, 2H), 1.57-1.65 (m, 2H), 1.72-1.82 (m, 1H), 1.83-2.03 (m, 2H), 2.18-2.30 (m, 6H), 2.33-2.40 (q, 1H), 2.65-2.68 (t, 2H), 3.18-3.26 (m, 2H), 3.57-3.60 (t, 2H), 4.12-4.15 (t, 2H), 7.43-7.44 (m, 1H), 8.09-8.10 (d, 1H), 8.14-8.15 (d, 1H).

MS m/z=349 ES+ [M+H]$^+$, 349 Cl [M+H]$^+$

Preparation 54: 2-(2-aminoethoxy)-N-[2-({5-[(2S)-1-methylpyrrolidin-2-yl]pyridin-3-yl}oxy)ethyl]acetamide

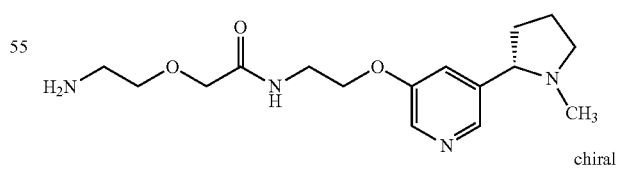

The title compound was prepared by the general method described above for preparation 46, starting from preparation 43, to yield an orange gum (27 mg, 84%).

$^1$H NMR (400 MHz, CDCl$_3$) δ=1.72-1.82 (m, 1H), 1.84-2.03 (m, 2H), 2.18 (s, 3H), 2.22-2.30 (m, 1H), 2.34-2.40 (q, 1H), 2.86-2.89 (t, 2H), 3.18-3.26 (m, 2H), 3.55-3.58 (t, 2H), 3.66-3.68 (t, 2H), 4.00 (s, 2H), 4.16-4.19 (t, 2H), 7.44-7.45 (m, 1H), 8.10 (d, 1H), 8.15 (d, 1H).

MS m/z=323 ES+ [M+H]+, 323 Cl [M+H]+

Preparation 55: N-(3-{2-[2-(3-aminopropoxy)ethoxy]ethoxy}propyl)-N'-[2-({5-[(2S)-1-methylpyrrolidin-2-yl]pyridin-3-yl}oxy)ethyl]succinamide

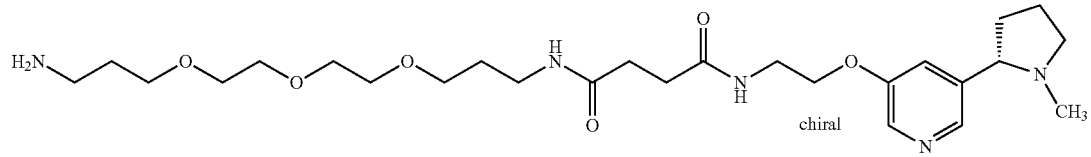 [SMILES: CN1CCC[C@H]1c1cncc(OCCNC(=O)CCC(=O)NCCCOCCOCCOCCCN)c1]

The title compound was prepared by the general method described above for preparation 46, starting from preparation 44, to yield an orange gum (59 mg, 88%).

¹H NMR (400 MHz, CDCl₃) δ=1.70-1.80 (m, 5H), 1.86-2.03 (m, 2H), 2.18 (s, 3H), 2.21-2.30 (m, 1H), 2.33-2.40 (q, 1H), 2.44-2.52 (m, 4H), 2.76-2.80 (t, 2H), 3.18-3.26 (m, 4H), 3.48-3.51 (t, 2H), 3.55-3.63 (m, 12H), 4.11-4.14 (t, 2H), 7.43-7.44 (m, 1H), 8.10 (d, 1H), 8.15 (d, 1H).

MS m/z=524 ES+ [M+H]+, 524 Cl [M+H]+

Preparation 56: 1-amino-N-[2-({5-[(2S)-1-methylpyrrolidin-2-yl]pyridin-3-yl}oxy)ethyl]-3,6,9,12-tetraoxapentadecan-15-amide

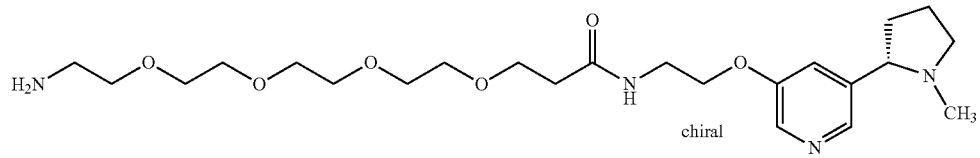 [SMILES: CN1CCC[C@H]1c1cncc(OCCNC(=O)CCOCCOCCOCCOCCN)c1]

The title compound was prepared by the general method described above for preparation 46, starting from preparation 45, to yield an orange gum (55 mg, 85%).

¹H NMR (400 MHz, CDCl₃) δ=1.71-1.81 (m, 1H), 1.84-2.03 (m, 2H), 2.18 (s, 3H), 2.22-2.30 (m, 1H), 2.33-2.40 (q, 1H), 2.45-2.48 (t, 2H), 2.78-2.80 (t, 2H), 3.18-3.25 (m, 2H), 3.50-3.53 (t, 2H), 3.58-3.62 (m, 14H), 3.71-3.74 (t, 2H), 4.13-4.15 (t, 2H), 7.44-7.45 (m, 1H), 8.10 (d, 1H), 8.15-8.16 (d, 1H).

MS m/z=469 ES+ [M+H]+, 469 Cl [M+H]+

Preparation 57: 4-Mercapto-N-[2-({5-[(2S)-1-methylpyrrolidin-2-yl]pyridin-3-yl}oxy)ethyl]butanamide

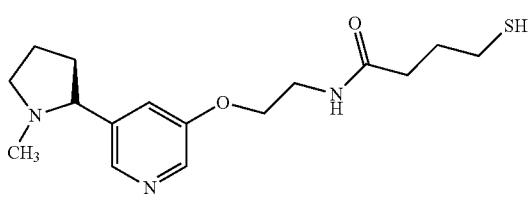

A solution of 2-({5-[(2S)-1-methylpyrrolidin-2-yl]pyridin-3-yl}oxy)ethanamine (preparation 12) (1100 mg, 4.971 mmol), in water (10 ml), was treated with γ-thiobutyrolactone (861 ul, 9.94 mmol) and the reaction mixture was heated to 60° C. overnight. It was then evaporated in vacuo to leave a colourless gum, which was pre-adsorbed onto silica from MeOH. This was then chromatographed on a 40 g ISCO column, eluting with EtOAc to EtOAc:MeOH:NH3 80:20:1. The appropriate fractions were evaporated in vacuo to give the title compound as a colourless gum, 690 mg. Yield=43%.

¹H NMR (400 Mhz, CD₃OD): δ=1.77-2.06 (m, 6H), 2.22-2.35 (m, 6H), 2.41-2.51 (m, 3H), 3.26-3.32 (m, H), 3.58-3.61 (t, 2H), 4.13-4.15 (t, 2H), 7.45-7.47 (m, H), 8.11-8.12 (d, H), 8.17 (d, H). MS m/z=324 ES+ [M+H]+ and 322 Cl— [M−H]

EXAMPLES

Example 1

The hapten of preparation 4 was coupled to diphtheria toxoid protein using the following procedure.

a) The hapten was obtained as a yellow oil and stored at 2-8° C. until the day of use (for up to one week, longer storage was at −20° C.). This oil was dissolved in either Dulbeccos' Phosphate Buffered Saline without Ca or Mg (DPBS) or deionised water at 50 mg hapten per ml solution. The result was a yellow-brown suspension or solution.

b) Separately, an aliquot of concentrated diphtheria toxoid (DT) was obtained and using a gel filtration desalting column (Bio-Rad), the buffer of the DT was changed to DPBS. The eluate from the column was a 4 ml solution at approximately 11 mg/ml as determined by the Bradford assay (Coomassie Brilliant Blue reagent, Pierce Chemical) using a bovine serum albumin standard curve. An aliquot of this was diluted with further DPBS to give a 4 ml solution at 5 mg/ml protein in DPBS.

c) This aliquot of DT was reacted with succinic anhydride to create a modified succinylated diphtheria toxoid. The 4 ml aliquot of DT in DPBS was combined with 80 mg succinic anhydride as a solid, and placed on a tube roller to provide gentle agitation at room temperature for 3 h. It was noted that using this method, the end product was not a clear solution. At the end of the 3 h reaction time, the aliquot was applied to a gel filtration desalting column and eluted into DPBS, to remove unreacted small molecule components. This increased the volume of the sample to 6 ml total.

d) 28 mg of sulfo-N-hydroxysuccinimide (s-NHS), as a solid, were added to the 6 ml succinylated DT aliquot, and s-NHS was allowed to dissolve by inverting the tube and gentle mixing. Then 28 mg of 1-ethyl-3-(3-dimethylaminopropyl) carbodiimide hydrochloride (EDC) were added to the mixture, as a solid, and allowed to dissolve by inverting the tube and gentle mixing. The reaction mixture (succinylated DT/EDC/s-NHS) was incubated at room temperature for 10 min, 200 µl of the hapten solution prepared above were added and the reaction mixture was briefly stirred using a Vortex to mix.

e) The mixture was reacted for 3 to 4 h with gentle agitation on a tube roller, at room temperature. At the end of the reaction time, the aliquot was applied to a gel filtration desalting column and eluted into DPBS, to remove unreacted small molecule components. This increased the volume of the conjugate sample to 8 ml total. This 8 ml eluate was then concentrated using 3 k MWCO centrifugal ultrafilters (Millipore) to approx 3.0-3.5 ml.

f) Using a bovine serum albumin standard, the final conjugate was analysed for protein content using the Bradford (Pierce Coomassie Brilliant Blue reagent) assay, and the final concentration determined as 2.3 mg/ml. The conjugate was analysed for hapten incorporation using the ultraviolet spectroscopy in the 250-270 nm region versus an unconjugated control normalised for protein content, and was found to more strongly antibodiesorb in this region compared with the native toxoid. The conjugate was also analysed by SDS-PAGE electrophoresis and for endotoxin content using the LAL assay. Finally, a 100 µg sample of the conjugate was hydrolysed and analysed using reversed-phase HPLC to determine the number of haptens incorporated per protein molecule. The hapten-DT conjugate was found to have 19 haptens per protein monomer g) Finally the sample was sterile filtered through a 0.22 μm syringe filter and aseptically subdivided into 0.5 ml aliquots. These aseptic aliquots were stored at −80° C. until shipping to the study location on dry ice.

Example 2

The hapten of preparation 12 was coupled to diphtheria toxoid protein using the general procedure described above for example 1, with the following changes: in step d), 186 μl of the hapten solution were added to the reaction mixture; and in step f), the final concentration was determined as 3.3 mg/ml, and the hapten-DT conjugate was found to have 13 haptens per protein monomer.

Example 3

The hapten of preparation 7 was coupled to diphtheria toxoid protein using the general procedure described above for example 1, with the following changes in steps c, e and f.

In step c), a 3 ml portion of the aliquot was applied to a gel filtration desalting column and eluted into DPBS, to remove unreacted small molecule components, whereby the volume of the purified sample was increased to 4 ml total; step d) was performed as follows: 80 μl of the hapten solution were added to the 4 ml succinylated DT aliquot, and inverted gently to mix. Then, 28 mg of sulfo-N-hydroxysuccinimide (s-NHS) were added to the mixture, as a solid, and allowed to dissolve by inverting the tube and gentle mixing. Finally, 28 mg of 1-ethyl-3-(3-dimethylaminopropyl) carbodiimide hydrochloride (EDC) were added to the mixture, as a solid, and allowed to dissolve by inverting the tube and gentle mixing.

In step e), the mixture was reacted for 2 h, the volume of the conjugate sample was increased to 6 ml total after elution, and the 6 ml eluate was then concentrated using 10 k MWCO centrifugal ultrafilters (Millipore) to approx 2.5-3.0 ml.

In step f), the final concentration was determined as 2.4 mg/ml, and the hapten-DT conjugate was found to have 14.5 haptens per protein monomer.

Example 4

The hapten of preparation 8 was coupled to diphtheria toxoid protein using the general procedure described above for example 1, with the following changes: step d) was performed as follows: 120 μl of the hapten solution were added to the 6 ml succinylated DT aliquot. The mixture was stirred briefly with a Vortex. Then 28 mg of sulfo-N-hydroxysuccinimide (s-NHS) were added, as a solid, and allowed to dissolve by inverting the tube and gentle mixing. Finally 28 mg of 1-ethyl-3-(3-dimethylaminopropyl) carbodiimide hydrochloride (EDC) were added to the mixture, as a solid, and allowed to dissolve by inverting the tube and gentle mixing; and in step f), the final concentration was determined as 2.5 mg/ml, and the hapten-DT conjugate was found to have 19.3 haptens per protein monomer.

Example 5

The hapten-spacer conjugates from preparations 24 to 34 and 46 to 56 were coupled to diphtheria toxoid protein as described in the method below.

a) The hapten-spacer conjugates were obtained as a yellow oil and stored at 2 to 8° C. until the day of use (for up to one week, longer storage was at −20° C.). This oil was dissolved in Dulbeccos' Phosphate Buffered Saline without Ca or Mg (DPBS) at 50 mg hapten per ml solution. The result was a yellow-brown suspension or solution. Preparation 33 did not dissolve fully in deionised water, and so was further dissolved to 50% methanol to a final concentration of 25 mg hapten-spacer conjugate per ml solution b) Separately, an aliquot of concentrated diphtheria toxoid (DT) was obtained and using a gel filtration desalting column (Bio-Rad), the buffer of the DT was changed to DPBS. The eluate from the column was a 4 ml solution at approximately 11 mg/ml as determined by the Bradford assay (Coomassie Brilliant Blue reagent, Pierce Chemical) using a bovine serum albumin standard curve. An aliquot of this was diluted with further DPBS to give a 2 ml solution at 5 mg/ml protein in DPBS.

c) This aliquot of DT was reacted with succinic anhydride to create a modified succinylated diphtheria toxoid. The 2 ml aliquot of DT in DPBS was combined with 40 mg succinic anhydride as a solid, and placed on a tube roller to provide gentle agitation at room temperature for 3 hours. It was noted that using this method, the end product was not a clear solution. At the end of the 3 hour reaction time, the aliquot was applied to a gel filtration desalting column and eluted into DPBS, to remove unreacted small molecule components. This increased the volume of the sample to 3 ml total.

d) 9 mg of sulfo-N-hydroxysuccinimide (s-NHS), as a solid, were added to the 3 ml DT aliquot, and the s-NHS was allowed to dissolve by inverting the tube and gentle mixing. Then 9 mg of 1-ethyl-3-(3-dimethylaminopropyl) carbodiimide hydrochloride (EDC) were added to the mixture, as a solid, and allowed to dissolve by inverting the tube and gentle mixing. 50 μl of the hapten-spacer conjugate solution prepared above (100 ul for preparation 33) were added to the reaction mixture (succinylated DT/EDC/s-NHS)

e) The mixture was reacted for 3 to 4 hours, with gentle agitation, on a tube roller, at room temperature. At the end of the reaction time, the aliquot was applied to a gel filtration desalting column and eluted into DPBS, to remove unreacted small molecule components. This increased the volume of the conjugate sample to 4 ml total.

f) Using a bovine serum albumin standard, the final conjugate was analysed for protein content using the Bradford (Pierce Coomassie Brilliant Blue reagent) assay, and the final concentration was determined as indicated in table 1. The conjugate was analysed for hapten incorporation using ultraviolet spectroscopy in the 250 to 270 nm region versus an unconjugated control, normalised for protein content, and was found to more strongly antibodiesorb in this region compared with the native toxoid. The conjugate was also analysed by SDS-PAGE electrophoresis and for endotoxin content using the LAL assay. Finally, a 100 μg sample of the conjugate was hydrolysed and analysed using reversed-phase HPLC to determine the number of haptens incorporated per protein molecule. The hapten loading for the tested samples is detailed below in tables 1 and 2.

g) Finally the sample was sterile filtered through a 0.22 μm syringe filter and aseptically subdivided into 1.0 ml aliquots. These aseptic aliquots were stored at –80° C. until shipping to the study location on dry ice.

TABLE 1

| Conjugate | protein conc. (mg/ml) | Hapten load |
| --- | --- | --- |
| DT-hapten-spacer preparation 24 | 1.69 | 11 |
| DT-hapten-spacer preparation 25 | 1.82 | 21 |
| DT-hapten-spacer preparation 26 | 1.84 | 22 |
| DT-hapten-spacer preparation 27 | 2.22 | 16 |
| DT-hapten-spacer preparation 28 | 1.91 | 16 |
| DT-hapten-spacer preparation 29 | 1.60 | 19 |
| DT-hapten-spacer preparation 30 | 1.81 | 14 |
| DT-hapten-spacer preparation 31 | 2.18 | 15 |
| DT-hapten-spacer preparation 32 | 1.62 | 15 |
| DT-hapten-spacer preparation 33 | 1.51 | 11 |
| DT-hapten-spacer preparation 34 | 1.78 | 14 |

TABLE 2

| Conjugate | protein conc. (mg/ml) | Hapten load |
| --- | --- | --- |
| DT-hapten-spacer preparation 46 | 1.39 | 3.6 |
| DT-hapten-spacer preparation 47 | 1.56 | 23.6 |
| DT-hapten-spacer preparation 48 | 1.43 | 22.8 |
| DT-hapten-spacer preparation 49 | 1.41 | 19.2 |
| DT-hapten-spacer preparation 50 | 1.58 | 19.7 |
| DT-hapten-spacer preparation 51 | 1.48 | 14.2 |
| DT-hapten-spacer preparation 52 | 1.57 | 11 |
| DT-hapten-spacer preparation 53 | 1.60 | 12.1 |
| DT-hapten-spacer preparation 54 | 1.89 | 29.3 |
| DT-hapten-spacer preparation 55 | 1.32 | 12.6 |
| DT-hapten-spacer preparation 56 | 1.45 | 20.9 |

Example 6

Haptens with a reactive amine group can also be conjugated to diphtheria toxoid without the addition of succinic anhydride. An example of the hapten of preparation 12 conjugated to diphtheria toxoid is detailed below, but this can also be performed with preparations 4, 7, 8, 24-34 and 46-56.

a) The hapten was obtained as a yellow oil and stored at 2 to 8° C. until the day of use (for up to one week, longer storage was at −20° C.). This oil was dissolved in Dulbeccos' Phosphate Buffered Saline without Ca or Mg (DPBS) at 50 mg hapten per ml solution. The result was a yellow-brown suspension or solution.

b) Separately, an aliquot of concentrated diphtheria toxoid (DT) was obtained and using a gel filtration desalting column (Bio-Rad), the buffer of the DT was changed to DPBS. The eluate from the column was a 4 ml solution at approximately 11 mg/ml as determined by the Bradford assay (Coomassie Brilliant Blue reagent, Pierce Chemical) using a bovine serum albumin standard curve. An aliquot of this was diluted with further DPBS to give a 2 ml solution at 5 mg/ml protein in DPBS.

c) 9 mg of sulfo-N-hydroxysuccinimide (s-NHS), as a solid, were added to the 2 ml DT aliquot, and the s-NHS was allowed to dissolve by inverting the tube and gentle mixing. Then 9 mg of 1-ethyl-3-(3-dimethylaminopropyl) carbodiimide hydrochloride (EDC) were added to the mixture, as a solid, and allowed to dissolve by inverting the tube and gentle mixing. 50 μl of the hapten solution prepared above were added to the reaction mixture (DT/EDC/s-NHS). At this stage the pH was adjusted down to pH 5.6 with dropwise addition of 1M HCl.

d) The mixture was reacted for 3 to 4 hours with gentle agitation, on a tube roller, at room temperature. At the end of the reaction time, the aliquot was applied to a gel filtration desalting column and eluted into DPBS, to remove unreacted small molecule components. This increased the volume of the conjugate sample to 3 ml total.

e) Using a bovine serum albumin standard, the final conjugate was analysed for protein content using the Bradford (Pierce Coomassie Brilliant Blue reagent) assay, and the final concentration determined as 3.01 mg/ml. The conjugate was analysed for hapten incorporation using ultraviolet spectroscopy in the 280 nm region versus an unconjugated control normalised for protein content, and was found to more strongly antibodiesorb in this region compared with the native toxoid. The conjugate was also analysed by SDS-PAGE electrophoresis and for endotoxin content using the LAL assay. Finally, a 100 μg sample of the conjugate was hydrolysed and analysed using reversed-phase HPLC to determine the number of haptens incorporated per protein molecule. The hapten-DT conjugate was found to have 11.6 haptens per protein monomer g) Finally the sample was sterile filtered through a 0.22 μm syringe filter and aseptically subdivided into 1.0 ml aliquots. These aseptic aliquots were stored at −80° C. until shipping to the study location on dry ice.

Example 7

Preparation 12 can also be coupled to $CRM_{197}$, as well as to diphtheria toxoid. An example of such as conjugation is given below. Although not shown, the same process can also be applied to other amine containing haptens such as 4, 7, 8, 24-34 and 46-56.

a) The hapten from preparation 12, was obtained as a yellow oil and stored at −20° C. This oil was dissolved in Dulbeccos' Phosphate Buffered Saline without Ca or Mg (DPBS) at 50 mg hapten per ml solution. The result was a yellow-brown suspension or solution.

b) Separately, a 20 ml aliquot of concentrated $CRM_{197}$ (5.91 mg/ml) was thawed from −80° C. to 2-8° C. An 8.62 ml aliquot of thawed material was taken and diluted with 1.38 ml of DPBS to give a 10 ml solution at 5 mg/ml protein in DPBS.

c) 500 μl of the hapten solution prepared above was added to the 10 ml $CRM_{197}$ solution, this was added slowly and dropwise then left to react on a tube roller for 5 mins.

d) After this time, 90 mg of sulfo-N-hydroxysuccinimide (s-NHS) as a solid, was then added to the 10 ml $CRM_{197}$ solution. The s-NHS was allowed to dissolve by inverting the tube with gentle mixing. The solution was then left to react on a tube roller for 5 mins.

e) After 5 mins, 90 mg of 1-ethyl-3-(3-dimethylaminopropyl) carbodiimide hydrochloride (EDC) was added to the $CRM_{197}$ solution, again as a solid, and this was allowed to dissolve by inverting the tube with gentle mixing. At this stage the pH was adjusted down to pH 5.6 with dropwise addition of 1M HCl.

f) The reaction mixture was then transferred to a cold room (2-8° C.), and left to react on a tube roller for 6 hours.

g) At the end of the reaction time the sample was desalted into dPBS using 5×NAP25 columns to remove excess un-reacted reagents (ON: 2 ml, OFF: 3 ml). The final volume was increased to 15 ml.

h) Using a bovine serum albumin standard, the final conjugate was analysed for protein content using the Bradford (Pierce Coomassie Brilliant Blue reagent) assay, and the final concentration determined as 2.88 mg/ml. The conjugate was analysed for hapten incorporation using ultraviolet spectroscopy in the 280 nm region versus an unconjugated control normalised for protein content, and was found to more strongly antibodiesorb in this region compared with the native toxoid. The conjugate was also analysed by SDS-PAGE electrophoresis and for endotoxin content using the LAL assay. Finally, a 100 µg sample of the conjugate was hydrolysed and analysed using reversed-phase HPLC to determine the number of haptens incorporated per protein molecule. The hapten-$CRM_{197}$ conjugate was found to have 8.0 haptens per protein monomer i) Finally the sample was sterile filtered through a 0.22 µm syringe filter and aseptically subdivided into 1.0 ml aliquots. These aseptic aliquots were stored at −80° C. until shipping to the study location on dry ice.

Example 8

It was found that by increasing the sNHS/EDC concentration of the reaction mix, the amount of hapten loaded onto the carrier protein could be controlled. An example of a conjugation of preparation 7 to diphtheria toxoid is shown below. The method is as described for example 6 with the following changes in steps c and e.

In step c): at this stage the amount of sulfo-N-hydroxysuccinimide (s-NHS) and 1-ethyl-3-(3-dimethylaminopropyl) carbodiimide hydrochloride (EDC) added to the 2 ml aliquot of desalted DT can be varied. In this experiment, 9 mg of sNHS and EDC was added to one aliquot (this is referred to as condition 2) and 36 mg of sNHS and EDC was added to another aliquot (this is referred to as condition 4). The samples were not pH adjusted down to pH 5.6 with dropwise addition of 1M HCl.

In step e): for the conjugate made using condition 2, the final concentration was determined as 3.14 mg/ml, and the hapten-DT conjugate was found to have 8.3 haptens per protein monomer. For the conjugate made using condition 4, the final concentration was determined as 2.46 mg/ml, and the hapten-DT conjugate was found to have 13.2 haptens per protein monomer.

Example 9

Preparation of thiolated hapten-spacer conjugates onto $CRM_{197}$ and formalin inactivated Diphtheria Toxoid (DT) via bromoacetic acid N-hydroxysuccinimide ester (BAANS) conjugation chemistry.

a) 3 ml of $CRM_{197}$ (17.73 mg at 5.91 mg/ml) and 3 ml of DT (24 mg at 8 mg/ml) were thawed and desalted into 100 mM Phosphate buffer, pH 8.0, using 10 DG desalting columns (Pierce) (on: 3 ml, off: 4 ml). The concentration was adjusted to 4 mg/ml using the same buffer.

b) A 1 ml aliquot of the desalted $CRM_{197}$ and DT samples was taken and cooled to 2-8° C.

c) 20 mg of the hapten-spacer conjugate of preparation 57 was dissolved in 300 ul DMSO and 700 ul dPBS to a final concentration of 20 mg/ml.

d) 500 ul (10 mg) of the hapten-spacer conjugate solution was added to 500 ul of prewashed TCEP ((tris(2-carboxyethyl)phosphine)) gel (Pierce) and incubated for 3 hours with agitation at room temperature. The remaining hapten solution was frozen at −20° C. for long term storage.

e) 90 minutes into step (d), 10 mg of BAANS (Sigma) was dissolved in 500 ul DMSO to a final concentration of 20 mg/ml.

f) 1.5 mg (75 ul) of BAANS was added to 1 ml of DT/$CRM_{197}$, slowly and dropwise (at 4 mg/ml). It was reacted for 90 mins at <11° C. (0.375 mg BAANS added per mg $CRM_{197}$/DT).

g) After 90 mins, still operating at <11° C., the bromoacetylated $CRM_{197}$/DT was desalted into cold 100 mM sodium carbonate/bicarbonate buffer, pH 9.1, using a NAP10 column (1 ml on, 1.5 ml off).

h) The hapten-spacer conjugate was aspirated from the TCEP gel, and 250 ul (5 mg) of the hapten-spacer conjugate was added into both activated $CRM_{197}$/DT samples, again slowly and dropwise, with mixing to prevent concentration gradients from forming.

i) After the hapten-spacer conjugate was added, the pH was checked and adjusted to 9.1 with dropwise addition of 0.1M NaOH/HCl if required.

j) The reaction mixture was kept in the antibodiesence of light, with mixing, for 18 hours.

k) After this time, 2 ul N-acetyl cysteamine (NAC) was added to each reaction mixture and reacted, again in antibodiesence of light, for 3 hours with agitation (0.5 ml per g $CRM_{197}$/DT).

l) After reaction, it was desalted into Dulbecco's PBS using a 10 DG desalting column (BioRad) (3 ml on, 4 ml off).

m) Finally the sample was sterile filtered through a 0.22 µm syringe filter and aseptically aliquoted. These aseptic aliquots were stored at 2-8° C. until shipping to the study location.

n) Using a bovine serum albumin standard, the final conjugate was analysed for protein content using the Bradford (Pierce Coomassie Brilliant Blue reagent) assay and the final concentration was determined as 1.59 mg/ml. The conjugate was also analysed by SDS-PAGE electrophoresis and for endotoxin content using the LAL assay. Finally, a 150 µg sample of the conjugate was hydrolysed and analysed using reversed-phase HPLC to determine the number of haptens incorporated per protein molecule. The hapten —$CRM_{197}$ conjugate was found to have 11.6 haptens per protein monomer Example 10

It was found that by increasing the BAANS concentration of the reaction mix, the amount of hapten/hapten-spacer conjugate loaded onto the carrier protein could be controlled. An example of a conjugation of preparation 57 to $CRM_{197}$ is shown below.

a) 9 ml of $CRM_{197}$ (53.19 mg at 5.91 mg/ml) was thawed and desalted into 100 mM phosphate buffer, pH 8.0, using 10 DG desalting columns (BioRad) (on: 3 ml, off: 4 ml). The concentration was adjusted to 4 mg/ml using the same buffer.

b) 30 mg of the hapten-spacer conjugate of preparation 57 was dissolved in 1.5 ml DMSO (final conc. 20 mg/ml).

c) 1 ml TCEP gel (Pierce) was prepared by washing twice in dulbecco's PBS, before 1.5 ml of the hapten-spacer conjugate containing solution was added. This was then incubated at 2-8° C. on a rotating platform for 2 hours.

d) After 1 hour of the TCEP incubation, 10 ml of 4 mg/ml $CRM_{197}$ solution was split into 5×2 ml aliquots in separate reaction vessels, and stored in a cold room for 30 mins to adjust the temperature of the solution to 2-8° C. All future steps were performed at 2-8° C.

e) At the same time, a stock solution of BAANS was prepared by dissolving 20 mg BAANS in 1 ml DMSO. The 5 reaction vessels were labelled as either condition 1, 2, 3, 4 or 5. After the temperature of the $CRM_{197}$ aliquots was adjusted to 2-8° C., varying amounts of BAANS solution (50 ul, 100 ul, 150 ul, 225 ul and 300 ul) was added to the 5×2 ml reaction vessels, as indicated in table 2. The BAANS solution was added slowly (drop-wise) and with mixing.

f) The aliquots were reacted for 30 mins at 2-8° C. on a rotating platform.

g) After the 30 min incubation, 5×2 ml bromoacetylated $CRM_{197}$ was desalted into 100 mM sodium carbonate/bicarbonate buffer pH 9.1 using NAP25 (Gibco) columns (ON: 2 ml, OFF: 3 ml).

h) The TCEP gel was spun out from the hapten samples and 5.6 mg (280 ul) of the hapten-spacer conjugate was added (slowly, dropwise) with mixing, to each of the desalted bromoacetylated $CRM_{197}$ samples. The reaction vessels were covered in foil, to protect the contents from light.

i) The mixtures were reacted for 18 hours on a rotating platform j) Unreacted BrAc groups were quenched by adding 0.5 ml NAC per g $CRM_{197}$ (therefore 4 ul per reaction) to the reaction mixture. The mixture was allowed to react for 3 hours on a rotating platform (still covered in foil to protect from light)

k) Finally, each reaction was desalted into dulbecco's PBS using DG10 columns (ON: 3 ml, OFF: 4 ml). Final volume was 4 ml.

l) The samples were sterile filtered through a 0.22 μm syringe filter and aseptically aliquoted. These aseptic aliquots were stored at 2-8° C. until shipping to the study location.

m) Using a bovine serum albumin standard, the final conjugates were analysed for protein content using the Bradford (Pierce Coomassie Brilliant Blue reagent) assay and the final concentration was determined as shown in Table 3. The conjugates were also analysed by SDS-PAGE electrophoresis, and for endotoxin content, using the LAL assay. Finally, a 450 μg sample of each conjugate was hydrolysed and analysed using reversed-phase HPLC(N=3) to determine the number of haptens incorporated per protein molecule (hapten load data shown in table 5).

TABLE 3

| conjugate | $CRM_{197}$ (mg) | BAANS (mg) | Amount of BAANS solution added (20 mg/ml) | Molar excess compared to $CRM_{197}$ |
| --- | --- | --- | --- | --- |
| $CRM_{197}$-preparation 57 cond. 1 | 8 | 1 | 50 ul | 30 |
| $CRM_{197}$-preparation 57 cond. 2 | 8 | 2 | 100 ul | 60 |
| $CRM_{197}$-preparation 57 cond. 3 | 8 | 3 | 150 ul | 90 |
| $CRM_{197}$-preparation 57 cond. 4 | 8 | 4.5 | 225 ul | 135 |
| $CRM_{197}$-preparation 57 cond. 5 | 8 | 6 | 300 ul | 180 |

TABLE 4

| conjugate | protein conc. (mg/ml) |
| --- | --- |
| $CRM_{197}$-preparation 57 cond.1 | 1.76 |
| $CRM_{197}$-preparation 57 cond.2 | 1.79 |
| $CRM_{197}$-preparation 57 cond.3 | 1.73 |
| $CRM_{197}$-preparation 57 cond.4 | 1.57 |
| $CRM_{197}$-preparation 57 cond.5 | 1.63 |

TABLE 5

| Sample | Rep | Total Load | Unconj | Conjugated | Mean load |
| --- | --- | --- | --- | --- | --- |
| $CRM_{197}$-preparation 57 cond. 1 | 1 | 6.1 | ND | 6.1 | 6.7 |
|  | 2 | 8.5 | ND | 8.5 |  |
|  | 3 | 5.5 | ND | 5.5 |  |
| $CRM_{197}$-preparation 57 cond. 2 | 1 | 7.8 | ND | 7.8 | 9.1 |
|  | 2 | 10.8 | ND | 10.8 |  |
|  | 3 | 8.7 | ND | 8.7 |  |
| $CRM_{197}$-preparation 57 cond. 3 | 1 | 9.1 | ND | 9.1 | 11.9 |
|  | 2 | 12.5 | ND | 12.5 |  |
|  | 3 | 14 | ND | 14 |  |
| $CRM_{197}$-preparation 57 cond. 4 | 1 | 12.5 | ND | 12.5 | 14.5 |
|  | 2 | 16.8 | ND | 16.8 |  |
|  | 3 | 14.2 | ND | 14.2 |  |
| $CRM_{197}$-preparation 57 cond. 5 | 1 | 12.2 | ND | 12.2 | 15.1 |
|  | 2 | 15.5 | ND | 15.5 |  |
|  | 3 | 17.6 | ND | 17.6 |  |

Example 11

BALB/c mice (Charles River, Montreal, QC.) (n=12 per group) were immunized with 10 μg of the conjugates of examples 1 to 4 by intra-muscular injection (on days 0, 28, 42) in the presence of aluminium hydroxide (alum; Alhydrogel-85: 40 μg $Al^{3+}$) and 50 μg CpG 24555. Anti-nicotine IgG antibody levels in plasma were measured by ELISA as described above.

Figure 1:
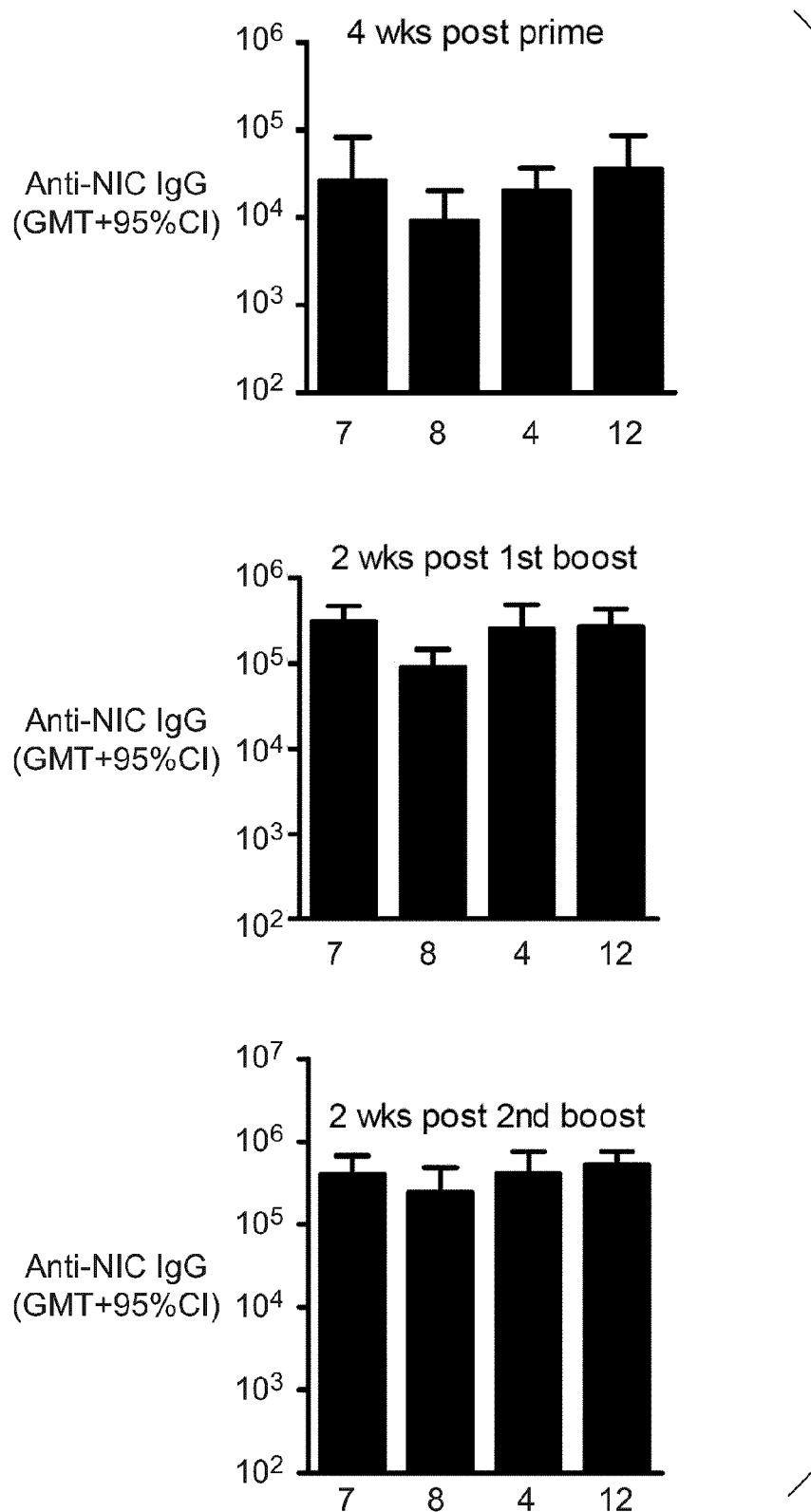
FIG. 1 shows the effect of immunization of mice with vaccines comprising nicotine-derived hapten-conjugates of the invention together with adjuvants, on anti-nicotine antibody levels in plasma at various time points. BALB/c mice (n=12 per group) were immunized with nicotine-derived haptens (from Preparations 4, 7, 8, and 12) conjugated to diphtheria toxoid (DT; 10 µg) by intra-muscular vaccination (on days 0, 28, 42) in the presence of aluminium hydroxide (alum; Alhydrogel-85: 40 µg $Al^{3+}$) and CpG 24555, a 21-mer TLR9 agonist containing immunostimulatory CpG motifs (50 µg). Anti-nicotine antibody levels (total IgG) in plasma were measured by ELISA.

The results are shown in FIG. 1, from which it can be seen that a strong anti-nicotine antibody response is obtained, for each tested conjugate, 4 weeks after the priming injection, which response is sustained or increased 2 weeks after each of the first and second boosting injections.

Example 12

BALB/c mice (n=12 per group) were immunized with 10 μg of the conjugates of examples 1 to 4 by intra-muscular injection (on days 0, 28, 42) in the presence of aluminium hydroxide (alum; Alhydrogel-85: 40 μg $Al^{3+}$) and 50 μg CpG 24555. Avidity indexes were calculated at various timepoints. The Avidity Index corresponds to the concentration of ammonium thiocyanate required to elute 50% of anti-nicotine antibodies from Nicotine-BSA coated plates as described above.

Figure 2:
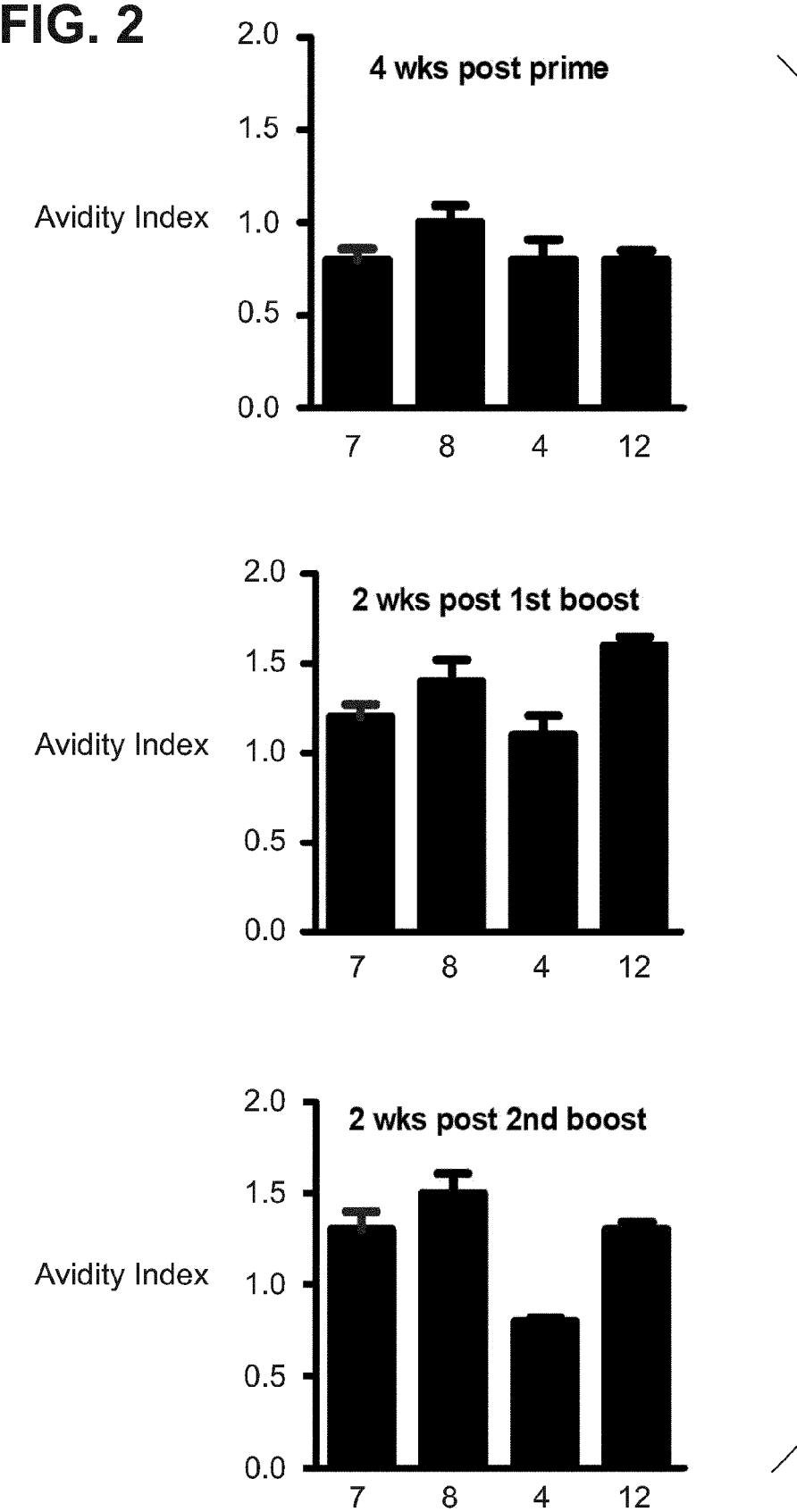
FIG. 2 shows the effect of immunization of mice with anti-nicotine vaccines containing conjugate antigens that comprise haptens of the invention on avidity of resulting anti-nicotine antibodies in plasma at various time points. BALB/c mice (n=12 per group) were immunized with nicotine-derived haptens (from Preparations 4, 7, 8 and 12) conjugated to diphtheria toxoid (DT; 10 µg) by intra-muscular vaccination (on days 0, 28, 42) in the presence of aluminium hydroxide (alum; Alhydrogel-85: 40 μg Al$^{3+}$) and CpG 24555 (50 μg). Avidity Index corresponds to concentration of ammonium thiocyanate required to elute 50% of anti-nicotine antibodies from nicotine-BSA coated plates and requirement of higher concentrations indicates with higher avidity antibodies.

The results are shown in FIG. 2, from which it can be seen that the antibodies in mice by the tested conjugates exhibit a high avidity 4 weeks after the priming injection, which is sustained or increased 2 weeks after each of the first and second boosting injections.

Example 13

BALB/c mice (n=6 per group) were immunized with 10 μg of the conjugates of examples 1 to 4 by intra-muscular injection (on days 0, 28, 42) in the presence of aluminium hydroxide (alum; Alhydrogel-85: 40 μg $Al^{3+}$) and 50 μg CpG 24555. At 2 weeks after the last boost, $^3$H-nicotine (0.05 mg/kg nicotine containing 3 µCi ³H-nic) was administered by intravenous injection, blood was collected, the animals were perfused, the brains were removed, and the levels of ³H quantified and the brain/plasma ratio of ³H determined as described above.

Figure 3:
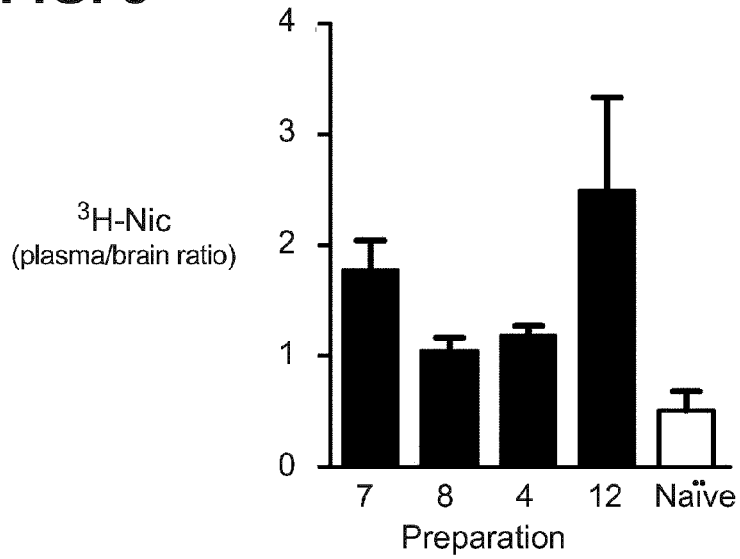
FIG. 3 shows the effect of immunization of mice with anti-nicotine vaccines containing conjugate antigens that comprise haptens of the invention on distribution of intravenously (IV) administered $^3$H-nicotine in brain and blood. BALB/c mice (n=6 per group) were immunized with nicotine-derived haptens (from Preparations 4, 7, 8 and 12) conjugated to diphtheria toxoid (DT; 10 μg) by intra-muscular vaccination (on days 0, 28, 42) in the presence of aluminium hydroxide (alum; Alhydrogel-85: 40 μg Al$^{3+}$) and CpG 24555 (50 μg). At 2 wks after the last boost, $^3$H-nicotine (0.05 mg/kg nicotine containing 3 μCi $^3$H-nic) was administered by IV injection, blood collected, animals perfused, brains removed, levels of $^3$H quantified and plasma/brain ratio of $^3$H determined.

The results are shown in FIG. 3, from which it can be seen that the plasma/brain ratio of the tested conjugates is significantly greater than that of control animals, indicating that the antibodies induced by the tested conjugates are specific for nicotine and have sequestered nicotine in the blood and prevented nicotine uptake into the brain.

Example 14

BALB/c mice (n=12 per group) were immunized with 10 µg of the conjugates of examples 1 to 4 by intra-muscular injection (on days 0, 28, 42) in the presence of aluminium hydroxide (alum; Alhydrogel-85: 40 µg $Al^{3+}$) and 50 µg CpG 24555. At 2 weeks after the second boost, interaction of anti-nicotine antibodies with nicotine was demonstrated by competition ELISA as described above.

Figure 4:
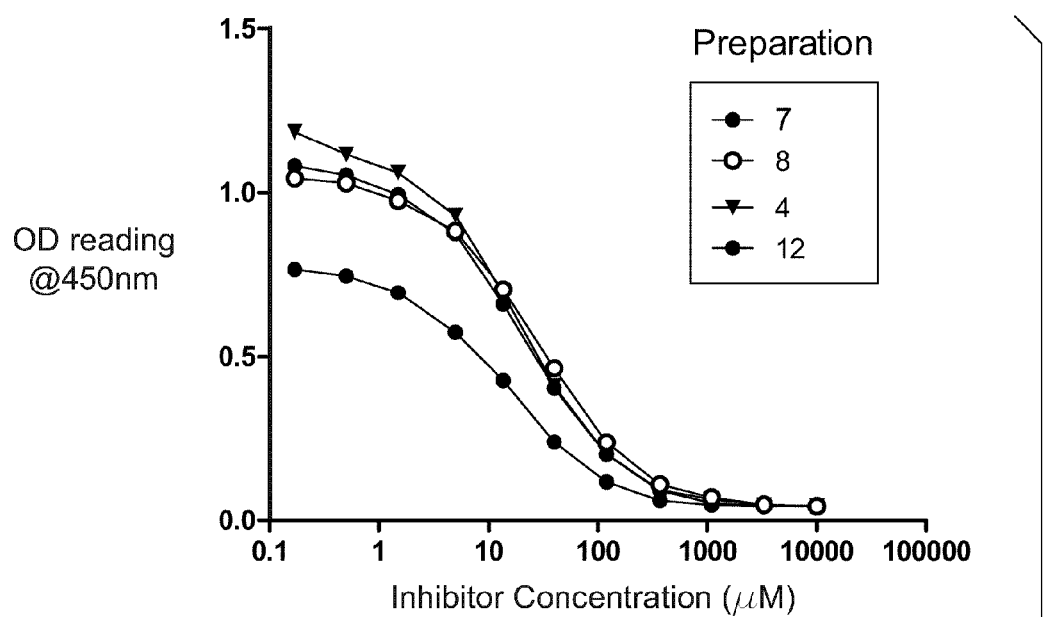
FIG. 4 shows the interaction with nicotine of anti-nicotine antibodies following immunization of mice with vaccines obtained from haptens of the invention. BALB/c mice (n=12 per group) were immunized with nicotine-derived haptens (from Preparations 4, 7, 8 and 12) conjugated to diphtheria toxoid (DT; 10 μg) by intra-muscular vaccination (on days 0, 28, 42) in the presence of aluminium hydroxide (alum; Alhydrogel-85: 40 μg Al$^{3+}$) and CpG 24555 (50 μg). At 2 wks after the last boost, the interaction of anti-nicotine antibodies with nicotine was demonstrated by competitive ELISA.

The results are shown in FIG. 4, from which it can be seen that the antibodies induced by the tested conjugates recognize and bind to nicotine.

Example 15

BALB/c mice (n=12 per group) were immunized with 10 µg of the conjugates of examples 1 and 2 by intra-muscular injection (on days 0, 28, 42) in the presence of aluminium hydroxide (alum; Alhydrogel-85: 40 µg $Al^{3+}$) and 50 µg CpG 24555. At 2 weeks after the second boost, the specificity of anti-nicotine antibodies to nicotine, cotinine, acetylcholine and varenicline was determined by competition ELISA as described above.

Figure 5:
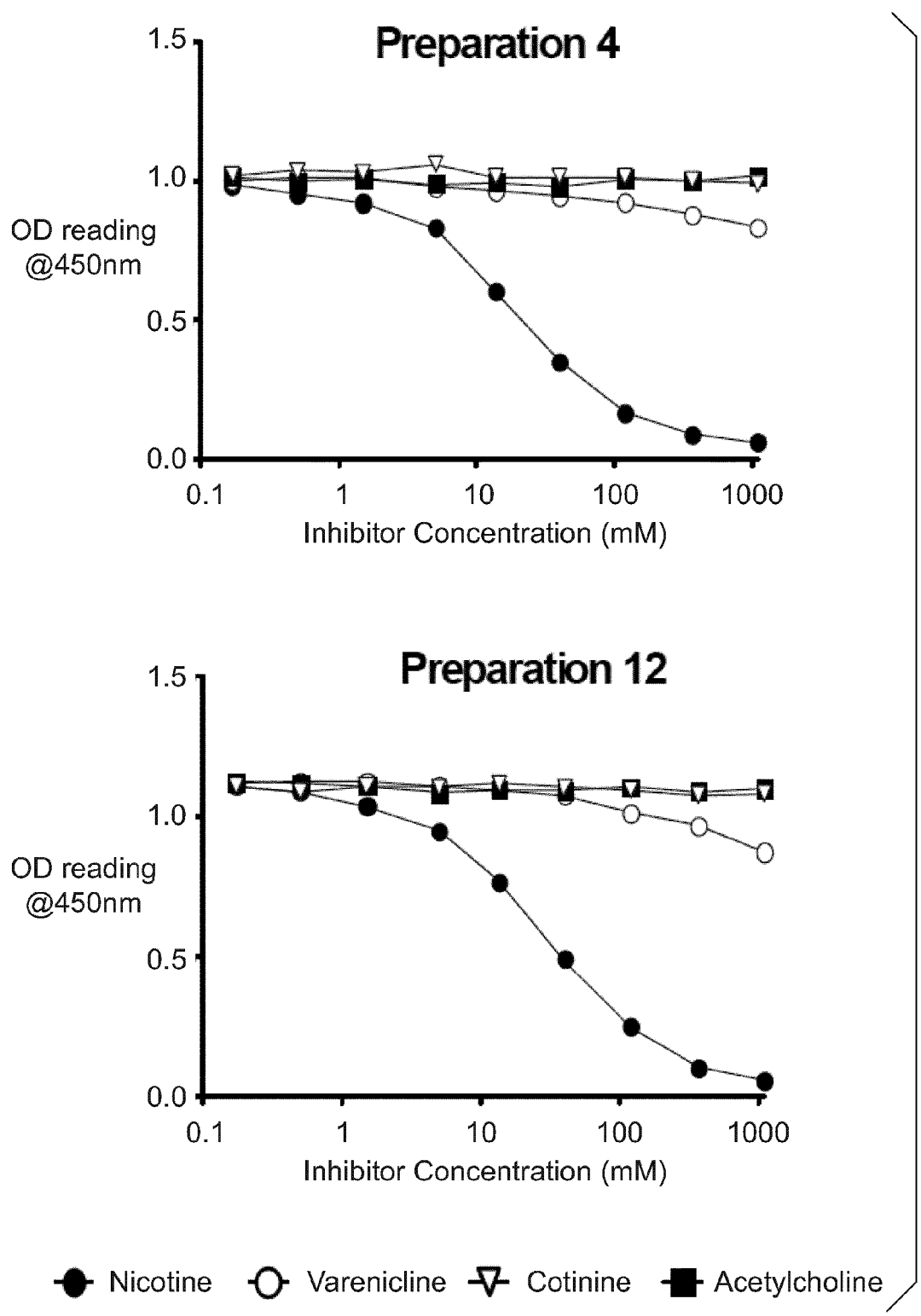
FIG. 5 shows the specificity of anti-nicotine antibodies following immunization of mice with vaccines containing haptens of the invention. BALB/c mice (n=12 per group) were immunized with nicotine-derived haptens (from Preparations 4 and 12) conjugated to diphtheria toxoid (DT; 10 μg) by intra-muscular vaccination (on days 0, 28, 42) in the presence of aluminium hydroxide (alum; Alhydrogel-85: 40 μg Al$^{3+}$) and CpG 24555 (50 μg). At 2 wks after the last boost, specificity of anti-nicotine antibodies to nicotine, cotinine, acetylcholine and varenicline was determined by competitive ELISA.
Figure 6:
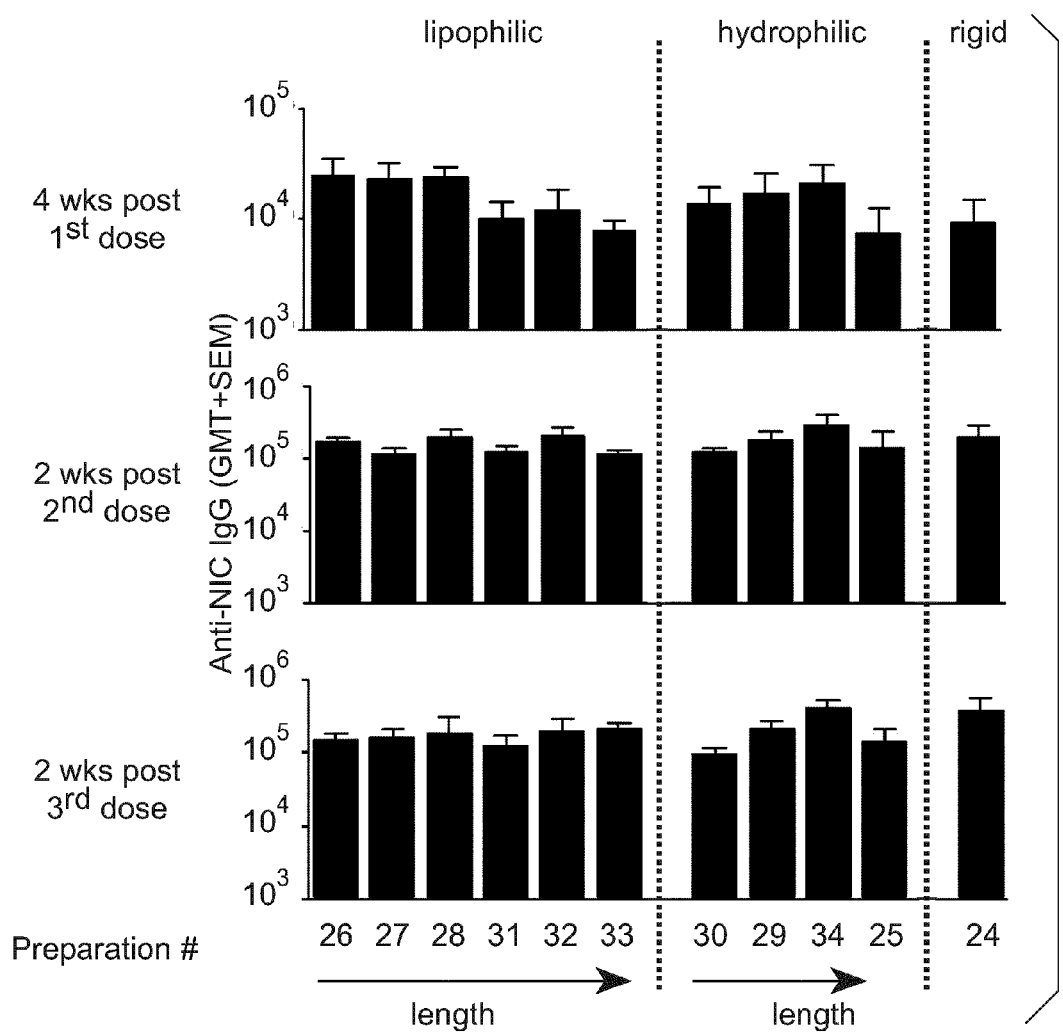
FIG. 6 shows the effect of immunization of mice with anti-nicotine vaccines using different spacers to conjugate the nicotine-derived hapten of the invention to the carrier on anti-nicotine antibody levels in plasma at various time points. BALB/c mice (n=12 per group) were immunized with nicotine-derived hapten (Preparation 4; 5'aminopropylnicotine) conjugated to diphtheria toxoid (DT; 10 μg) with conjugates being using different linkers (Preparations 24-34) by intra-muscular vaccination (on days 0, 28, 42) in the presence of aluminium hydroxide (alum; Alhydrogel-85: 40 μg Al$^{3+}$) and 50 μg CpG 24555. Anti-nicotine IgG Ab levels in plasma were measured by ELISA.
Figure 7:
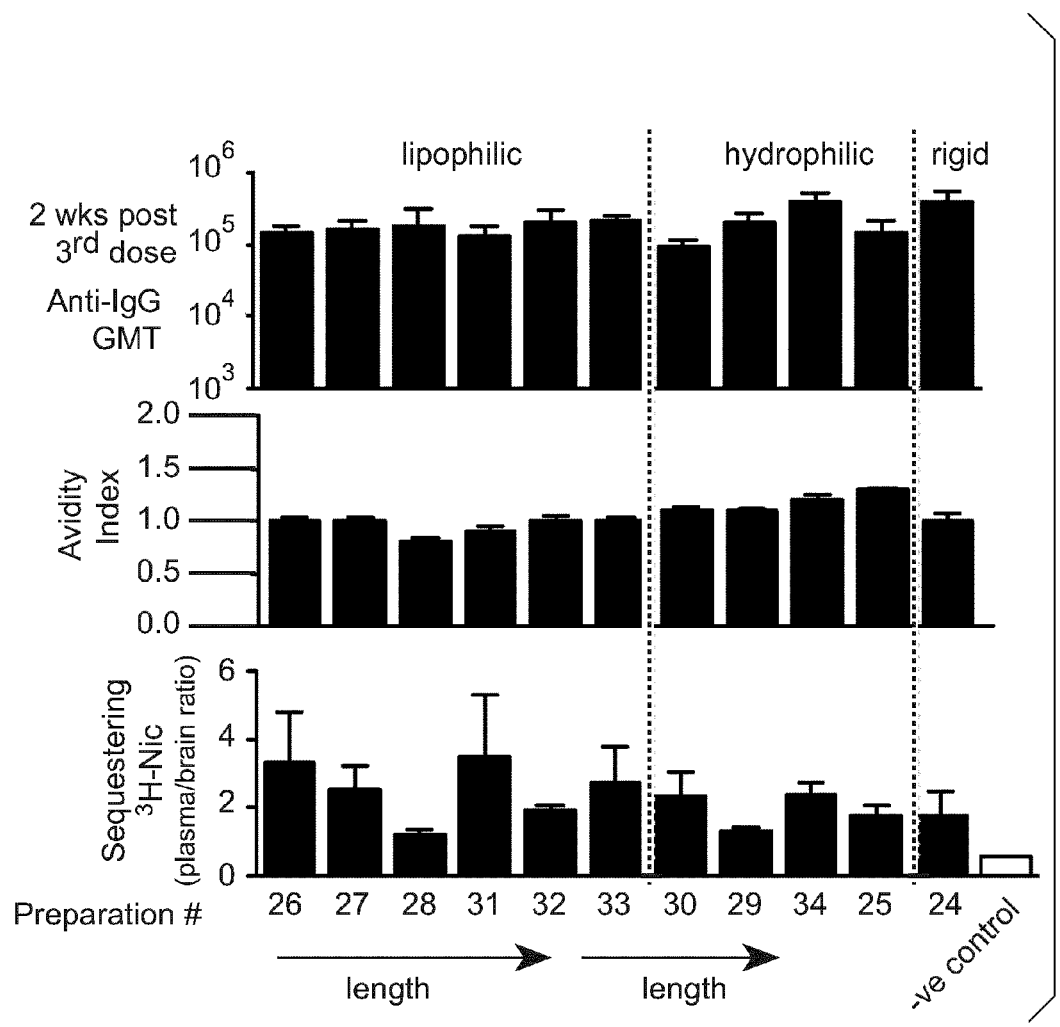
FIG. 7 shows the effect of immunization of mice with anti-nicotine vaccines using different spacers to conjugate the nicotine-derived hapten of the invention to the carrier on levels and avidity of anti-nicotine antibodies in plasma and on the distribution of $^3$H-nicotine in plasma and brain. BALB/c mice (n=12 per group) were immunized with nicotine-derived hapten (Preparation 4; 5'aminopropylnicotine) conjugated to diphtheria toxoid (DT; 10 μg) with conjugates being using different linkers (Preparations 24-34) by intra-muscular vaccination (on days 0, 28, 42) in the presence of aluminium hydroxide (alum; Alhydrogel-85: 40 μg Al$^{3+}$) and CpG 24555 (50 μg). At 2 wks post $3^{rd}$ immunization, anti-nicotine IgG Ab levels in plasma were measured by ELISA and avidity was measured by ammonium thiocyanate assay. $^3$H-nicotine (0.05 mg/kg nicotine containing 3 μCi $^3$H-nic) was administered by IV injection, blood collected, animals perfused, brains removed, levels of $^3$H quantified and plasma/brain ratio of $^3$H determined.
Figure 8:
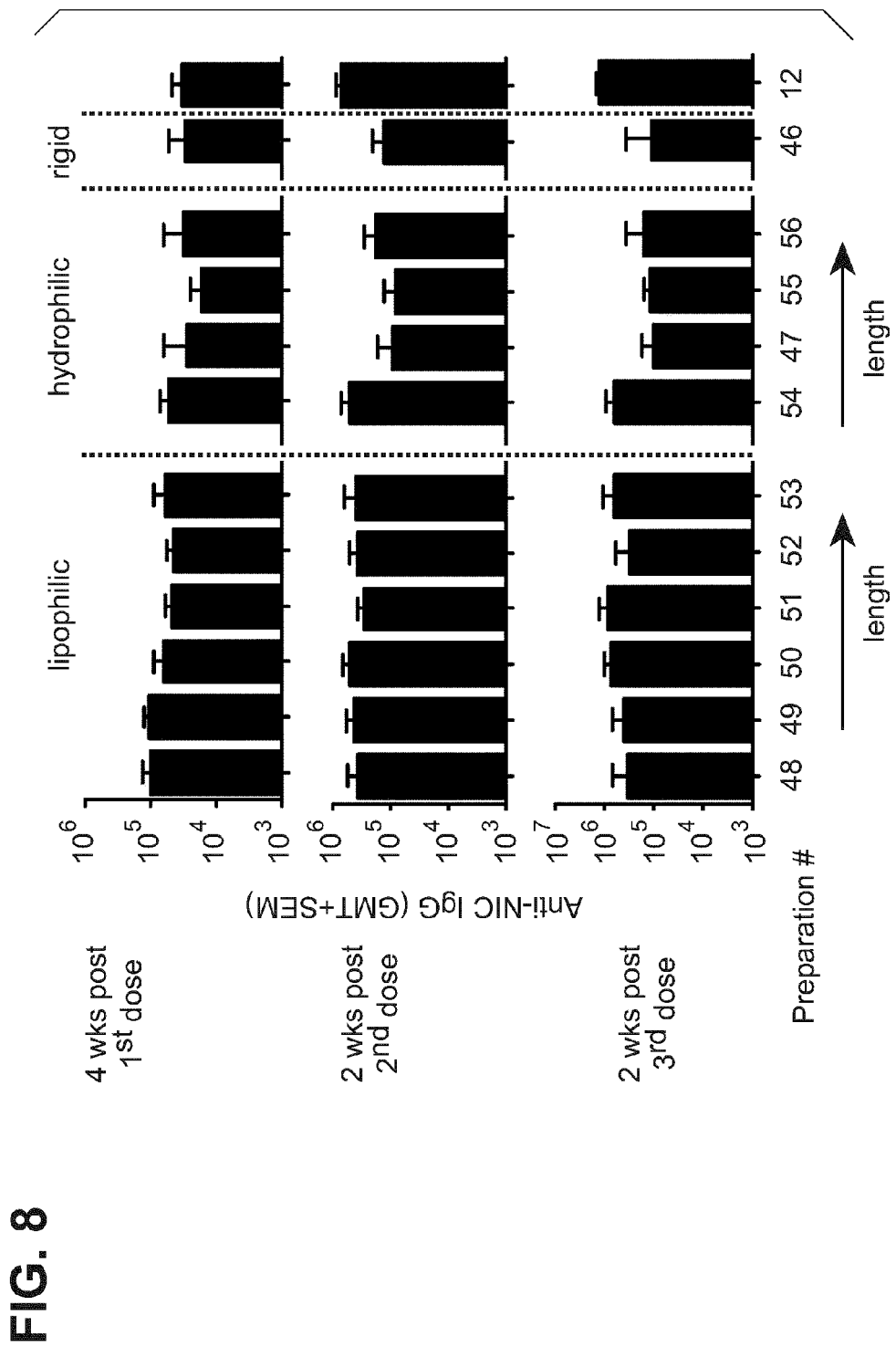
FIG. 8 shows the effect of immunization of mice with anti-nicotine vaccines using different spacers to conjugate the nicotine-derived hapten of the invention to the carrier on anti-nicotine antibody levels in plasma at various time points. BALB/c mice (n=12 per group) were immunized with nicotine-derived hapten (Preparation 12; 5'aminoethoxy nicotine) conjugated to diphtheria toxoid (DT; 10 μg) with conjugates being using different linkers (Preparations 24-34) by intramuscular vaccination (on days 0, 28, 42) in the presence of aluminium hydroxide (alum; Alhydrogel-85: 40 μg Al$^{3+}$) and CpG 24555 (50 μg). Anti-nicotine antibody levels (total IgG) in plasma were measured by ELISA
Figure 9:
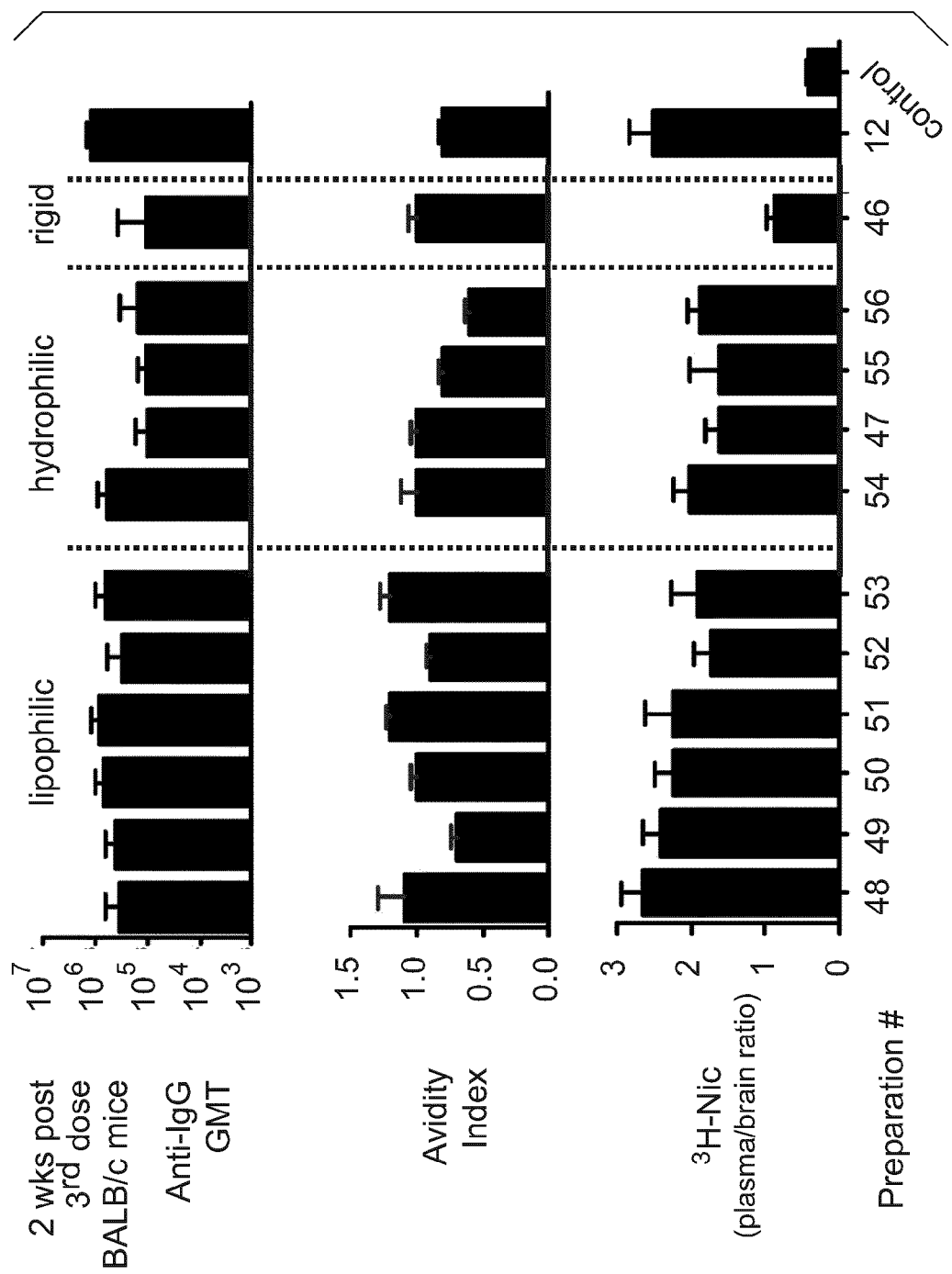
FIG. 9 shows the effect of immunization of mice with anti-nicotine vaccines using different spacers to conjugate the nicotine-derived hapten of the invention to the carrier on levels and avidity of anti-nicotine antibodies in plasma and on the distribution of $^3$H-nicotine in plasma and brain. BALB/c mice (n=12 per group) were immunized with nicotine-derived hapten (Preparation 12; 5'aminoethoxy nicotine) conjugated to diphtheria toxoid (DT; 10 μg) with conjugates being using different linkers (Preparations 24-34) by intramuscular vaccination (on days 0, 28, 42) in the presence of aluminium hydroxide (alum; Alhydrogel-85: 40 μg Al$^{3+}$) and CpG 24555 (50 μg). At 2 wks post $3^{rd}$ immunization, anti-nicotine IgG Ab levels in plasma were measured by ELISA and avidity was measured by ammonium thiocyanate assay. $^3$H-nicotine (0.05 mg/kg nicotine containing 3 μCi $^3$H-nic) was administered by IV injection, blood collected, animals perfused, brains removed, levels of $^3$H quantified and plasma/brain ratio of $^3$H determined.
Figure 10:
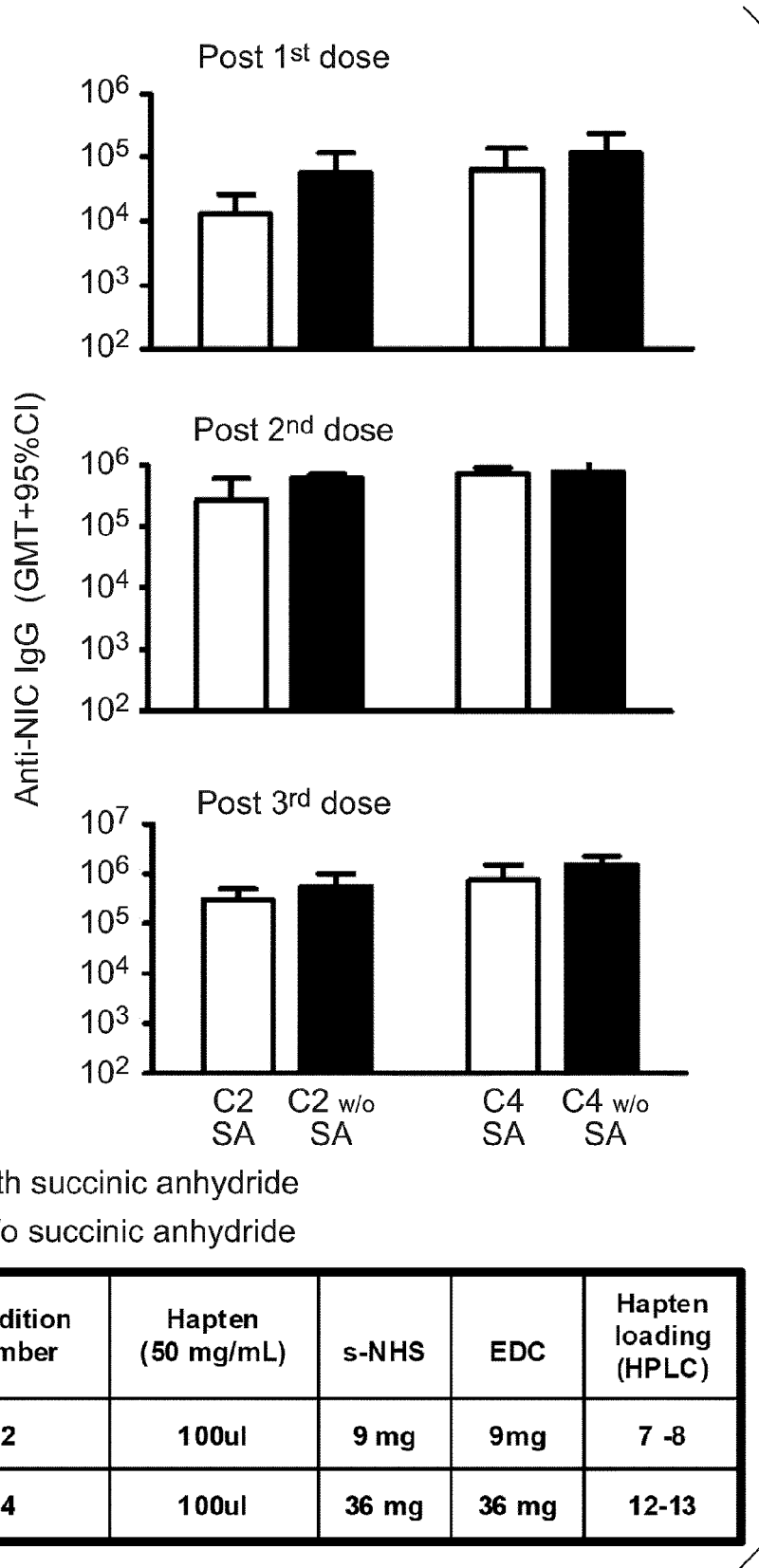
FIG. 10 shows the effect of succinylation of the hapten-carrier conjugates of the invention on anti-nicotine antibody levels in plasma at various time points. BALB/c mice (n=12 per group) were immunized with nicotine-derived hapten (Preparation 4; 5'aminopropylnicotine) conjugated to diphtheria toxoid (DT; 10 μg) with conjugates being prepared using 2 different conditions, each with or without a succinic anhydride step, by intra-muscular vaccination (on days 0, 28, 42) in the presence of aluminium hydroxide (alum; Alhydrogel-85: 40 μg Al$^{3+}$) and CpG 24555 (50 μg). Anti-nicotine antibody levels (total IgG) in plasma were measured by ELISA.
Figure 11:
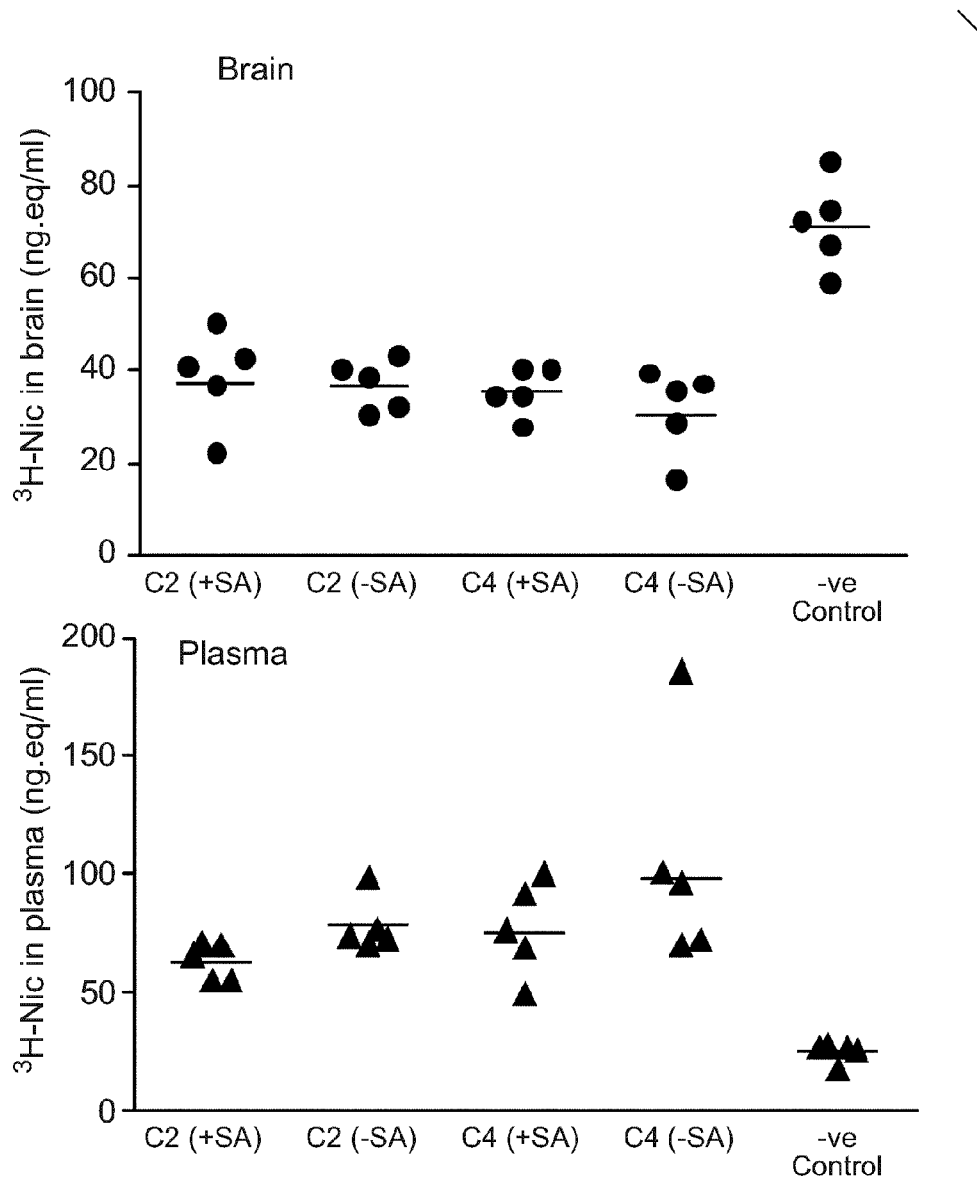
FIG. 11 shows the effect of succinylation of the hapten-carrier conjugates of the invention, on distribution of $^3$H-nicotine in blood and brain. BALB/c mice (n=12 per group) were immunized with nicotine-derived hapten (Preparation 4; 5'aminopropylnicotine) conjugated to diphtheria toxoid (DT; 10 μg) with conjugates being prepared using 2 different conditions, each with or without a succinic anhydride step, by intra-muscular vaccination (on days 0, 28, 42) in the presence of aluminium hydroxide (alum; Alhydrogel-85: 40 μg Al$^{3+}$) and CpG 24555 (50 μg). At 2 wks after last boost, $^3$H-nicotine (0.05 mg/kg nicotine containing 3 μCi $^3$H-nic) was administered by IV injection, blood collected, animals perfused, brains removed, levels of $^3$H quantified in brain and plasma.

The results are shown in FIG. 5, from which it can be seen that there is a dose-dependent inhibition of binding of anti-nicotine antibodies to nicotine-coated ELISA plates as amount of added nicotine is increased. However, no such effect is observed with varenicline, cotinine or acetylcholine, indicating that the antibodies induced by the tested conjugates are specific for nicotine and not for cotinine, varenicline or acetylcholine.

Example 16

BALB/c mice (n=12 per group) were immunized with 10 µg of the conjugates of example 5 by intra-muscular injection (on days 0, 28, 42) in the presence of aluminium hydroxide (alum; Alhydrogel-85: 40 µg $Al^{3+}$) and 50 µg CpG 24555. Anti-nicotine antibody levels (total IgG) in plasma were measured by ELISA as described above.

The results are shown in FIGS. 6, 7, 8 and 9 from which it can be seen that an very strong anti-nicotine antibody response is obtained, for each tested conjugate, 4 weeks after the priming injection, which response is increased 2 weeks after boost. Furthermore, both levels of anti-nicotine antibodies as well as avidity of anti-nicotine antibodies vary depending on spacer used. In addition, all tested conjugates result in higher plasma/brain ratios than in control animals, indicating that antibodies induced by tested conjugates can sequester nicotine in the blood and prevent it's uptake into brain to a greater extent than in control animals.

Example 17

BALB/c mice (n=12 per group) were immunized with 10 µg of the conjugates of Example 6 and 7 by intra-muscular injection (on days 0, 28, 42) in the presence of aluminium hydroxide (alum; Alhydrogel-85: 40 µg $Al^{3+}$) and 50 µg CpG 24555. Anti-nicotine antibody levels (total IgG) in plasma were measured by ELISA. At 2 weeks after the last boost, ³H-nicotine (0.05 mg/kg nicotine containing 3 µCi ³H-nic) was administered by intravenous injection, blood was collected, the animals were perfused, the brains were removed, and the levels of ³H quantified and the % change in levels of ³H relative to control animals was determined as described above.

Figure 12:
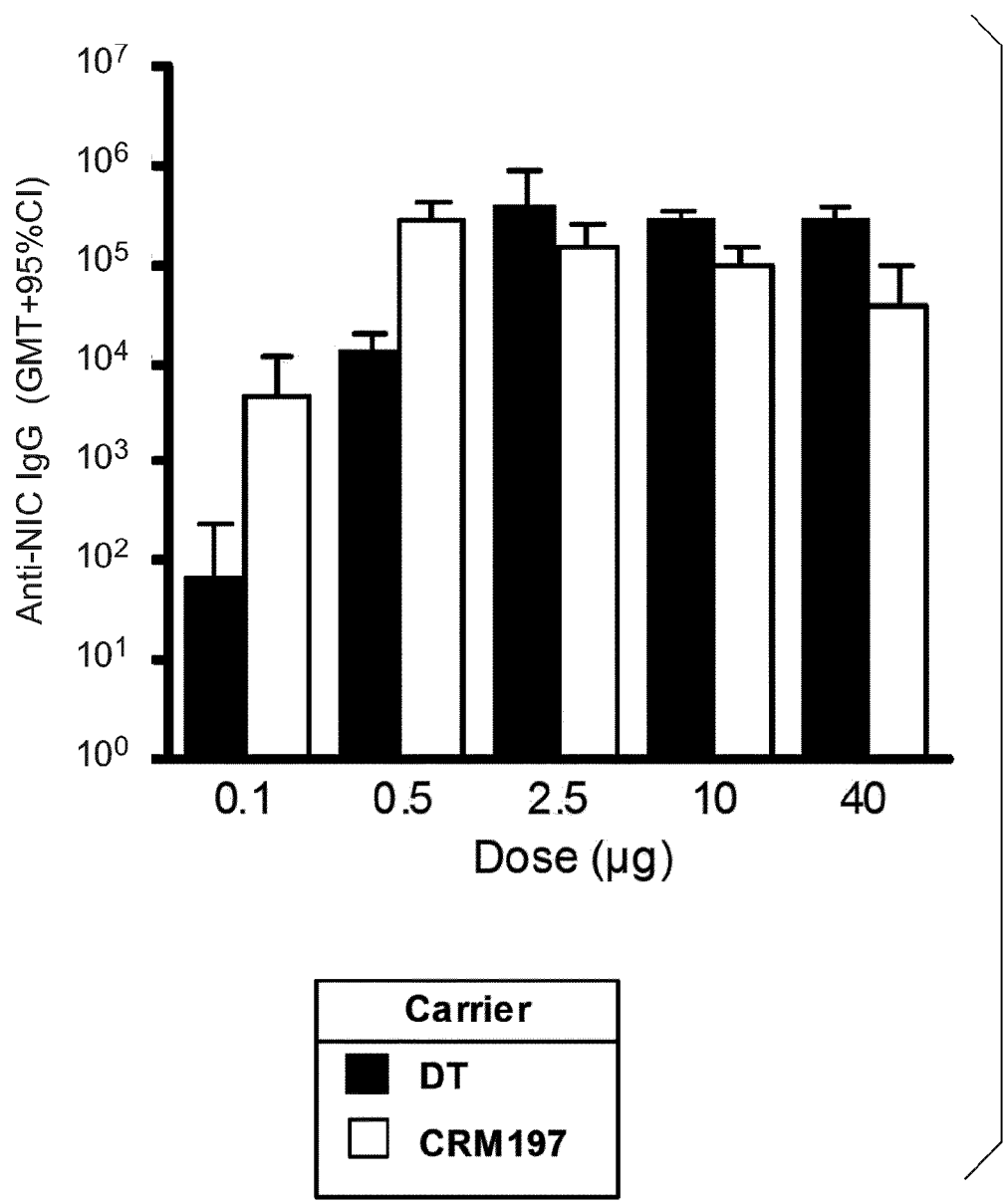
FIG. 12 shows the effect of immunization of mice with anti-nicotine vaccines using different spacers to conjugate the nicotine-derived hapten of the invention to the carrier on the anti-nicotine antibody levels in plasma at various time points. BALB/c mice (n=12 per group) were immunized with nicotine-derived hapten (Preparation 12; 5'aminoethoxy nicotine) conjugated to diphtheria toxoid (DT; 10 μg) or CRM$_{197}$ (10

The results are shown in FIGS. 12 (anti-nicotine antibody levels) and 13 (% change in levels of ³H) from which it can be seen that an immune response is obtained, for each tested conjugate, which response increased in a dose dependent manner. This indicates that both DT and $CRM_{197}$ are suitable carriers for the nicotine-derived haptens. In addition, all tested conjugates result in lower levels of ³H-nicotine entering the brain than in control animals, indicating that antibodies induced by tested conjugates can sequester nicotine in the blood and prevent it's uptake into brain to a greater extent than in control animals.

Example 18

BALB/c mice (n=12 per group) were immunized with 10 µg of the conjugates of Example 6, 7 and 8 by intra-muscular injection (on days 0, 28, 42) in the presence of aluminium hydroxide (alum; Alhydrogel-85: 40 µg $Al^{3+}$) and 50 µg CpG 24555. Anti-nicotine IgG Ab levels in plasma were measured by ELISA. At 2 weeks after the last boost, ³H-nicotine (0.05 mg/kg nicotine containing 3 µCi ³H-nic) was administered by iv injection, blood was collected, the animals were perfused, the brains were removed, and the levels of ³H quantified and the % change in levels of ³H relative to control animals was determined as described above.

The results are shown in FIGS. 14 (anti-nicotine antibody levels) and 15 (% change in levels of ³H) from which it can be seen that an immune response is obtained, for each tested conjugate, which response increased with hapten loading. In addition, all tested conjugates result in lower levels of ³H-nicotine entering the brain than in control animals, indicating that antibodies induced by tested conjugates can sequester nicotine in the blood and prevent it's uptake into brain to a greater extent than in control animals.

Example 19

BALB/c mice (n=10 per group) were immunized with 10 µg of the conjugate of Example 7 by intra-muscular injection in the presence of aluminium hydroxide (alum; Alhydrogel-85: 40 µg $Al^{3+}$) and 10 µg CpG 24555, or in the presence of ISCOMATRIX (IMX; 0.1 to 3.0 Units). Anti-nicotine IgG Ab levels in plasma were measured by ELISA (day 21 and 28), and avidity by inhibition ELISA. The results are shown in FIGS. 16 and 17 from which it can be seen that an immune response (Ab levels and avidity) is obtained with the use of CpG 24555 and aluminium hydroxide as combination adjuvant, or with ISCOMATRIX as sole adjuvant, which response increased with ISCOMATRIX dose.

At 1 wk post 2nd immunization, ³H-nicotine (0.05 mg/kg nicotine containing 3 µCi ³H-nic) was administered by IV injection, blood collected, animals perfused, brains removed, levels of ³H quantified and % change in 3H-nicotine in blood and brains relative to control animals was determined. Results are shown in FIG. 18 from which it can be seen that the use of CpG 24555 and aluminum hydroxide as combination adjuvants or ISCOMATRIX as sole adjuvant result in lower levels of $^3$H-nicotine entering the brain than in control animals, indicating that antibodies induced by tested conjugates can sequester nicotine in the blood and prevent it's uptake into brain to a greater extent than in unimmunized control animals.

Example 20

The samples described in Table 6 below were prepared as follows.

a) Frozen $CRM_{197}$ (200 ml at 5.9 mg/ml) was thawed overnight at 4° C.

b) Once thawed, the $CRM_{197}$ was concentrated from 200 ml to 100 ml by ultrafiltration (UF) using a Kvick Start polyethersulfone (PES) membrane with a 10 kD molecular weight cutoff.

c) The concentrated $CRM_{197}$ was diafiltered (DF) 8 TOVs (turn over volumes) using 50 mM MOPS (3-(N-morpholino) propanesulfonic acid), 50 mM NaCl, pH 7.2. The post UF/DF $CRM_{197}$ was filtered using a SARTOPORE 2 150 sterile capsule filter.

d) The concentration of the $CRM_{197}$ was determined by measuring absorbance at $A_{280}$ using an extinction coefficient of 0.942. The concentration was determined to be 9.65 mg/ml.

f) The post UF/DF $CRM_{197}$ was diluted to 7.18 mg/ml from 9.65 mg/ml using 50 mM MOPS, 50 mM NaCl, pH 7.2.

g) In a separate vessel, 6 M HCl solution (7.46 mL) was slowly added to 7460 mg of the hapten of preparation 12 while cooled in an ice bath. Then 50 mM MOPS, 50 mM NaCl, pH 7.2 buffer was added (2.00 mL) and the pH was checked by pH paper. The pH was approximately 9. 6 M HCl was added in small increments until a pH of 7.5 was achieved (1.70 mL HCl added). The total volume of the solution was 18.65 mL resulting in a concentration of 400 mg/mL of the hapten of preparation 12.

h) In a separate vessel, 7000 mg of sulfo-N-hydroxysuccinimide (sNHS) was dissolved in 50 mM MOPS, 50 mM NaCl, pH 7.2 solution (14 mL) and 19.25 M NaOH solution was added in small increments until a pH of 7.13 was achieved (1.44 mL of NaOH added). The total volume of the solution was 18.50 mL resulting in a concentration of 378 mg/mL of sNHS.

i) In a separate vessel, 8000 mg of 1-ethyl-3-(3-dimethylaminopropyl) carbodiimide hydrochloride (EDC) was dissolved in 5 mL of 50 mM MOPS, 50 mM NaCl, pH 7.2. The total volume of the solution was 12.0 mL resulting in a concentration of 666 mg/mL of EDC. EDC solution was made last, just prior to addition to the conjugation reactions.

j) The post UF/DF $CRM_{197}$, the hapten of preparation 12, sNHS, and EDC solutions were combined in such a way as to generate the 24 samples listed in Table 6. For the 24 samples, the correctly calculated amounts of the solutions were mixed together in the following manner: UF/DF $CRM_{197}$, the hapten of preparation 12, and sNHS were combined and the pH of the mixture was checked. For samples number 10 and 18, the pH was further adjusted using 1 N NaOH to bring the pH to approximately 7.5. Lastly, EDC was added to the samples. Each reaction tube was briefly vortexed and incubated at 15° C. in a water bath for 18 hrs.

k) After 18 hours of incubation, samples were buffer exchanged using Amicon ultra centrifugal concentrators with a 30 kD molecular weight cutoff. The buffer used was 20 mM potassium phosphate, 20 mM histidine, pH 7.0. Protein concentration was determined using a commercially available micro BCA kit.

l) 200 mg/ml sucrose was dissolved in water and added to the each of the 24 conjugated samples at a 1:1 (volume) ratio. Subsequently, PS80 was added to a final concentration of 0.2 mg/ml. The samples were stored at 4° C. for short term storage, −20° C. for long term storage.

TABLE 6

| Sample | sNHS: $CRM_{197}$ molar ratio | Hapten of Prep 12: $CRM_{197}$ molar ratio | EDC: $CRM_{197}$ molar ratio | $CRM_{197}$ (mg/mL) | $IC_{50}$ | Efficacy |
|---|---|---|---|---|---|---|
| 1 | 2600 | 2550 | 3000 | 3.0 | 7.95 | 41.0 |
| 2 | 5000 | 2550 | 3000 | 3.0 | 4.85 | 46.0 |
| 3 | 3800 | 4672 | 3000 | 3.0 | 9.05 | 50.0 |
| 4 | 3800 | 3258 | 4634 | 3.0 | 10.1 | 33.0 |
| 5 | 3800 | 3258 | 3408 | 4.6 | 8.05 | 38.0 |
| 6 | 200 | 2550 | 3000 | 3.0 | 5.65 | 43.0 |
| 7 | 1400 | 428 | 3000 | 3.0 | 18.25 | 26.0 |
| 8 | 1400 | 1842 | 1366 | 3.0 | 5.3 | 48.0 |
| 9 | 1400 | 1842 | 2592 | 1.4 | 4.75 | 45.0 |
| 10 | 3800 | 428 | 3000 | 3.0 | 20.4 | 21.0 |
| 11 | 3800 | 1842 | 1366 | 3.0 | 5.6 | 32.0 |
| 12 | 3800 | 1842 | 2592 | 1.4 | 4.65 | 33.0 |
| 13 | 1400 | 4672 | 3000 | 3.0 | 8.43 | 32.0 |
| 14 | 2600 | 3964 | 1366 | 3.0 | 3.87 | 26.0 |
| 15 | 2600 | 3964 | 2592 | 1.4 | 6.84 | 41.0 |
| 16 | 1400 | 3258 | 4634 | 3.0 | 7.97 | 32.0 |
| 17 | 2600 | 1136 | 4634 | 3.0 | 15.81 | 27.0 |
| 18 | 2600 | 2550 | 4226 | 1.4 | 12.16 | 36.0 |
| 19 | 1400 | 3258 | 3408 | 4.6 | 19.82 | 20.0 |
| 20 | 2600 | 1136 | 3408 | 4.6 | 18.37 | 33.0 |
| 21 | 2600 | 2550 | 1774 | 4.6 | 10.12 | 42.0 |
| 22 | 2600 | 2550 | 3000 | 3.0 | 8.51 | 40.0 |
| 23 | 2600 | 2550 | 3000 | 3.0 | 8.3 | 46.0 |
| 24 | 2600 | 2550 | 3000 | 3.0 | 16.71 | 44.0 |

The analytical methodology utilized to examine the samples 1-24 are detailed below.

SELDI-MS.

Surface-enhanced laser desorption ionization (SELDI) is an ionization method in mass spectrometry that is used for the analysis of protein mixtures. The assay reports net mass gain to the $CRM_{197}$ scaffold through the conjugation process. The change in mass is reported as adducts to the scaffold. Ideally, the adducts should equate with the Hapten specific Epitope Density assay. Adducts=($Mass_{Conjugate}$−$Mass_{Scaffold}$)/$Mass_{Hapten}$. It is noted that adducts levels in excess of the ED value indicates that mass other than hapten is added to the scaffold; and that samples high in adduct are also high in HMMS.

Size Exclusion Chromatography.

A size exclusion assay was developed to resolve HMMS (high molecular mass species), Dimer, Monomer and LMMS (low molecular mass species) towards understanding process parameters that impact relative abundance of these components. The method reports relative area percents for the HMMS peak group, Dimer, Monomer and the LMMS peak group. It is noted that process stoichiometry and ratio's of the starting materials impacted the apparent distribution of peak area between HMMS, Dimer, Monomer and LMMS.

Epitope Density.

A reversed phase liquid chromatography assay coupled to an acid hydrolysis sample preparation was developed to determine the amount of hapten conjugated to the $CRM_{197}$ carrier protein. The hapten molecule is conjugated via an amide bond to the $CRM_{197}$ scaffold; this bond is hydrolyzed to release hapten along with the substituent amino acids according to standard hydrolysis chemistry. The amount of conjugated hapten 7 is a measure of process consistency, product quality and efficacy.

The results of the characterization of samples 1-24 are shown in Table 7. This data shows a strong relationship between Efficacy and Hapten epitope density coupled to $CRM_{197}$. In addition, it shows that optimal epitope density values correlate with high monomer, low HMMS and low adducts.

TABLE 7

| Sample | Acid Hydrolysis Epitope Density | SELDI-MS Apparent Epitope Density | High Molecular Mass Species (HMMS) % | Dimer % | Monomer % | Low Molecular Mass Species (LMMS) % |
|---|---|---|---|---|---|---|
| 1 | 18.6 | 19.9 | 0.0 | 0.0 | 100.0 | 0.0 |
| 2 | 13.0 | 15.8 | 0.0 | 0.0 | 100.0 | 0.0 |
| 3 | 14.3 | 12.2 | 0.0 | 0.0 | 94.1 | 5.9 |
| 4 | 27.1 | 30.4 | 1.9 | 0.0 | 95.1 | 3.0 |
| 5 | 20.8 | 24.8 | 1.3 | 0.0 | 98.7 | 0.0 |
| 6 | 15.2 | 17.4 | 0.0 | 0.0 | 100.0 | 0.0 |
| 7 | 13.1 | 34.3 | 20.0 | 20.4 | 49.8 | 9.7 |
| 8 | 11.5 | 12.8 | 0.0 | 0.0 | 100.0 | 0.0 |
| 9 | 4.8 | 12.7 | 0.0 | 0.0 | 100.0 | 0.0 |
| 10 | 5.4 | 30.5 | 10.2 | 9.2 | 72.1 | 8.5 |
| 11 | 6.7 | 6.8 | 1.6 | 6.3 | 84.8 | 7.3 |
| 12 | 9.0 | 12.9 | 0.0 | 0.0 | 100.0 | 0.0 |
| 13 | 17.4 | 23.9 | 5.0 | 11.8 | 83.2 | 0.0 |
| 14 | 4.5 | 4.8 | 4.6 | 4.5 | 79.5 | 11.3 |
| 15 | 7.9 | 10.3 | 0.3 | 0.0 | 99.7 | 0.0 |
| 16 | 25.0 | 31.7 | 0.0 | 0.0 | 100.0 | 0.0 |
| 17 | 15.6 | 41.6 | 7.7 | 10.2 | 82.1 | 0.0 |
| 18 | 7.0 | 21.9 | 0.0 | 0.0 | 100.0 | 0.0 |
| 19 | 30.0 | 36.3 | 0.0 | 0.0 | 100.0 | 0.0 |
| 20 | 17.5 | 42.2 | 5.0 | 0.0 | 86.3 | 8.7 |
| 21 | 10.5 | 12.1 | 0.0 | 0.0 | 99.3 | 0.7 |
| 22 | 13.2 | 16.7 | 14.4 | 0.0 | 57.0 | 28.6 |
| 23 | 18.1 | 25.0 | 0.0 | 0.0 | 100.0 | 0.0 |
| 24 | 16.1 | 23.6 | 0.0 | 0.0 | 100.0 | 0.0 | levels of $^3H$ quantified and % change in $^3H$-nicotine in blood and brains relative to control animals was determined. Results are shown in FIGS. 21 and 22 from which it can be seen that all tested conjugates result in lower levels of $^3H$-nicotine entering the brain than in non-immunized control animals, indicating that antibodies induced by tested conjugates can sequester nicotine in the blood and prevent it's uptake into brain to a greater extent than in control animals, and that efficacy increased with % monomer (FIG. 21) and was optimal with a hapten load of between 10 to 18 haptens per unit carrier (FIG. 22).

Example 22

Samples 1-24 (see Example 20, Tables 6 and 7) were tested for binding to Alhydrogel. BALB/c mice (n=10 per group) were also immunized with 10 µg of these different conjugates by intra-muscular injection in the presence of aluminium hydroxide (alum; Alhydrogel-85: 40 µg $Al^{3+}$) and 10 µg CpG 24555. At 1 wk post 2nd immunization, $^3H$-nicotine (0.05 mg/kg nicotine containing 3 µCi $^3H$-nic) was administered by IV injection, blood collected, animals perfused, brains removed, levels of $^3H$ quantified and % change in $^3H$-nicotine in blood and brains relative to control animals was determined. Results are shown in FIG. 23, from which it can be seen that conjugates with a higher % monomer content, have a higher % binding to Alhydrogel and that this correlates with a greater efficacy as demonstrated by a greater reduction in the amount of $^3H$-nicotine in the brain.

SEQUENCE LISTING

```
<160> NUMBER OF SEQ ID NOS: 1

<210> SEQ ID NO 1
<211> LENGTH: 21
<212> TYPE: DNA
<213> ORGANISM: Artificial sequence
<220> FEATURE:
<223> OTHER INFORMATION: Synthetic oligonucleotide

<400> SEQUENCE: 1
tcgtcgtttt tcggtgcttt t                                            21
```

Example 21

BALB/c mice (n=10 per group) were immunized with 10 µg of samples 1-24 (see Example 20, Tables 6 and 7) by intra-muscular injection in the presence of aluminium hydroxide (alum; Alhydrogel-85: 40 µg $Al^{3+}$) and 10 µg CpG 24555. Anti-nicotine IgG Ab levels in plasma were measured by ELISA (day 21 and 28), and avidity by inhibition ELISA. The results are shown in FIGS. 19 and 20 from which it can be seen that an immune response is obtained, for each tested conjugate, which response increased with % monomer and which was optimal with a hapten load of between 10 to 18 haptens per unit carrier.

At 1 wk post 2nd immunization, $^3H$-nicotine (0.05 mg/kg nicotine containing 3 µCi $^3H$-nic) was administered by IV injection, blood collected, animals perfused, brains removed,

The invention claimed is:

1. A hapten-carrier conjugate of formula (III):

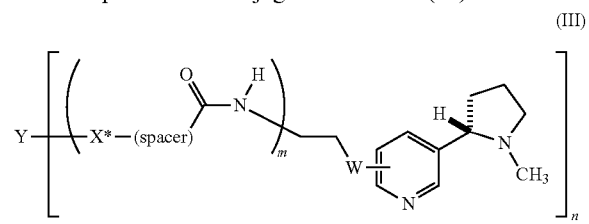

wherein:

W is —O—, and W is in position 5 of the pyridine ring;

-(spacer)- is a $C_1$-$C_8$ alkylene group, a $C_3$-$C_{10}$ cycloalkylene group or a $C_1$-$C_{12}$ alkylene group interrupted by 1 to 4 oxygen atoms and optionally interrupted by a —N(H)C(O)—;

X* is —NH— or —S—;

m is 1;

n is an integer from 1 to 1000; and

Y is an optionally modified carrier protein selected from bacterial toxoids, immunogenic substances, viruses, virus-like particles, protein complexes, proteins, polypeptides, liposomes and immuno-stimulating complexes.

2. The hapten-carrier conjugate according to claim 1, wherein the carrier protein is an optionally modified protein selected from derivatives of tetanus toxin, derivatives of diphtheria toxin, keyhole limpet hemocyanin (KLH), hemocyanine, outer membrane protein complex (OMPC) from *Neisseria meningitidis*, the B subunit of heat-labile *Escherichia coli*, recombinant exoprotein A from *Pseudomonas aeruginosa* (rEPA) and other virus-like particles such as those assembled from recombinant coat protein of bacteriophage Qb, hepatitis B surface antigen, hepatitis B core antigen or a virosome.

3. The hapten-carrier conjugate of formula (III) according to claim 1 or 2, wherein the carrier is a protein selected from diphtheria toxoid and $CRM_{197}$, and wherein said diphtheria toxoid and $CRM_{197}$ are each independently optionally modified.

4. A composition comprising:
   a plurality of hapten-carrier conjugates according to any one of claim 1, 2, or 3; and
   one or more adjuvants.

5. The composition according to claim 4, wherein one of the one or more adjuvants is the oligonucleotide of SEQ ID NO:1.

6. The composition according to claim 4, wherein one of the one or more adjuvants is an aluminum salt.

7. The composition according to claim 6, wherein the aluminum salt is aluminum hydroxide.

8. The composition according to claim 7, wherein the adjuvants are the oligonucleotide of SEQ ID NO:1 and aluminum hydroxide.

* * * * *